(12) United States Patent
Yamashita et al.

(10) Patent No.: US 8,333,193 B2
(45) Date of Patent: Dec. 18, 2012

(54) DRY POWDER INHALATION SYSTEM FOR TRANSPULMONARY ADMINISTRATION

(75) Inventors: Chikamasa Yamashita, Naruto (JP); Shigeru Ibaragi, Tokushima-ken (JP); Yuichiro Fukunaga, Tokushima-ken (JP); Akitsuna Akagi, Naruto (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 994 days.

(21) Appl. No.: 12/202,221

(22) Filed: Aug. 30, 2008

(65) Prior Publication Data

US 2009/0095293 A1    Apr. 16, 2009

Related U.S. Application Data

(62) Division of application No. 10/170,339, filed on Jun. 14, 2002, now Pat. No. 7,448,379.

(30) Foreign Application Priority Data

Jun. 15, 2001   (JP) ................................. 2001-182504
Dec. 28, 2001   (JP) ................................. 2001-400871
Apr. 12, 2002   (JP) ................................. 2002-111131

(51) Int. Cl.
    *A61M 16/00*    (2006.01)
    *A61M 15/00*    (2006.01)
    *A61M 15/08*    (2006.01)
    *B05D 7/14*     (2006.01)
    *B65D 83/06*    (2006.01)

(52) U.S. Cl. ............................. 128/203.15; 128/203.23

(58) Field of Classification Search ............. 128/200.14, 128/200.21, 200.22, 203.12, 203.15, 203.28
    See application file for complete search history.

(56) References Cited

U.S. PATENT DOCUMENTS

| | | |
|---|---|---|
| 3,874,381 A | 4/1975 | Baum |
| 3,921,637 A | 11/1975 | Bennie et al. |
| 4,064,878 A | 12/1977 | Lundquist |
| 5,044,091 A | 9/1991 | Ueda et al. |
| 5,326,753 A | 7/1994 | Ohtsuki et al. |

(Continued)

FOREIGN PATENT DOCUMENTS

EP   0 360 340 A1   3/1990

(Continued)

OTHER PUBLICATIONS

European Search Report for Corresponding European Application No. EP 06010993.1 dated Oct. 21, 2009.

(Continued)

*Primary Examiner* — Gary Jackson
*Assistant Examiner* — Michael Mendoza
(74) *Attorney, Agent, or Firm* — Finnegan, Henderson, Farabow, Garrett & Dunner, L.L.P.

(57) ABSTRACT

The present invention provides a novel dry powder inhalation system suitable for transpulmonary administration. The dry powder inhalation system of the invention characterized by using a combination of:
(1) a vessel housing a freeze-dried composition that contains a single dose of an active ingredient, and has:
   (i) a non-powder cake-like form,
   (ii) a disintegration index of 0.015 or more, and
   (iii) a property of becoming fine particles having a mean particle diameter of 10 microns or less or a fine particle fraction of 10% or more upon receipt of an air impact having an air speed of at least 1 m/sec and an air flow rate of at least 17 ml/sec; and
(2) a device comprising means capable of applying said air impact to the freeze-dried composition in said vessel, and means for discharging the powder-form freeze-dried composition that has been made into fine particles.

39 Claims, 16 Drawing Sheets

U.S. PATENT DOCUMENTS

| | | | |
|---|---|---|---|
| 5,349,947 | A | 9/1994 | Newhouse et al. |
| 5,354,934 | A | 10/1994 | Pitt et al. |
| 5,503,144 | A | 4/1996 | Bacon |
| 5,542,411 | A | 8/1996 | Rex |
| 5,654,007 | A | 8/1997 | Johnson et al. |
| 5,752,505 | A | 5/1998 | Ohki et al. |
| 5,785,049 | A | 7/1998 | Smith et al. |
| 5,810,004 | A | 9/1998 | Ohki et al. |
| 5,826,633 | A | 10/1998 | Parks et al. |
| 5,889,202 | A | 3/1999 | Alapati et al. |
| 5,922,354 | A | 7/1999 | Johnson et al. |
| 5,954,047 | A | 9/1999 | Armer et al. |
| 5,964,416 | A | 10/1999 | Jaeger et al. |
| 5,996,577 | A | 12/1999 | Ohki et al. |
| 6,089,228 | A | 7/2000 | Smith et al. |
| 6,153,224 | A | 11/2000 | Staniforth |
| 6,186,141 | B1 | 2/2001 | Pike et al. |
| 6,231,851 | B1 | 5/2001 | Platz et al. |
| 6,402,055 | B1 | 6/2002 | Jaeger et al. |
| 6,497,373 | B2 | 12/2002 | Jaeger et al. |
| 6,726,124 | B2 | 4/2004 | Jaeger et al. |

FOREIGN PATENT DOCUMENTS

| | | |
|---|---|---|
| EP | 0 407 276 A2 | 1/1991 |
| HU | 204993 B | 3/1992 |
| HU | 205857 B | 7/1992 |
| HU | 216770 B | 8/1999 |
| HU | 221232 B1 | 8/2002 |
| JP | 60-52847 | 4/1985 |
| JP | 03-131271 | 6/1991 |
| JP | 8-103499 | 4/1996 |
| JP | 10-508790 | 9/1998 |
| JP | 11-171760 | 6/1999 |
| JP | 11-507040 | 6/1999 |
| JP | 2000-233023 | 8/2000 |
| JP | 2001-151673 | 6/2001 |
| WO | WO 91/06333 | 5/1991 |
| WO | WO 91/16038 | 10/1991 |
| WO | WO 95/31479 | 11/1995 |
| WO | WO 96/32149 | 10/1996 |
| WO | WO 96/40068 | 12/1996 |
| WO | WO 97/23239 | 7/1997 |
| WO | WO 99/17754 | 4/1999 |
| WO | WO 00/15262 | 3/2000 |
| WO | WO 00/24444 | 5/2000 |

OTHER PUBLICATIONS

European Search Report dated Jul. 6, 2006.

P. Lucas et al., "Protein Deposition from Dry Powder Inhalers: Fine Particle Multiplets as Performance Modifiers," Pharmaceutical Research, vol. 15, No. 4, pp. 562-569 (New York, Plenum Publishing Corp.., 1998).

U. Conte et al., "Spray Dried Polyactide Microsphere Preparation: Influence of the Technological Parameters," Drug Development and Industrial Pharmacy, vol. 20, No. 3, pp. 235-258 (New York, Marcel Dekker, Inc., 1994).

K. Inazu & K. Shima, "Freeze-Drying and Quality Evaluation of Protein Drugs," Developments in Biological Standardization, vol. 74, pp. 307-322 (Basel, Switzerland, Karger AG, 1991).

G. Slama et al., "A new non-invasive method for treating insulin-reaction: Intranasal lyophilized glucagons," *Diabetologia*, 33:671-674 (1990).

"Aerosol Powder Device," A partial translation of *Nippon Rinsho*, vol. 56, No. 3 (3, 1998) p. 212 (764) left col. L6-p. 215 (767) left col. L25.

Novelty Search Report dated Jun. 30, 2004.

DRY POWDER INHALATION SYSTEM FOR TRANSPULMONARY ADMINISTRATION

This is a division of application Ser. No. 10/170,339, filed Jun. 14, 2002 now U.S. Pat. No. 7,448,379 and claims priority to Japanese Patent Application No. 2002-111131, filed Apr. 12, 2002, Japanese Patent Application No. 2001-400871, filed Dec. 28, 2001, and Japanese Patent Application No. 2001-182504, filed Jun. 15, 2001, all of which are incorporated herein by reference.

TECHNICAL FIELD

The present invention relates to a novel dry powder inhalation system suitable for transpulmonary administration. More specifically, the present invention relates to a dry powder inhalation system for transpulmonary administration according to which a freeze-dried composition provided housed in a vessel can be prepared into a form suitable for transpulmonary administration by being made into fine particles at the time of use, and administered by inhalation as is.

Furthermore, the present invention encompasses the following inventions related to the dry powder inhalation system for transpulmonary administration. Specific examples of these inventions include a freeze-dried composition which can be made into fine particle powder suitable for transpulmonary administration (dry powdered preparation for transpulmonary administration) at the time of use, a device (apparatus/implement) used in preparation and inhalation of the dry powdered preparation for transpulmonary administration, a method for producing the dry powdered preparation for transpulmonary administration, a method for transpulmonary administration by inhalation using the freeze-dried composition and use of a freeze-dried composition for preparing a dry powdered preparation for transpulmonary administration at the time of use.

Hereinafter, in this specification, the term "fine particles" includes pulverized powder (particle powder).

BACKGROUND ART

In general, with regard to transpulmonary administration, it is known that the active ingredient contained in a medicine can be delivered into the lungs efficiently by making the mean particle diameter of the active ingredient be 10 microns or less, preferably 5 microns or less. The current situation with conventional inhalations for transpulmonary administration is thus that, to make the medicine have a particle diameter suitable for transpulmonary administration in advance, fine particles are prepared by a spray drying method, a jet milling method or the like, and possibly further processing is carried out, and then the fine particles are provided filled into a dry powder inhaler.

Specifically, Japanese Unexamined Patent Publication No. 1999-171760 discloses three types of powdered inhalation, namely (1) a preparation comprising a powder-form composition comprising only medicinal fine particles filled into a suitable vessel, (2) a preparation comprising a powder-form composition in which medicinal fine particles have been granulated gently to form a relatively large particle diameter filled into a suitable vessel, and (3) a preparation comprising a powder-form composition comprising mixed particles in which medicinal fine particles and vehicle particles (lactose etc.) having a particle diameter larger than the medicinal fine particles are mixed together uniformly filled into a suitable vessel. Moreover, it is disclosed that if these powdered inhalations are administered into the respiratory tract, then the behavior shown is that with (1) the medicinal fine particles in the composition reach the lower respiratory tract, for example the trachea and the bronchi, and are deposited here, with (2) the granulated medicine separates into fine particles in flight in the respiratory tract, and the medicinal fine particles produced reach the lower respiratory tract, for example the trachea and the bronchi, and are deposited here, and with (3) the vehicle is deposited in the oral cavity, on the pharynx or on the larynx, and the medicinal fine particles only reach the lower respiratory tract, for example the trachea and the bronchi, and are deposited here.

In this way, with a conventional powdered inhalation for transpulmonary administration, the ingredient to be inhaled is made into desirable fine particles in advance, and then these fine particles, or else these fine particles further processed by some method, are filled into a dry powder inhaler, and transpulmonary administration is carried out using this.

To make a low-molecular-weight drug into fine particles, a spray drying method (for example, a method disclosed in Japanese Unexamined Patent Publication No. 1999-171760), a jet milling method (for example, a method disclosed in Japanese Unexamined Patent Publication No. 2001-151673) or the like is usually used. The jet milling method comprises applying an air impact having an air flow rate of at least 1000 L/min and an air speed not less than the sonic speed to a low-molecular-weight drug to make the drug into fine particles. No method is known which makes the drug into fine particles by a low air impact.

For a high-molecular-weight drug such as a peptide or protein, on the other hand, for example a method in which a spray solution of a medicinal stock liquid containing additives is subjected to spray drying, thus making the stock liquid into fine particles having a mean particle diameter of 5 microns or less in one step, and then these fine particles are filled into a dry powder inhaler (spray drying method: WO 95/31479), and a method in which a peptide or protein is freeze-dried along with additives, and then the freeze-dried composition is made into fine particles by jet milling or the like, and these fine particles are filled into a dry powder inhaler (freeze drying-jet milling method: WO 91/16038) are known.

However, conventional powdered inhalations for transpulmonary administration prepared by the above-mentioned spray drying method or freeze drying-jet milling method are not necessarily ideal preparations for high-molecular-weight drugs such as peptides and proteins in particular. For example, as shown by the disclosure in WO 95/31479 that about 25% deactivation of interferon occurs during the spray drying process, it is anticipated that if the spray drying method is used, then proteins and the like will be deactivated in the manufacturing process and the activity of the drug will thus decrease.

No method is known which makes a high-molecular-weight drug into fine particles by a low air impact, the same as a low-molecular-weight drug.

Moreover, with both the spray drying method and the freeze drying-jet milling method, an operation is required in which the fine powder prepared is collected from the spray drying apparatus or jet milling apparatus and is subdivided and filled into vessels. It is thus inevitable that, accompanying this operation, problems will arise such as the yield of the preparation decreasing due to collection or filling loss and the cost rising correspondingly, and the preparation being contaminated with impurities. Moreover, in general it is difficult to subdivide and fill the powder in small amounts with good accuracy. If the spray drying method or the freeze drying-jet milling method, for which such subdividing and filling of small amounts in powder form is essential, is used, then it is thus necessary to establish a method of filling with small amounts and good accuracy of powder. In actual fact, details of a system, apparatus and method for filing with a fine powder are disclosed in U.S. Pat. No. 5,826,633.

DISCLOSURE OF THE INVENTION

It is an object of the present invention to solve the various problems of the above-mentioned conventional powdered inhalations for transpulmonary administration. Specifically, it is an object of the present invention to provide a novel preparation system and administration system that enables a freeze-dried composition that has been housed in vessels in advance subdivided into single doses of active ingredient to be made into fine particles down to a particle diameter suitable for transpulmonary administration by inhalation in the vessel at the time of usage, and then be used for transpulmonary administration as is.

The present inventors carried out assiduous studies to attain the above object, and as a result discovered that if a pharmacologically active substance is filled as a liquid into vessels subdivided into required amounts and then freeze-dried, then the non-powder-form freeze-dried composition thus prepared can unexpectedly be made into fine particles by a relatively low air impact while still housed in the vessel. Based on this knowledge, the present inventors carried out further studies, and as a result discovered that by using a freeze-dried composition, a single dose of which has been housed in a non-powder form in a vessel, combined with a device comprising means for introducing air at a prescribed speed and flow rate into the vessel so as to be capable of applying a prescribed air impact to the composition, and means for discharging from the vessel the powdered composition that has been made into fine particles, then the freeze-dried preparation can be prepared into a fine particle powder form suitable for transpulmonary administration easily by a user at the time of use (specifically, at the time of inhalation), and the fine particle powder can be administered by inhalation as is. Moreover, it was verified that, according to this transpulmonary administration system, all of the previously mentioned problems of conventional powdered inhalations for transpulmonary administration can be solved.

That is, according to the above-mentioned transpulmonary administration system of the present invention, it is not necessary to collect the pharmaceutical preparation in a powder form and then fill it into vessels, but rather preparation is carried out by accurately filling each vessel with liquid and then carrying out freeze drying, and hence the transpulmonary administration system can be used for transpulmonary administration with an extremely high accuracy and high preparation yield, and without the problem of contamination. Moreover, according to the above-mentioned administration system, active ingredients such as proteins or peptides are not exposed to high temperature in the manufacturing process as is the case with the spray drying method and the like, and hence there is no problem of the pharmacological activity dropping due to exposure to high temperature. Therefore, the administration system of the present invention is an extremely useful system in particular with pharmacologically active substances such as peptides and proteins that are expensive drugs, since the manufacturing cost can be reduced.

Moreover, according to the dry powder inhalation system of the present invention, an extremely high fine particle fraction (the amount of the drug reaching the lungs: fine particle fraction, respirable fraction) is obtained, and hence the drug can be delivered into the lungs efficiently.

The dry powder inhalation system of the invention is characterized by using a freeze-dried composition in a non-powder cake-like form as a preparation for manufacturing a powdered preparation for transpulmonary administration. The dry powder inhalation system of the invention in which the freeze-dried composition in a cake-like form is applied to a dry powder inhaler is capable of achieving a significantly higher fine particle fraction compared to the case where a preparation made into fine particle powder having a size suitable for transpulmonary administration using a method employed for powder inhalants heretofore known, such as a jet milling method or a spray drying method, is applied to a dry powder inhaler of the invention.

For such reasons, the dry powder inhalation system of the present invention can be ranked as a high-performance transpulmonary administration system.

The present invention was developed based on this knowledge.

(I) The present invention includes the following dry powder inhalation system for transpulmonary administration.

The dry powder inhalation system for transpulmonary administration comprises a combination of a freeze-dried composition that exists in a non-powder form in a vessel and is capable of being made into fine particles having a mean particle diameter of 10 microns or less within the vessel after applying a prescribed air impact to the freeze-dried composition in the vessel, a device capable of applying the above-mentioned air impact to the freeze-dried composition in the vessel, and a device capable of discharging the thus obtained fine particles.

The following can be put forward as specific embodiments of this dry powder inhalation system for transpulmonary administration.

A dry powder inhalation system for transpulmonary administration, using a combination of:
(1) a vessel housing a freeze-dried composition that contains a single dose of an active ingredient, and has:
  (i) a non-powder cake-like form,
  (ii) a disintegration index of 0.015 or more, and
  (iii) a property of becoming fine particles having a mean particle diameter of 10 microns or less or a fine particle fraction of 10% or more upon receiving an air impact having an air speed of at least 1 m/sec and an air flow rate of at least 17 ml/sec; and
(2) a device having means capable of applying said air impact to the freeze-dried composition in said vessel and means for discharging the powder-form freeze-dried composition that has been made into fine particles.

(II) Furthermore, the present invention includes the following freeze-dried compositions pulverized into fine particles having a particle size suitable for transpulmonary administration using an air impact.

A freeze-dried composition for transpulmonary administration having the following properties (i) to (iii):
  (i) has a non-powder cake-like form,
  (ii) has a disintegration index of 0.015 or more, and
  (iii) becomes fine particles having a mean particle diameter of 10 microns or less or a fine particle fraction of 10% or more upon receipt of an air impact having an air speed of at least 1 m/sec and an air flow rate of at least 17 ml/sec.

(III) Furthermore, the present invention includes the following dry powder inhalers usable in the dry powder inhalation system for transpulmonary administration.

The inhalers are used for administering the fine particles obtained by applying an air impact to a freeze-dried composition that has been housed in a non-powder form in a vessel to a user by inhalation. Specific examples of such inhalers comprise ① means capable of applying an air impact having an air speed of at least 1 m/sec and an air flow rate of at least 17 ml/sec to the freeze-dried composition in the vessel, and ② means for discharging the powder-form freeze-dried composition that has been pulverized into fine particles. More specifically, the inhalers encompass jet type dry powder inhalers as in (a) below and self-inhaling type dry powder inhalers as in (b) below.

(a) Jet Type Dry Powder Inhaler: Active Powder Inhaler

A device used in making a freeze-dried composition that has been housed in a non-powder form in a vessel into fine particles and administering the obtained fine particles to a user by inhalation, comprising a needle part having an air jet flow path, a needle part having a discharge flow path, air pressure-feeding means for feeding air into the air jet flow path of the needle part, and an inhalation port that communicates with the discharge flow path, and being constituted such that a stopper that seals up the vessel is pierced by the needle parts, thus communicating the air jet flow path and the discharge flow path with the inside of the vessel, and air is jetted into the vessel from the air jet flow path using the air pressure-feeding means, thus breaking down the freeze-dried composition into fine particles by the impact of the jetted air, and discharging the fine particles obtained from the inhalation port via the discharge flow path.

(b) Self-Inhaling Type Dry Powder Inhaler: Passive Powder Inhaler

A device used in making a freeze-dried composition that has been housed in a non-powder form in a vessel into fine particles and administering the obtained fine particles to a user, by inhalation, comprising a needle part having a suction flow path, a needle part having an air introduction flow path, and an inhalation port that communicates with the suction flow path, and being constituted such that, in a state in which a stopper that seals up the vessel has been pierced by the needle parts, through the inhalation pressure of a user, air in the vessel is inhaled from the inhalation port, and at the same time outside air flows into the vessel, which is now at a negative pressure, through the air introduction flow path, and as a result the freeze-dried composition is pulverized into fine particles by the impact of the air flowing in, and the fine particles obtained are discharged from the inhalation port through the suction flow path.

(IV) Furthermore, the present invention includes the following methods of manufacturing a powdered preparation for transpulmonary administration.

A method of manufacturing a dry powdered preparation for transpulmonary administration, comprising:

introducing air into a vessel to apply to a freeze-dried composition an air impact having an air speed of at least 1 m/sec and an air flow rate of at least 17 ml/sec using a device capable of applying said air impact to the freeze-dried composition in the vessel, thereby making said freeze-dried composition into fine particles having a mean particle diameter of 10 microns or less or a fine particle fraction of 10% or more;

the freeze-dried composition containing a single dose of an active ingredient and having the following properties:
 (i) has a non-powder cake-like form,
 (ii) has a disintegration index of 0.015 or more, and
 (iii) becomes fine particles having a mean particle diameter of 10 microns or less or a fine particle fraction of 10% or more upon receipt of the air impact.

(V) Furthermore, the present invention includes the following transpulmonary administration methods characterized by using a dry powder inhalation system for transpulmonary administration as described above. According to the transpulmonary administration method, a freeze-dried composition that has been housed in a non-powder form in a vessel is pulverized into a fine particle powder suitable for transpulmonary administration at the time of use so that a user (patient) can administer the fine-particle-form powdered preparation by inhalation. The following embodiments are included in the administration method.

A transpulmonary administration method comprising:

making a freeze-dried composition into fine particles having a mean particle diameter of 10 microns or less or a fine particle fraction of 10% or more by applying an air impact having an air speed of at least 1 m/sec and an air flow rate of at least 17 ml/sec to the freeze-dried composition at the time of use, and administering the resulting fine particle powder to a user by inhalation;

the freeze-dried composition containing a single dose of an active ingredient and having the following properties:
 (i) has a non-powder cake-like form,
 (ii) has a disintegration index of 0.015 or more, and
 (iii) becomes fine particles having a mean particle diameter of 10 microns or less or a fine particle fraction of 10% or more upon receipt of the air impact.

(VI) Furthermore, the present invention includes the following uses of a freeze-dried composition for transpulmonary administration.

Use of a freeze-dried composition for transpulmonary administration by inhalation, the freeze-dried composition containing a single dose of an active ingredient and having the following properties:
 (i) has a non-powder cake-like form,
 (ii) has a disintegration index of 0.015 or more, and
 (iii) becomes fine particles having a mean particle diameter of 10 microns or less or a fine particle fraction of 10% or more upon receipt of an air impact having an air speed of at least 1 m/sec and an air flow rate of at least 17 ml/sec, and being used by pulverizing into fine particles having said mean particle diameter or said fine particle fraction.

(VII) Furthermore, the following uses of a freeze-dried composition for manufacture of a dry powdered preparation for transpulmonary administration are included in the present invention.

Use of a freeze-dried composition for manufacture of a dry powdered preparation for transpulmonary administration by inhalation, the freeze-dried composition having the following properties:
 (i) has a non-powder cake-like form,
 (ii) has a disintegration index of 0.015 or more, and
 (iii) becomes fine particles having a mean particle diameter of 10 microns or less or a fine particle fraction of 10% or more upon receipt of an air impact having an air speed of at least 1 m/sec and an air flow rate of at least 17 ml/sec, and being used by pulverizing into fine particles having said mean particle diameter or said fine particle fraction at the time of use.

Figure 1:
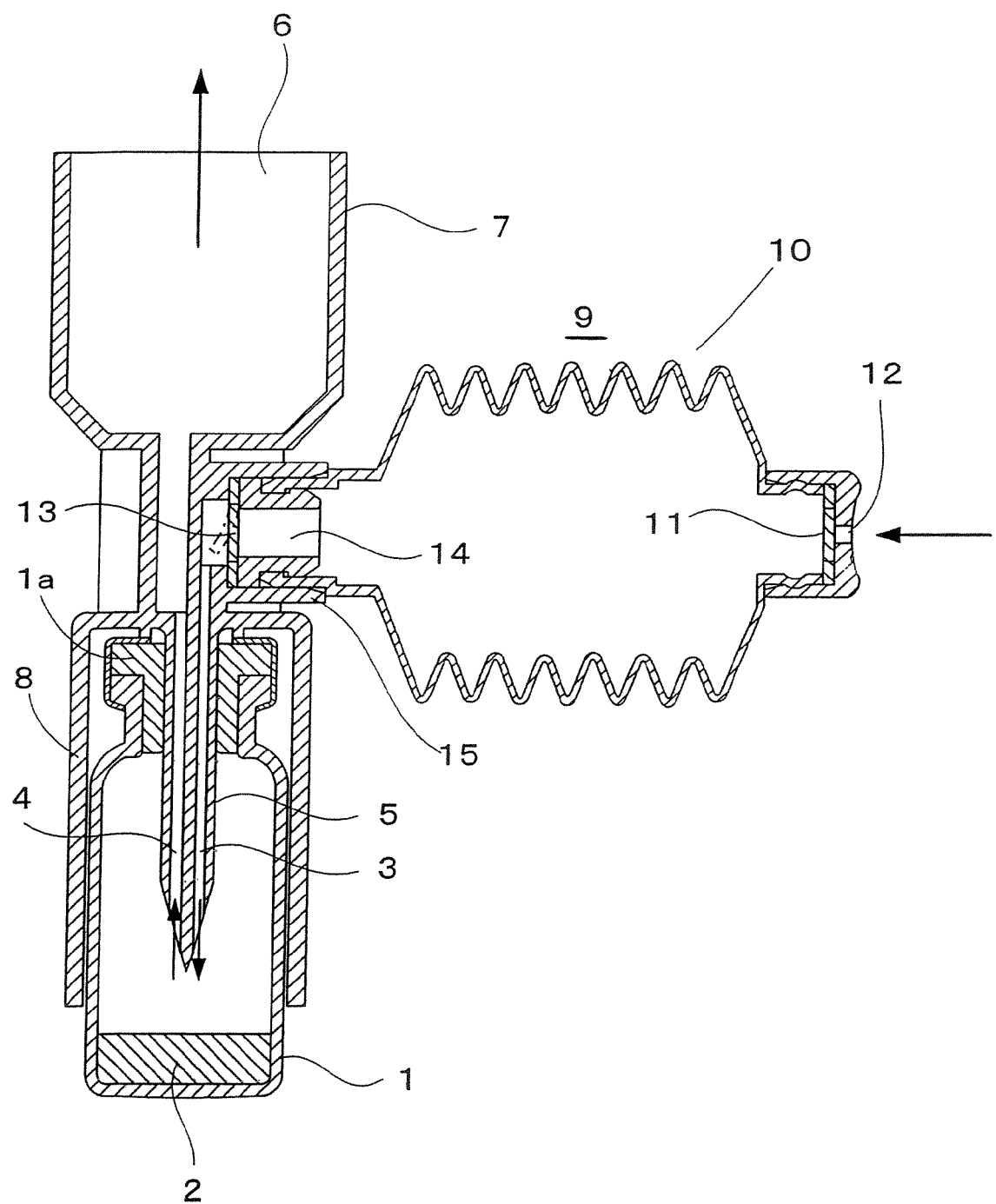
FIG. 1 is a sectional view showing a dry powder inhaler (jet type 1) of the present invention disclosed as Embodiment 1.

Note that, in the drawing, the arrows indicate the flow of external air (likewise in FIGS. 2 and 3 below).

Moreover, the meanings of the various reference numerals are as follows: 1. vessel, 1a. stopper, 2. freeze-dried composition, 3. air jet flow path, 4. discharge flow path, 5. needle part, 6. inhalation port, 7. air intake member, 8. tubular safety cover, 9. air pressure-feeding means, 10. bellows body, 11. intake valve, 12. intake port, 13. discharge valve, 14. discharge port, 15. connecting port (likewise in FIGS. 2 to 11 below).

Figure 2:
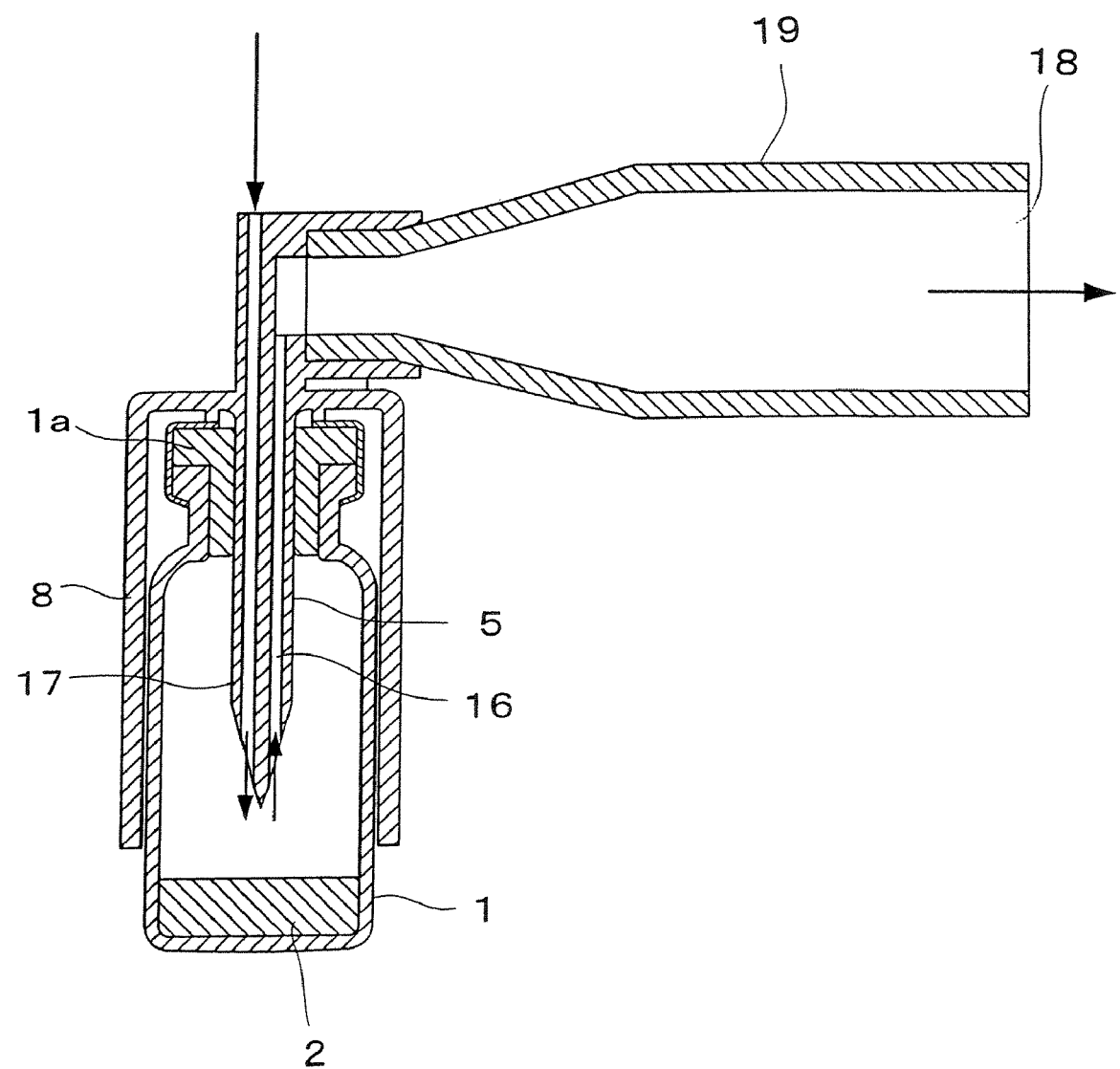

FIG. 2 is a sectional view showing a dry powder inhaler (self-inhaling type 1) of the present invention disclosed as Embodiment 2. Moreover, the meanings of the various reference numerals are as follows: 16. suction flow path, 17. air introduction flow path, 18. inhalation port, 19. air intake member (likewise in FIG. 3 below).

Figure 3:
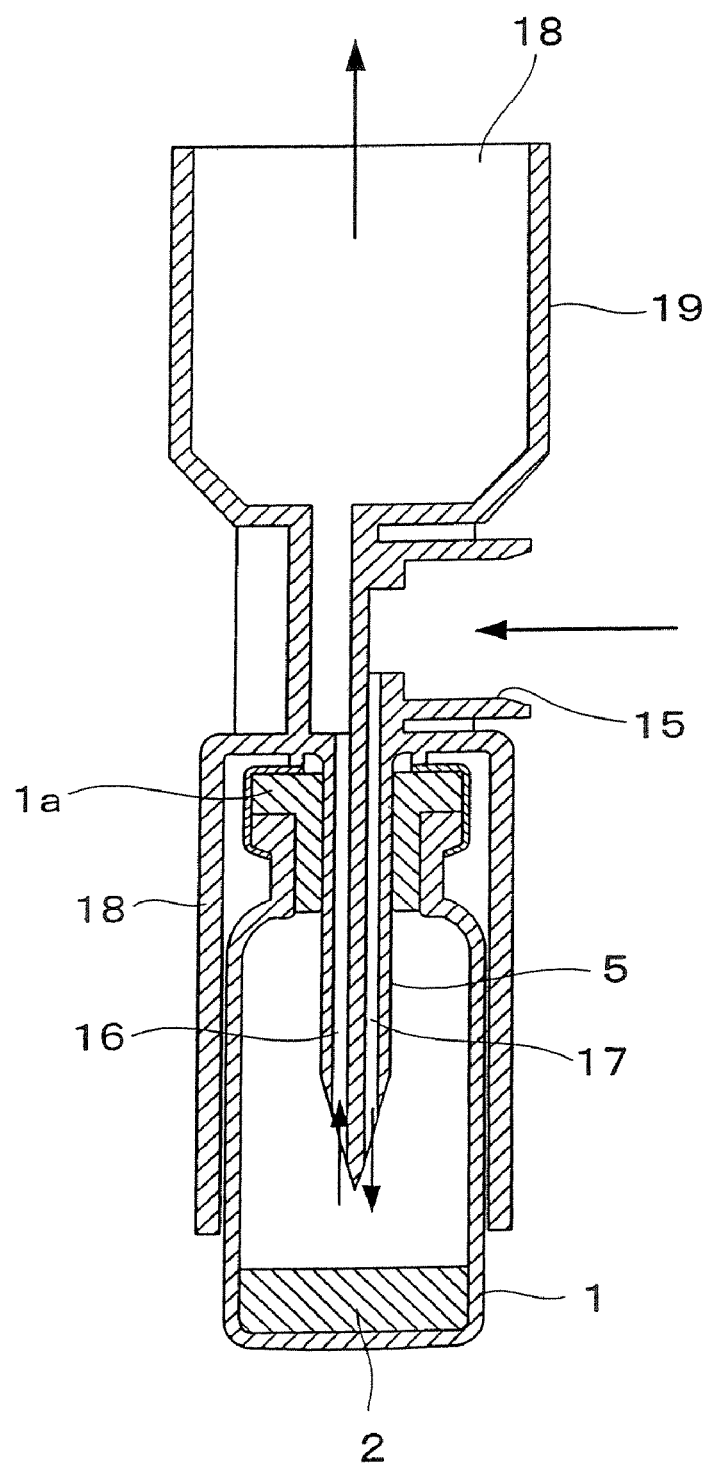

FIG. 3 is a sectional view showing a dry powder inhaler (self-inhaling type 2) of the present invention disclosed as Embodiment 3.

Figure 4:
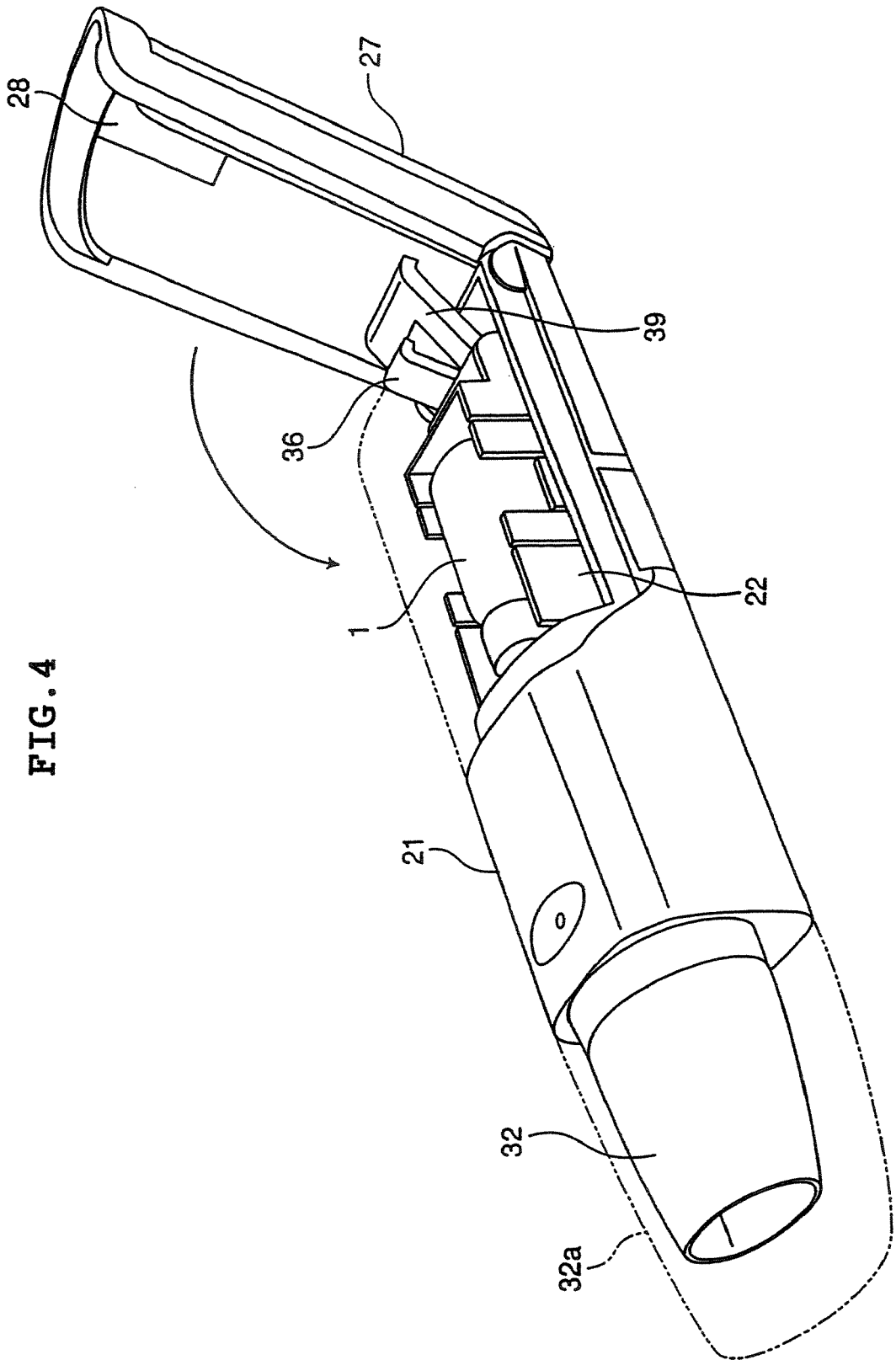

FIG. 4 is a perspective view showing a dry powder inhaler (self-inhaling type 3) of the present invention disclosed as Embodiment 4. Moreover, the meanings of the reference numerals are as follows: 21. housing, 22. holder part, 27. lid, 28. window, 32. mouthpiece, 32a. mouthpiece cap, 39. connector (likewise in FIGS. 5 to 13 below).

Figure 5:
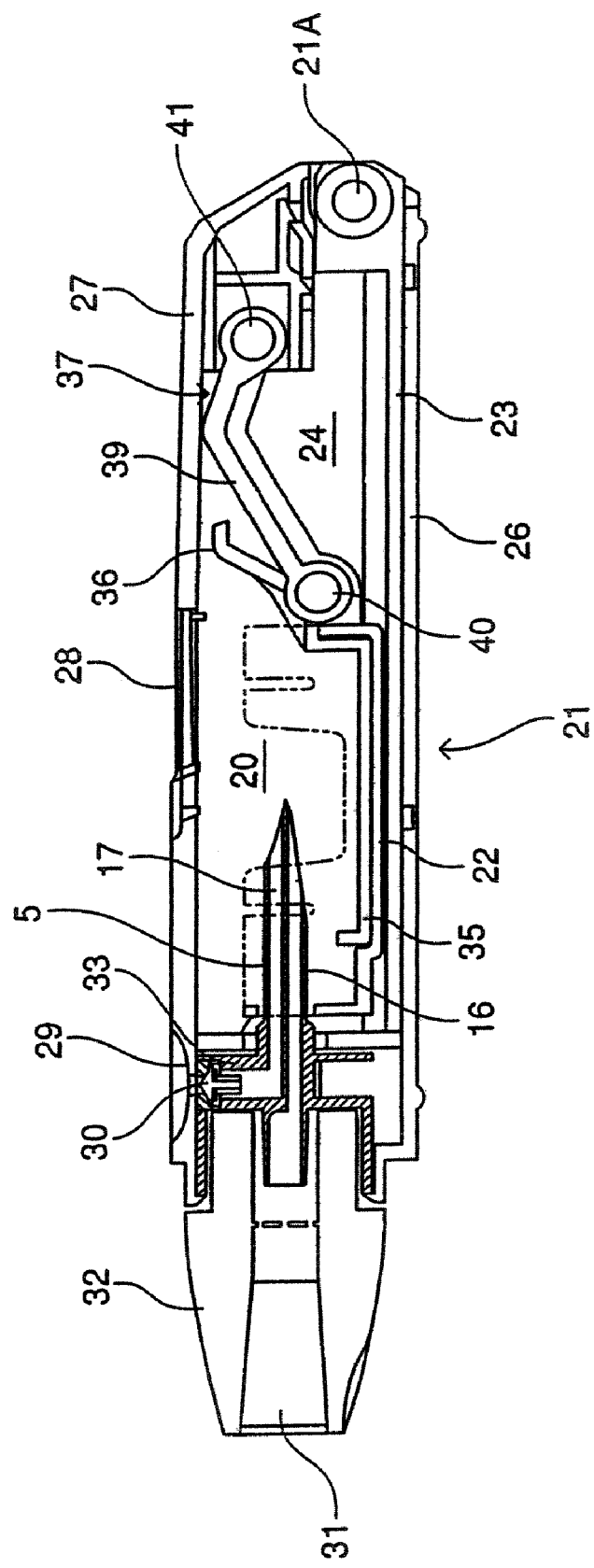

FIG. 5 is a sectional view of the above-mentioned dry powder inhaler (self-inhaling type 3). Moreover, the meanings of the reference numerals are as follows: 20. housing chamber, 21A. hinge, 23. guide part, 24. holder operating part, 26. housing main body, 29. introduction port, 30. check valve, 31. suction port, 33. partition part, 35. remover, 36. lever, 37. mechanism part, 39. connector, 40. hinge, 41. hinge (likewise in FIGS. 6 to 13 below).

FIG. 6(a) is a sectional view of part of the above-mentioned dry powder inhaler (self-inhaling type 3). (b) is a side view of the needle part of this dry powder inhaler. Moreover, the meanings of the reference numerals are as follows: 16a. tip opening of suction flow path 16, 17a. tip opening of air introduction flow path 17, 34. peripheral wall part, 42. second introduction path, 42a. introduction groove in partition part 33, 42b. introduction groove in peripheral wall part 34, 43. gap, 44. one end of second introduction path 42, 45. other end of second introduction path 42, 46. vent hole, 47. wall (likewise in FIGS. 7 to 13 below).

FIGS. 7 to 10 are sectional views for explaining the operation of the above-mentioned dry powder inhaler (self-inhaling type 3). Reference numeral 25 indicates a removal/insertion port.

Figure 11:
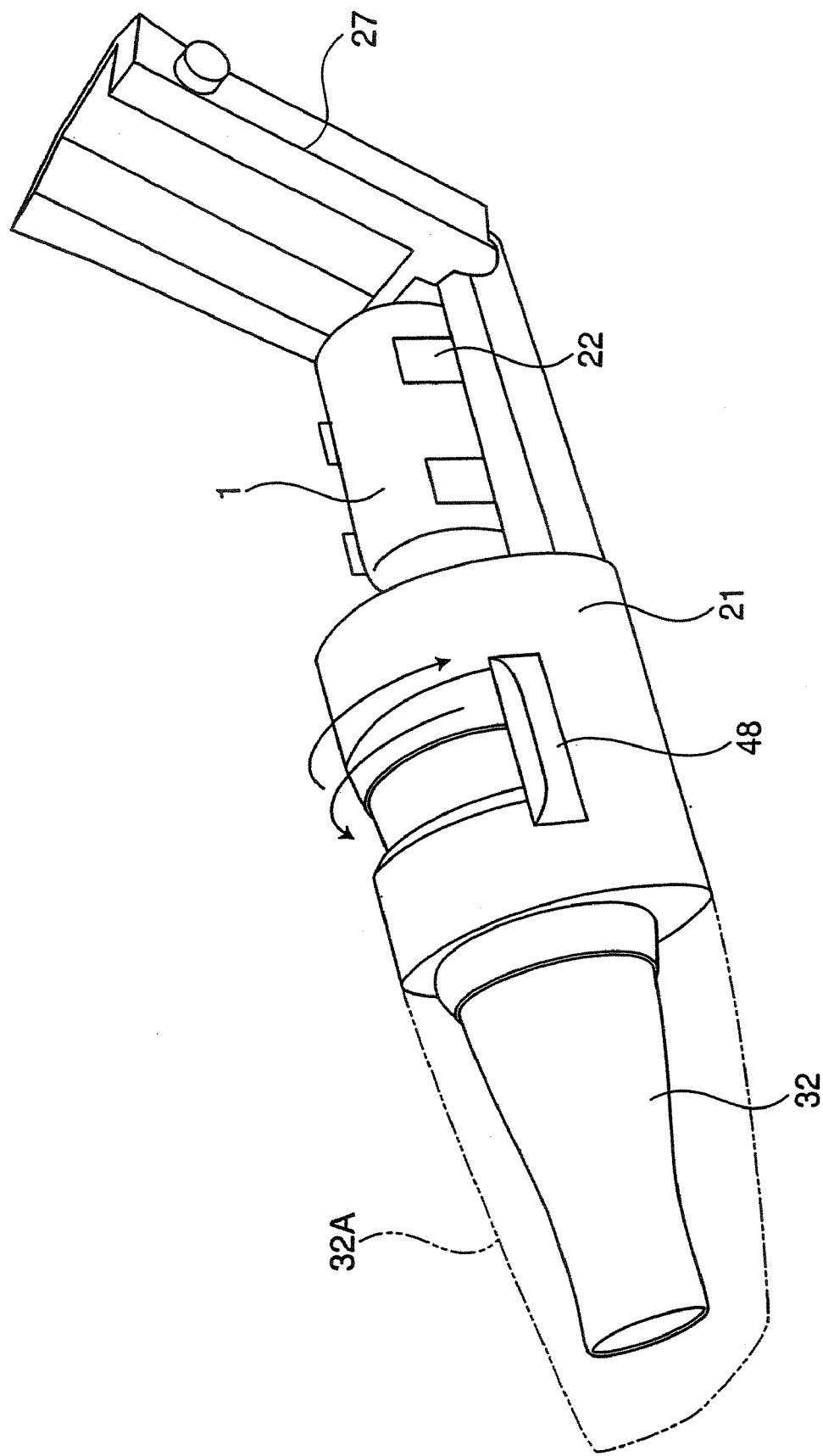

FIG. 11 is a perspective view of a dry powder inhaler (self-inhaling type 4), which is another embodiment of the present invention. Reference numeral 48 indicates an operator.

Figure 12:
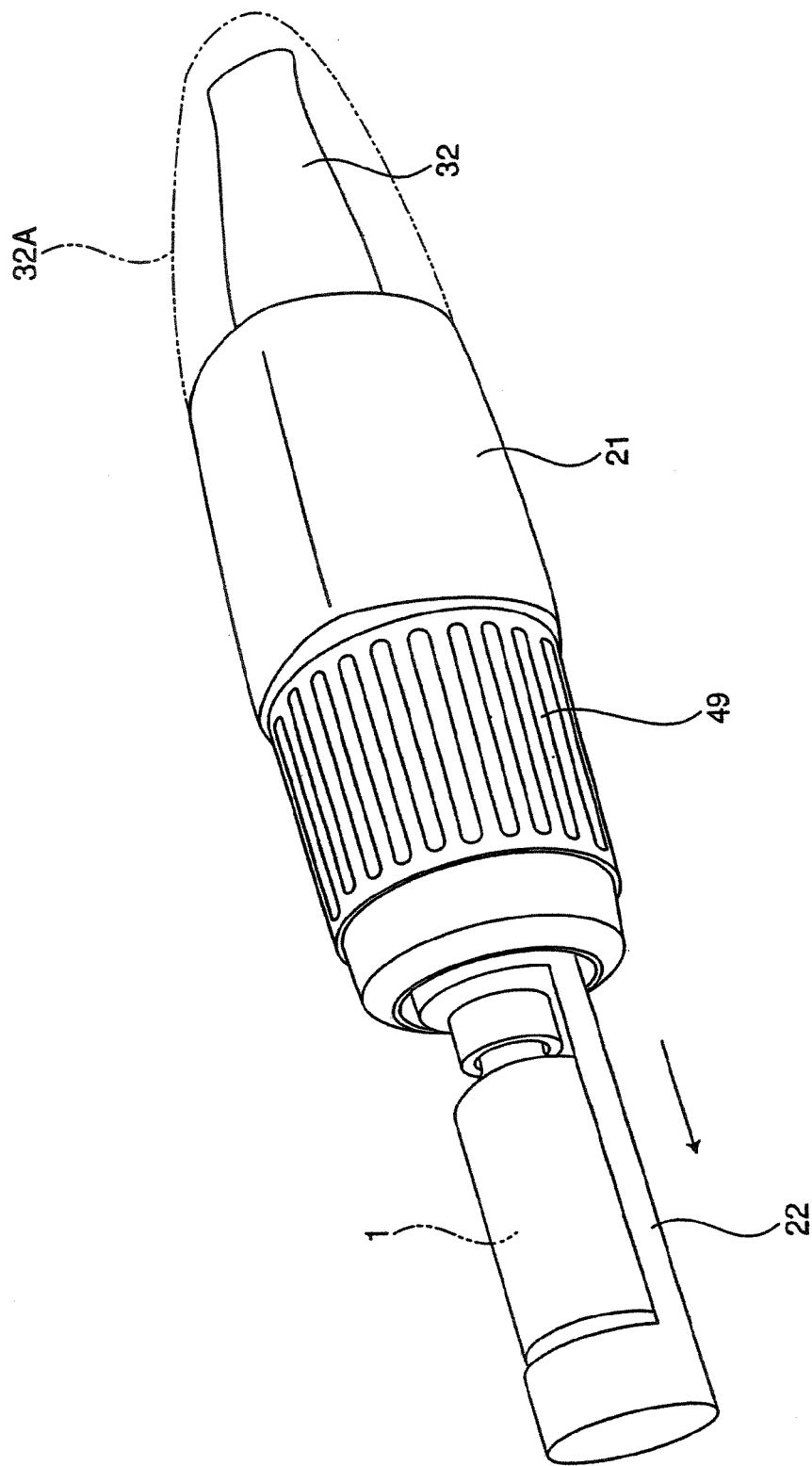
Figure 13:
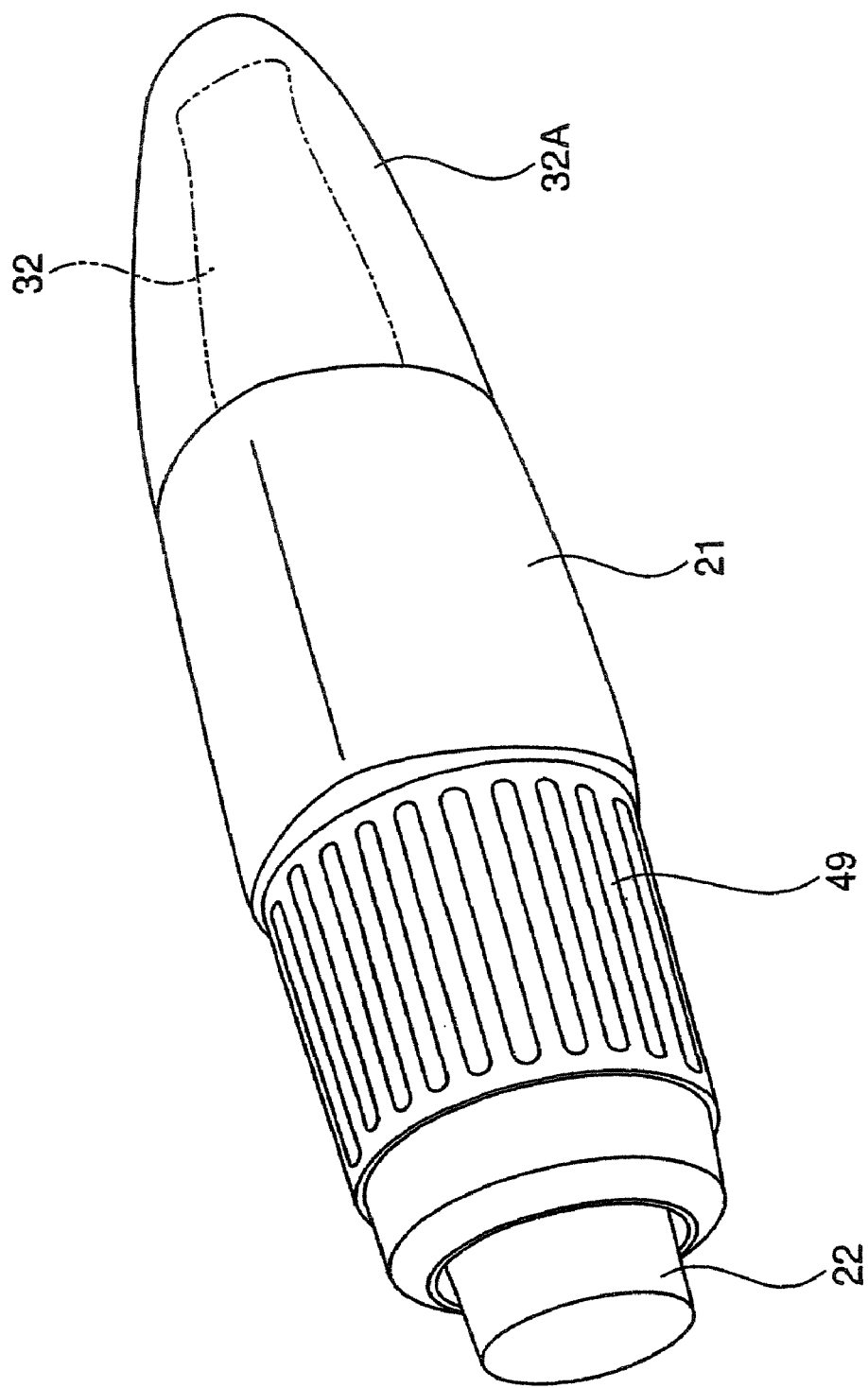

FIGS. 12 and 13 are perspective views of a dry powder inhaler (self-inhaling type 5) of another embodiment of the present invention. Reference numeral 49 indicates an operator.

Figure 14:
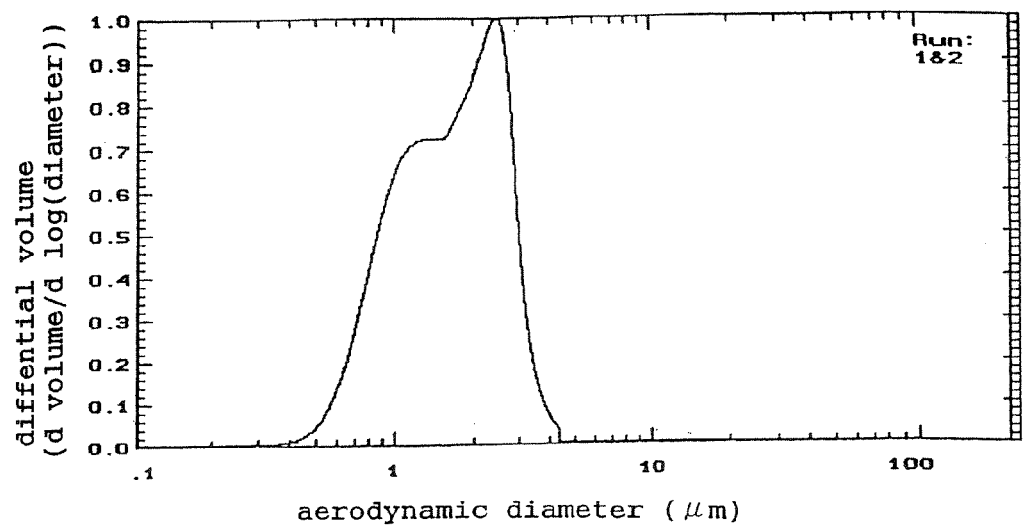

FIG. 14 is a graph showing the particle size distribution of fine particles jetted out from the dry powder inhaler in Example 1.

Figure 15:
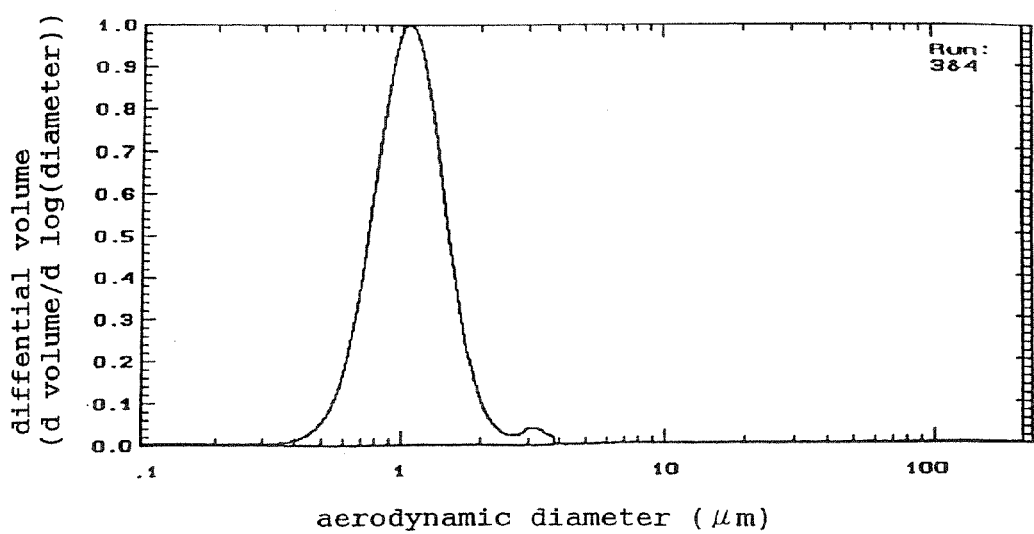

FIG. 15 is a graph showing the particle size distribution of fine particles jetted out from the dry powder inhaler in Example 2.

Figure 16:
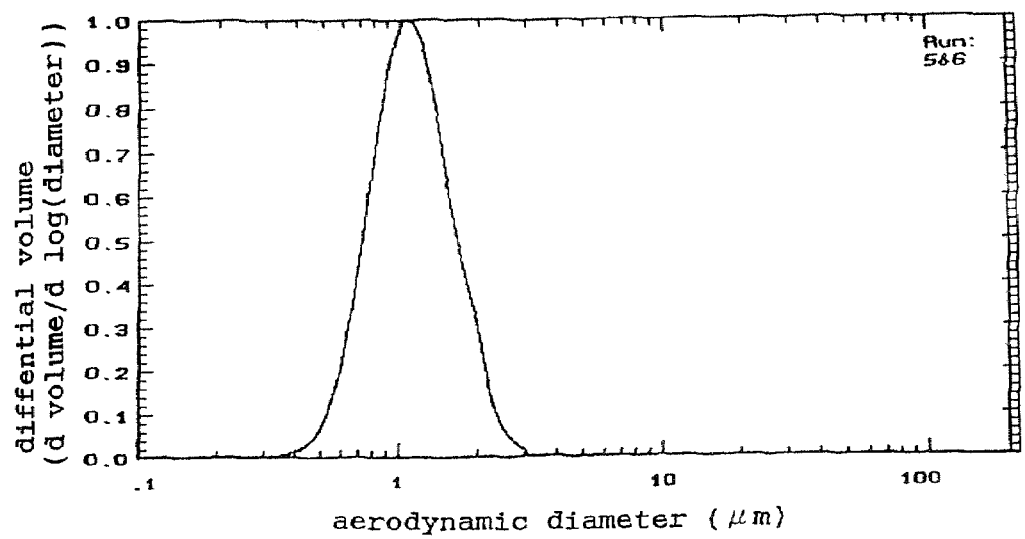

FIG. 16 is a graph showing the particle size distribution of fine particles jetted out from the dry powder inhaler in Example 3.

Figure 17:
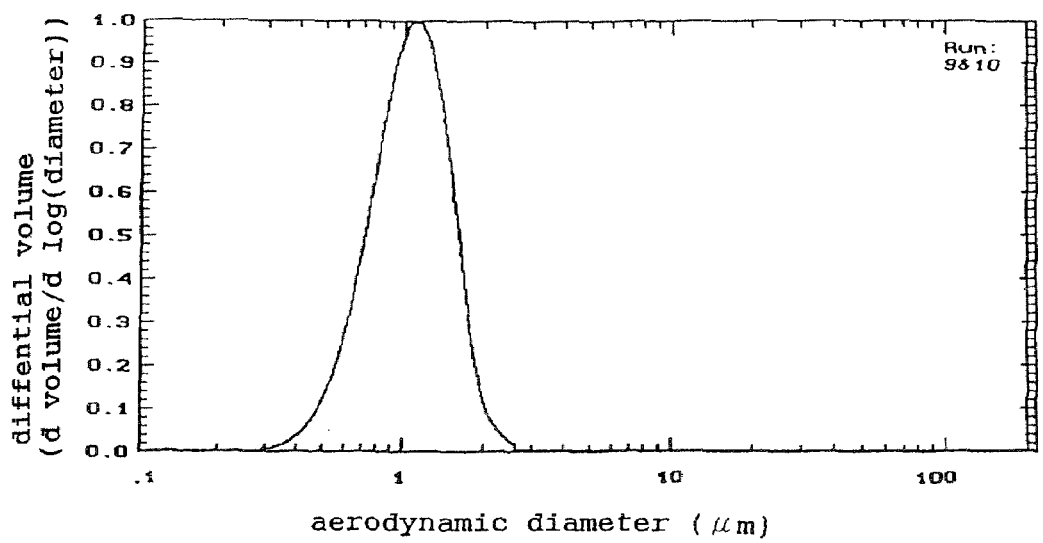

FIG. 17 is a graph showing the particle size distribution of fine particles jetted out from the dry powder inhaler in Example 4.

Figure 18:
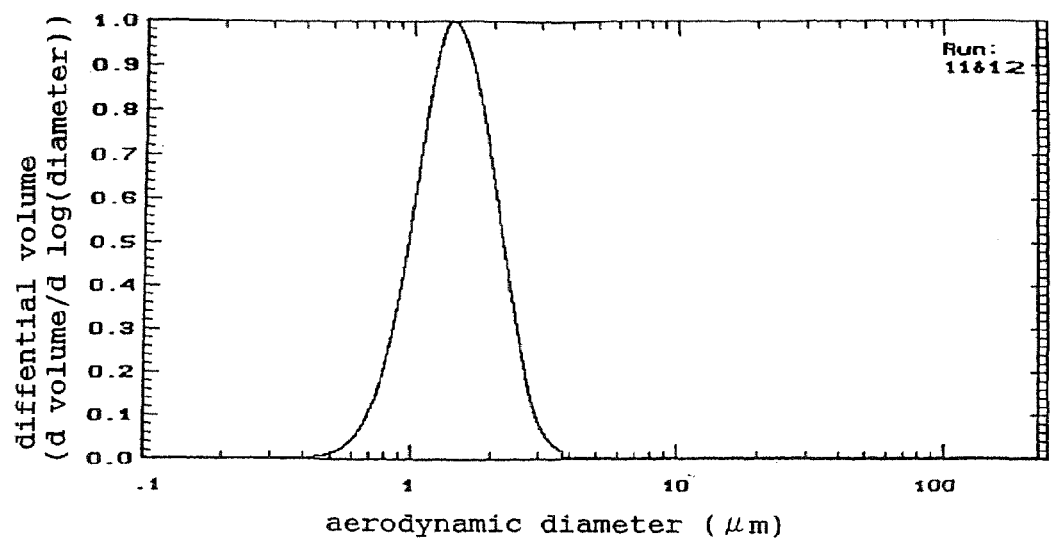

FIG. 18 is a graph showing the particle size distribution of fine particles jetted out from the dry powder inhaler in Example 5.

Figure 19:
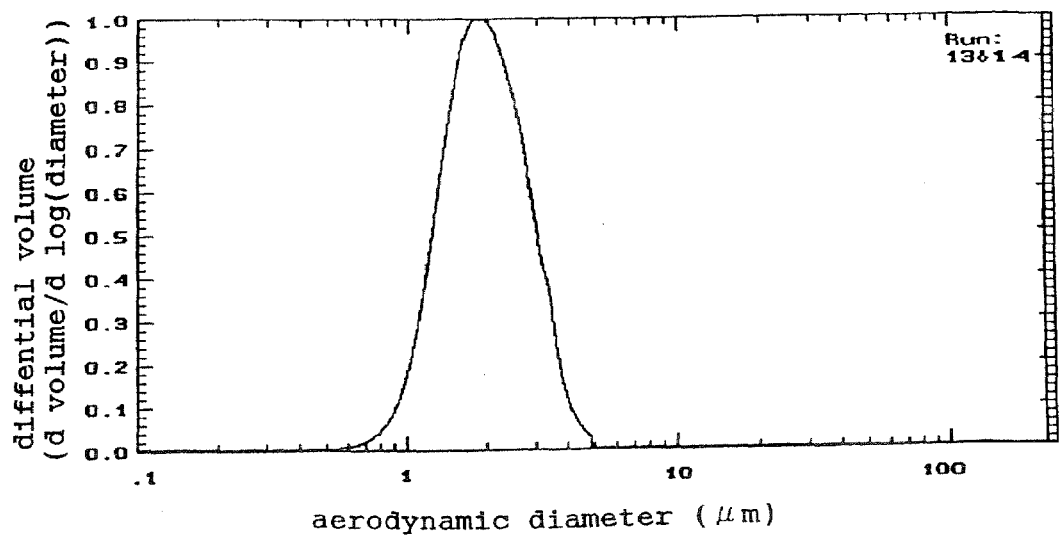

FIG. 19 is a graph showing the particle size distribution of fine particles jetted out from the dry powder inhaler in Example 6.

BEST MODE FOR CARRYING OUT THE INVENTION (1) Dry Powder Inhaler

The dry powder inhaler used in the present invention is a device used for breaking down a freeze-dried preparation (freeze-dried composition) that has been housed in a non-powder form in a vessel into fine particles in the vessel, and allowing a user to inhale the dry powdered preparation.

By comprising ① means capable of applying an air impact to the non-powder form freeze-dried composition in a degree such that the freeze-dried composition can be pulverized into fine particles, and ② means capable of administering to a user by inhalation the powder-form freeze-dried composition that has been made into fine particles, the device can carry out both breaking down of the freeze-dried composition into fine particles and administration of the powdered composition to a user by inhalation. Note that means ① can also appreciated as means for introducing air having the above-mentioned air impact into the vessel housing the freeze-dried composition. Moreover, means ② can also appreciated as means for discharging out of the vessel the powdered preparation that has been made into fine particles in the vessel. In a dry powder inhalation system of the present invention, as long as the device comprises these means, either a conventional publicly-known device or a device which will be developed in the future can also be used.

Specifically, the means ① can be realized by introducing air capable of applying an air impact as above into the vessel housing the freeze-dried composition. Note that the means ① can be altered into means capable of applying an air impact having an air speed of at least 1 m/sec and an air flow rate of at least 17 ml/sec to the freeze-dried composition in the vessel.

By using the means ② or via this means, the dry powdered preparation, which has been prepared into a form suitable for transpulmonary administration, can be administered by inhalation to the user such as patient. Note that, for example a chamber or a flow path such that the composition is made into fine particles or scattered may be further provided in the means ②.

The device in question encompasses jet type dry powder inhalers as in (a) below and self-inhaling type dry powder inhalers as in (b) below.

(a) Jet Type Dry Powder Inhaler: Active Powder Inhaler (a-1) A dry powder inhaler used in the making into fine particles and inhalation of a freeze-dried composition that has been housed in a non-powder form in a vessel, comprising a needle part having an air jet flow path, a needle part having a discharge flow path, air pressure-feeding means for feeding air into the air jet flow path of the needle part, and an inhalation port that communicates with the discharge flow path, and being constituted such that a stopper that seals up the vessel is pierced by the needle parts, thus communicating the air jet flow path and the discharge flow path with the inside of the vessel, and air is jetted into the vessel from the air jet flow path using the air pressure-feeding means, thus breaking down the freeze-dried composition into fine particles by the impact of the jetted air, and discharging the fine particles obtained out from the inhalation port via the discharge flow path.

(a-2) The dry powder inhaler described in (a-1) above, being constituted such that the air pressure-feeding means is manually operated and comprises a bellows body having an intake port equipped with an intake valve and a discharge port equipped with a discharge valve, and by contracting the bellows body and thus opening the discharge valve in a state in which the intake valve is closed, air in the bellows body is pressure-fed into the vessel through the air jet flow path of the needle part which communicates with the discharge port, and by expanding the bellows body through an elastic restoring force in a state in which the discharge valve is closed and the intake valve is open, air is introduced into the bellows body.

(a-3) The dry powder inhaler described in (a-1) or (a-2) above, in which the air jet flow path and the discharge flow path are formed in a single needle part.

(b) Self-Inhaling Type Dry Powder Inhaler: Passive Powder Inhaler (b-1) A dry powder inhaler used for inhaling fine particles obtained by breaking down a freeze-dried composition that has been housed in a non-powder form in a vessel, comprising a needle part having a suction flow path, a needle part having an air introduction flow path, and an inhalation port that communicates with the suction flow path, and being constituted such that, in a state in which a stopper that seals up the vessel has been pierced by the needle parts, through the inhalation pressure of a user, air in the vessel is inhaled from the inhalation port, and at the same time outside air flows into the vessel, which is now at a negative pressure, through the air introduction flow path, and as a result the freeze-dried composition is broken down into fine particles by the impact of the air flowing in, and the fine particles obtained are discharged from the inhalation port through the suction flow path.

(b-2) The dry powder inhaler described in (b-1) above, being constituted such that most part of the freeze-dried composition is made into fine particles and discharged from the inhalation port through one inhalation of the user.

(b-3) The dry powder inhaler described in (b-1) or (b-2) above, in which the suction flow path and the air introduction flow path are formed in a single needle part.

The means for introducing air into the vessel (means ①) mentioned above) may be means for introducing air from the outside at normal pressure. It is not necessary to use compressed air from a jet mill or the like. There are no limitations on the means for introducing air from the outside. For example, in the case where the jet type dry powder inhaler (active powder inhaler) described above is used, means for artificially introducing external air into the vessel by jetting can be employed. In the case where the self-inhaling type dry powder inhaler (passive powder inhaler) is used, means for naturally introducing outside air into the vessel by suction through negative pressure formed in the vessel when the user inhales can be employed. Moreover, in the former case, i.e. in the jet type dry powder inhaler (active powder inhaler), the method of introducing external air into the vessel by jetting artificially may be manual or may be a method that is carried out automatically using a machine.

The dry powder inhaler of the invention, regardless of the type of the inhaler, whether it is an active powder inhaler or a passive powder inhaler, is capable of breaking down the freeze-dried composition that has been stored in non-powder form in the vessel into fine particles using an impact (jet pressure) of external air introduced into (flowing into) the vessel by the air introduction means.

For example, a vessel, used for freeze-drying can be used here, with no limitations on the material, shape etc. As the material, a plastic mainly including a polyolefin such as polyethylene, polypropylene or polystyrene, glass, aluminum and the like can be given as examples. Moreover, as the shape, a circular cylinder, a cup shape, and a polygonal prism (polygonal pyramid) such as a triangular prism (triangular pyramid), a square prism (square pyramid), a hexagonal prism (hexagonal pyramid) or an octagonal prism (octagonal pyramid) can be given as examples.

To obtain the effects efficiently, the volume of the vessel housing the freeze-dried composition is in a range of 0.2 to 50 ml, preferably 0.2 to 25 ml and more preferably 1 to 15 ml. Moreover, it is desirable to be used the trunk diameter of the vessel be 2 to 100 mm, preferably 2 to 75 mm, more preferably 2 to 50 mm.

Moreover, the amount of the freeze-dried composition housed in the vessel is preferably an amount containing a unit dose (single dose) or a plurality of doses, specifically 2 to 3 doses, of the active ingredient. More preferably, it is an amount containing a unit dose (single dose) of the active ingredient. Moreover, the specific amount of the freeze-dried composition will vary according to the type and content of the active ingredient contained in the freeze-dried composition, and is selected as appropriate from amounts that can be inhaled, with there being no particular limitation; nevertheless, the amount is generally 30 mg or less, preferably 20 mg or less, more preferable 10 mg or less, particularly preferably 5 mg or less.

Moreover, the air impact generated by the outside air introduced into the vessel is stipulated through the air flow rate at which air flows into the vessel through at least one or a plurality of inhalations of a person or the air speed thus generated. There is no particular limitation on introducing external air with an air flow rate or air speed greater than this, except of course that the durability of the vessel is a limitation. Generally the air flow rate for one inhalation of a person is 5 to 300 L/min, more specifically 10 to 200 L/min. Moreover, in the case of an dry powder inhaler, a device can be used such that the amount of air jetted each time is 5 to 100 ml, preferably 10 to 50 ml. Preferably, adjustment can be carried out such that an air impact generated through an air speed of at least 1 m/sec is applied to the surface of the freeze-dried composition filled in the vessel. A more preferable air impact is an impact generated by an air speed of at least 2 m/sec, a yet more preferable one is an impact generated by an air speed of at least 5 m/sec, and a still more preferable one is an impact generated by an air speed of at least 10 m/sec. Here, there is no particular limitation on the upper limit of the air impact, but an impact generated by an air speed of 300 m/sec can be given as an example. The upper limit is preferably an impact generated through an air speed 250 m/sec, more preferably an impact generated through an air speed 200 m/sec, yet more preferably an impact generated through an air speed 150 m/sec.

There is no particular limitation on the air impact as long as it is generated by air having an air speed arbitrarily selected from the range extending from a lower limit to an upper limit. Specific examples are impacts generated through an air speed in a range of 1 to 300 m/sec, 1 to 250 m/sec, 2 to 250 m/sec, 5 to 250 m/sec, 5 to 200 m/sec, 10 to 200 m/sec or 10 to 150 m/sec.

Here, the speed of the air applied to the freeze-dried composition can be measured as follows. That is, with the jet type dry powder inhaler shown later as Embodiment 1, a mechanism is adopted in which air stored in a bellows body 10 is forcibly introduced onto the freeze-dried composition (cake-like freeze-dried composition: hereinafter also referred to as 'freeze-dried cake') that has been filled into the vessel from an air jet flow path 3, thus applying an air impact, and discharging the resulting fine particles from a discharge flow path 4. In this case, the flow rate of the air flowing through the air jet flow path 3 can be calculated by dividing the amount of air stored in the bellows body 10 by the time over which the air is fed into the vessel. Next, by dividing this air flow rate by the cross-sectional area of a path to introduce air into the vessel such as the air jet flow path 3, the air speed at which the impact is applied to the freeze-dried composition (freeze-dried cake) can be calculated.

Air speed (cm/sec)=air flow rate (ml=cm$^3$/sec)÷cross-sectional area of air introduction flow path (cm$^2$)

Specifically, in the case for example of a jet type dry powder inhaler designed such that the bore of the air jet flow path 3 is 1.2 mm, the bore of the discharge flow path is 1.8 mm, and the amount of air stored in the bellows body 10 is about 20 ml, in the case that the amount of air of about 20 ml stored in the bellows body 10 is forcibly introduced onto the freeze-dried composition in the vessel from the air jet flow path 3 in about 0.5 seconds, the air flow rate becomes about 40 ml/sec. Dividing this value by the cross-sectional area of the air introduction flow path (the air jet flow path) (0.06×0.06×3.14=0.0113 cm$^2$), gives 3540 cm/sec. The air speed is thus about 35 m/sec.

Moreover, with the self-inhaling type dry powder inhalers shown later as Embodiments 2, 3 and 4, a mechanism is adopted in which air flowing in from an air introduction flow path 17 applies an impact to the freeze-dried cake, and then the resulting fine particles are discharged from a suction flow path 16; the bores of the air introduction flow path 17 and the suction flow path 16 thus stipulate the flow rate of the air flowing through the paths. The air speed applied to the freeze-dried composition in the vessel can thus be calculated by measuring the flow rate of the air flowing through the air introduction flow path 17 and dividing this by the cross-sectional area of the air introduction flow path 17.

Air speed (cm/sec)=air flow rate (ml=cm$^3$/sec)÷cross-sectional area of air introduction flow path 17 (cm$^2$)

Specifically, the flow rate of the air flowing through the air introduction flow path 17 can be measured by installing the dry powder inhaler including the vessel in the slot part of apparatus A (a twin impinger: made by Copley, UK) as mentioned in the European Pharmacopoeia (Third Edition Supplement 2001, p 113-115), and using a flow meter (KOFLOC DPM-3).

For example, with a self-inhaling type dry powder inhaler designed such that the bore of the air introduction flow path 17 is 1.99 mm and the bore of the suction flow path is 1.99 mm, in the case that the air flow rate flowing through the air introduction flow path 17 measured using the flow meter (KOFLOC DPM-3) was 17.7 L/min, i.e. 295 ml/sec, the air speed can be obtained by dividing this value by the cross-sectional area of the air introduction flow path 17 (0.0995× 0.0995×3.14=0.0311 cm$^2$) (9486 cm/sec, i.e. 95 m/sec).

Moreover, at least 17 ml/sec can be given as an example of the flow rate of the air applied to the freeze-dried composition filled in the vessel. The air flow rate is preferably at least 20 ml/sec, more preferably at least 25 ml/sec. Here there is no particular limitation on the upper limit of the air flow rate, but an example of 900 L/min can be given. This upper limit is preferably 15 L/sec, more preferably 10 L/sec, yet more preferably 5 L/sec, still more preferably 4 L/sec, particularly preferably 3 L/sec. Specifically, the flow rate should be in a range constituted from a lower limit and an upper limit selected as appropriate from the above, with there being no particular limitation; nevertheless, 17 ml/sec to 15 L/sec, 20 ml/sec to 10 L/sec, 20 ml/sec to 5 L/sec, 20 ml/sec to 4 L/sec, 20 ml/sec to 3 L/sec, and 25 ml/sec to 3 L/sec, can be given as examples of the range.

Moreover, as means for raising the impact pressure of the air introduced from the outside, the dry powder inhaler used in the present invention can have means for discharging air from a discharge port, as explained in detail below, preferably with a small bore, of a flow path close to the freeze-dried composition housed at the bottom of the vessel, for example a needle part having an air introduction flow path or an air jet flow path as described later in the embodiments. Regarding the bore of the discharge port of the flow path, the preferable range varies according to the size of the vessel and so on, with there being no particular limitations; nevertheless, the bore can be in a range of 0.3 to 10 mm, preferably 0.5 to 5 mm, more preferably 0.8 to 5 mm, much more preferably 1 to 4 mm.

The freeze-dried composition housed in a non-powder form in the vessel can be made into fine particles by introducing air into the vessel. Here, the extent of making into fine particles should be such that the particle diameter is suitable for transpulmonary administration; a particle diameter of 10 μm or less, preferably 5 μm or less, can be given as an example.

As used herein, the mean particle diameter of fine particles indicates a mean particle diameter usually adopted in the industry relating to inhalants. Specifically, the mean particle diameter is not a geometric particle diameter, but an aerodynamic mean particle diameter (mass median aerodynamic diameter, MMAD). The aerodynamic mean particle diameter can be measured by a conventional method.

For example, the mass median aerodynamic diameter can be measured using a dry particle size distribution meter fitted with an Aerobreather, which is an artificial lung model (made by Amherst Process Instrument, Inc., USA), a twin impinger (G. W. Hallworth and D. G. Westmoreland: J. Pharm. Pharmacol., 39, 966-972 (1987), U.S. Pat. No. 6,153,224), a multi-stage liquid impinger, a Marple-Miller impactor, an Andersen cascade impactor or the like. Moreover, B. Olsson et al. have reported that delivery of the particles into the lungs increases at the proportion of particles having a mass median aerodynamic diameter of 5 μm or less increases (B. Olsson et al.: Respiratory Drug Delivery V, 273-281 (1996)). The fine particle fraction, fine particle dose or the like as measured by a twin impinger, a multi-stage liquid impinger, a Marple-Miller impactor, an Andersen cascade impactor or the like acts as a method of estimating the amount that can be delivered into the lungs. In the invention, the proportion of effective particles (fine particle fraction) is at least 10%, preferably at least 20%, more preferably 25%, yet more preferably at least 30%, particularly preferably at least 35%.

The dry powder inhaler for use in the invention encompasses the specific embodiments defined in the following items 100 to 111:

100. A dry powder inhaler for transpulmonary administration used for making a freeze-dried composition that has been housed in non-powder form in a vessel into fine particles by an air impact, and administering the resulting fine particles to a user by inhalation.

101. The dry powder inhaler for transpulmonary administration according to item 100, being a device used for making a freeze-dried composition that has been housed in non-powder form in a vessel into fine particles, and administering the resulting fine particles to a user by inhalation, comprising a needle part having an air jet flow path, a needle part having a discharge flow path, air pressure-feeding means for feeding air into the air jet flow path of said needle part, and an inhalation port that communicates with the discharge flow path of said needle part, and characterized by being constituted such that a stopper that seals up said vessel is pierced by said needle parts, thus communicating the air jet flow path and the discharge flow path with the inside of said vessel, and air is jetted into said vessel through said air jet flow path using said air pressure-feeding means, thus pulverizing said freeze-dried composition into fine particles by the impact of the jetted air, and discharging the fine particles obtained from the inhalation port via said discharge flow path.

102. The dry powder inhaler for transpulmonary administration according to item 100, being a device used for pulverizing a freeze-dried composition that has been housed in non-powder form in a vessel into fine particles, and administering the resulting fine particles to a user by inhalation, comprising a needle part having a suction flow path, a needle part having an air introduction flow path, and an inhalation port that communicates with said suction flow path, and characterized by being constituted such that, in a state in which a stopper sealing up said vessel has been pierced by said needle parts, through the inhalation pressure of the user, air in said vessel is inhaled from said inhalation port, and at the same time outside air flows into said vessel, at a negative pressure, through said air introduction flow path, and as a result said freeze-dried composition is pulverized into fine particles by the impact of the air flowing in, and the fine particles obtained are discharged from the inhalation port through said suction flow path.

103. The dry powder inhaler for transpulmonary administration according to item 101, characterized by being constituted such that said freeze-dried composition is pulverized into fine particles and discharged from said inhalation port through jetting air into said vessel once.

104. The dry powder inhaler for transpulmonary administration according to item 101, characterized by being constituted such that said freeze-dried composition is pulverized into fine particles, such that the mean particle diameter is 10 microns or less or the fine particle fraction is 10% or more, and discharged from said inhalation port through jetting air into said vessel.

105. The dry powder inhaler for transpulmonary administration according to item 101, wherein said air jet flow path and said discharge flow path are formed in a single needle part.

106. The dry powder inhaler for transpulmonary administration according to item 102, characterized by being constituted such that said freeze-dried composition is pulverized into fine particles and discharged from said inhalation port through one inhalation of the user.

107. The dry powder inhaler for transpulmonary administration according to item 102, characterized by being constituted such that said freeze-dried composition is pulverized into fine particles, such that the mean particle diameter is 10 microns or less or the fine particle fraction is 10% or more, and discharged from said inhalation port through inhalation of the user.

108. The dry powder inhaler for transpulmonary administration according to item 102, wherein said suction flow path and said air introduction flow path are formed in a single needle part.

109. The dry powder inhaler for transpulmonary administration according to item 108 comprising:

a holder part for holding a vessel that is sealed up with a stopper and houses a freeze-dried composition in a non-powder cake-like form that will be made into fine particles upon receiving an air impact, means for applying an air impact to said freeze-dried composition in said vessel, and sucking said freeze-dried composition in a powder-form that has been made into fine particles by the air impact out from said vessel, a needle part having a suction flow path for sucking said freeze-dried composition out from said vessel, and an air introduction flow path for introducing outside air into said vessel, a suction port that communicates with said suction flow path of said needle part, a guide part for guiding said holder part in the axial direction of said needle part, a holder operating part that has a mechanism part for, when said vessel is held by said holder part, advancing the vessel towards a needle tip of said needle part to pierce the stopper of the vessel with said needle tip, and retreating the vessel from said needle tip to separate the stopper of the vessel from said needle tip, and an operator that operates the mechanism part, and is constituted such that said operating member can be operated with a force smaller than the force necessary for the mechanism part to pierce the stopper of the vessel with said needle part, and a housing that supports said needle part and is for providing said suction port, said guide part and said holder operating part, and constituted such that, in a state in which said stopper has been pierced by said needle part to communicate the suction flow path and the air introduction flow path of said needle part with the inside of said vessel and position the tip of the air introduction flow path at said freeze-dried composition, through the inhalation pressure of a user, air in said vessel is inhaled from said suction port, and air is made to flow into said vessel through the air introduction flow path, thus applying an air impact to the freeze-dried composition in said vessel.

110. The dry powder inhaler for transpulmonary administration according to item 109, characterized in that said housing is formed in a tubular shape, said suction port is formed at a tip part of the housing, a housing chamber for housing said vessel via said holder is formed in said housing, said needle part is disposed in said housing such that said needle tip points towards said housing chamber, and an introduction port for introducing outside air that communicates with the air introduction flow path of said needle part is provided in a wall of said housing, and the dry powder inhaler is constituted such that said holder part is advanced and retreated in the axial direction of said housing in said housing chamber using said holder operating part.

111. The dry powder inhaler for transpulmonary administration according to item 110, characterized in that said housing is formed from a housing main body having a removal/insertion port for said vessel formed therein in a position in which said holder part is retreated, and a lid for said removal/insertion port that is connected to said housing main body by a hinge, and the dry powder inhaler is constituted such that said holder operating part has said mechanism part which advances said holder part towards the needle tip of the needle part when said lid is pushed down to close said removal/insertion port, and retreats said holder part away from said needle tip when said lid is lifted up to open said removal/insertion port, and said lid is used as the operating member of said mechanism part.

(2) Freeze-Dried Composition

The freeze-dried composition of the present invention is a composition that is prepared in a non-powder dry form by filling solution containing a single effective dose or a plurality of effective doses of a drug into a vessel and then freeze-drying as is. It is preferably a freeze-dried composition containing a single effective dose of the drug. The non-powder-form freeze-dried composition can be manufactured by the same method as a conventional manufacturing method used for a freeze-dried preparation (freeze-dried composition) such as an injection that is dissolved at the time of use, in which a liquid is filled in subdivided amounts into vessels; by selecting a suitable composition (types and amounts of active ingredient and carrier used together with the active ingredient) such that the disintegration index of the freeze-dried composition prepared is 0.015 or more, the freeze-dried composition can be made into fine particles down to a particle diameter suitable for transpulmonary administration in an instant by receiving an impact of external air (air impact, jet pressure) introduced into (flowing into) the vessel.

Note that the disintegration index in the present invention is a value characteristic of the freeze-dried composition that can be obtained by measuring following the undermentioned method.

<Disintegration Index>

0.2 to 0.5 ml of a mixture containing target components that will constitute the freeze-dried composition is filled into a vessel having a trunk diameter of 18 mm or 23 mm, and freeze-drying is carried out. Next, 1.0 ml of n-hexane is instilled gently down the wall of the vessel onto the non-powder-form freeze-dried composition obtained. Agitation is carried out for about 10 seconds at 3000 rpm, and then the mixture is put into a UV cell of optical path length 1 mm and optical path width 10 mm, and the turbidity is measured immediately at a measurement wavelength of 500 nm using a spectrophotometer. The turbidity obtained is divided by the total amount (weight)) of the components constituting the freeze-dried composition, and the value obtained is defined as the disintegration index.

Here, an example of the lower limit of the disintegration index of the freeze-dried composition of the invention can be given as the above-mentioned 0.015, preferably 0.02, more preferably 0.03, yet more preferably 0.04, still more preferably 0.05. Especially, 0.1 is preferable. Moreover, there is no particular limitation on the upper limit of the disintegration index of the freeze-dried composition of the invention, but an example can be given as 1.5, preferably 1, more preferably 0.9, yet more preferably 0.8, still more preferably 0.7. The freeze-dried composition of the present invention preferably has a disintegration index in a range constituted from a lower limit and an upper limit selected as appropriate from the above, with the proviso that the disintegration index is at least 0.015. Specific examples of the range of the disintegration index are 0.015 to 1.5, 0.02 to 1.0, 0.03 to 0.9, 0.04 to 0.8, 0.05 to 0.7 and 0.1 to 0.7.

Moreover, it is preferable to prepare the freeze-dried composition of the present invention in a non-powder cake-like form by freeze-drying. In the present invention, 'non-powder-form freeze-dried composition' means a dry solid obtained by freeze-drying a solution, and is generally called a 'freeze-dried cake'. However, even if cracks appear in the cake, the cake breaks into a plurality of large lumps, or part of the cake breaks into a powder during the freeze-drying process or during subsequent handling, this cake is still included as a non-powder-form freeze-dried composition that is the subject of the present invention, provided the effects of the present invention are not impaired.

As described above, the freeze-dried composition of the invention has a disintegration index of 0.015 or more and a non-powder cake-like form and becomes fine particles having a mean particle diameter of 10 microns or less or a fine particle fraction of 10% or more upon receipt of an air impact having an air speed of at least 1 m/sec and an air flow rate of at least 17 ml/sec.

A preferable freeze-dried composition is such that, upon receiving the above air impact, the mean particle diameter becomes 10 microns or less and preferably 5 microns or less or a fine particle fraction of 10% or more, preferably 20% or more, more preferably 25% or more, still more preferably 30% or more, and especially more preferably 35% or more.

As described above, the air impact applied to a freeze-dried composition is not limited, as long as it is generated by air having an air speed of at least 1 m/sec and an air flow rate of at least 17 ml/sec.

Specific examples of an air impact include an impact generated by an air having a speed of 1 m/sec or more, preferably 2 m/sec or more, more preferably 5 m/sec or more and a still more preferably 10 m/sec or more. Here, there is no limitation on the upper limit of the air speed, but it is generally 300 m/sec, preferably 250 m/sec, more preferably 200 m/sec and yet more preferably 150 m/sec. The air speed is not limited as long as it is arbitrary selected from the range extending from a lower limit to an upper limit; however, the ranges of 1 to 300 m/sec, 1 to 250 m/sec, 2 to 250 m/sec, 5 to 250 m/sec, 5 to 200 m/sec, 10 to 200 m/sec or 10 to 150 m/sec can be given as examples.

Examples of the air impact include those generated by air having an air flow rate of generally 17 ml/sec or more, preferably 20 ml/sec or more and more preferably 25 ml/sec or more. There is no limitation on the upper limit of the air flow rate; however, the air flow rate is generally 900 L/min, preferably 15 L/sec, more preferably 5 L/sec yet more preferably 4 L/sec. Especially, 3 L/sec is very preferable. More specifically, the air flow rate is not limited as long as it is selected from the range extending from a lower limit to an upper limit; however, examples of such a range include 17 ml/sec to 15 L/sec, 20 ml/sec to 10 L/sec, 20 ml/sec to 5 L/sec, 20 ml/sec to 4 L/sec, 20 ml/sec to 3 L/sec and 25 ml/sec to 3 L/sec.

In principle, there is no particular limitation on the drug used in the present invention, provided it is a drug that can be used as a powdered inhalation (powdered inhalation for transpulmonary administration); nevertheless, synthetic low-molecular-weight drugs and high-molecular-weight drugs can be given as specific examples. High-molecular-weight drugs include physiologically active substances such as proteins, peptides or polypeptides, antibodies, genes, nucleic acids, enzymes, hormones and the like.

Moreover, regarding the disease targeted by the drug, both whole body treatment and local treatment can be envisaged, depending on the case.

Examples of synthetic low-molecular-weight drugs include, for example, hydrocortisone, prednisolone, triamcinolone, dexamethasone, betamethasone, beclometasone, fluticasone, mometasone, budesonide, salbutamol, salmeterol, procaterol, buprenorphine hydrochloride, apomorphine, taxol, and antibiotics such as tobramycin.

Examples of bio-drugs (physiologically active substances) such as proteins, peptides or polypeptides, antibodies, genes, nucleic acids, enzymes and hormones include, for example, interferons (α, β, γ), interleukins (for example, interleukin-1, 2, 3, 4, 5, 6, 7, 8, 9, 10, 11, 12, 13, 14, 15, 16, 17, 18 etc.), anti-interleukin-1α antibody, interleukin-1 receptor, interleukin receptor antagonist, interleukin-4 receptor, anti-interleukin-2 antibody, anti-interleukin-6 receptor antibody, interleukin-4 antagonist, interleukin-6 antagonist, anti-interleukin-8 antibody, chemokine receptor antagonist, anti-interleukin-7 receptor, anti-interleukin-7 antibody, anti-interleukin-5 antibody, interleukin-5 receptor, anti-interleukin-9 antibody, interleukin-9 receptor, anti-interleukin-10 antibody, interleukin-10 receptor, anti-interleukin-14 antibody, interleukin-14 receptor, anti-interleukin-15 antibody, interleukin-15 receptor, interleukin-18 receptor, anti-interleukin-18 antibody, erithropoietin (EPO), erithropoietin derivatives, granulocyte colony stimulating factor (G-CSF), granulocyte macrophage colony stimulating factor (GM-CSF), macrophage colony stimulating factor (M-CSF), calcitonin, insulin, insulin derivatives (LisPro, NovoRapid, HOE901, NN-304, etc.), insulintropin, insulin-like growth factor, glucagon, somatostatin and analogs thereof, vasopressin and analogs thereof, amylin, human growth hormone, luteinizing hormone releasing hormone, follicle stimulating hormone, growth hormone releasing factor, parathyroid hormone, endothelial cell growth factor, platelet derived growth factor, keratinocyte growth factor, epidermal growth factor, fibroblast growth factor, brain-derived neurotrophic factor, ciliary neurotrophic factor, tumor necrosis factor (TNF), TNF receptor, TNF inhibitor, transforming growth factor (TGF), hepatocyte growth factor (HGF), nerve growth factor (NGF), blood stem cell growth factor, platelet growth simulator, naturiuretic peptide, blood coagulation factor, blood hepatocyte growth factor (S-CSF), FLT3 ligand, anti-platelet aggregation inhibiting monoclonal antibody, tissue plasminogen activator and derivatives thereof, superoxide dismutase, antisense drugs, immunosuppression agents (for example, cyclosporin, tacrolimus hydrate, etc.) cancer repressor gene p53, cystic fibrosis transmembrane conductance regulator (CFTR) gene, α-1 antitrypsin, thrombopoietin (TPO), metastatin, deoxyribonuclease (Dnase), prolactin, oxytocin, thyrotopin releasing hormone (TRH), bactericidal permeability increasing (BPI) protein, and vaccine preparations, for example influenza vaccines, AIDS vaccines, rotavirus vaccines, malaria vaccines and tuberculosis vaccines such as Mtb72f.

One of these active ingredients can be used alone, or two or more can be used in combination. Note that the various peptides above encompass natural polypeptides, gene recombinant polypeptides, chemically synthesized polypeptides and so on.

The freeze-dried composition of the present invention may comprise the active ingredient alone, as long as the end products satisfy the above-mentioned disintegration index, or a suitable carrier may be mixed in. In the case of using a carrier in addition to the active ingredient, there are no particular limitations on the type and amount of the carrier used, so long as the final freeze-dried composition prepared by mixing with the active ingredient satisfies the above-mentioned disintegration index, and the effects of the present invention (making into a fine particle) attained.

Specific examples of the carrier include hydrophobic amino acids such as valine, leucine, isoleucine and phenylalanine, and salts and amides thereof; hydrophilic amino acids such as glycine, proline, alanine, arginine and glutamic acid, and salts and amides thereof; derivatives of amino acids; and dipeptides, tripeptides or the like having two or more of the same one or different ones of the above-mentioned amino acids, and salts and amides thereof. One of these can be used alone, or two or more can be used in combination. Here, examples of salts of the amino acid or peptide include salts with an alkali metal such as sodium or potassium or an alkaline earth metal such as calcium, and addition salts with an inorganic acid such as phosphoric acid or hydrochloric acid or an organic acid such as sulfonic acid, while examples of amides include L-leucine amide hydrochloride.

Moreover, an amino acid other than an α-amino acid can be used in as a carrier. Examples of such an amino acid include β-alanine, γ-aminobutyric acid, homoserine and taurine. Other examples of carriers include monosaccharides such as glucose; disaccharides such as saccharose, maltose, lactose and trehalose; sugar alcohols such as mannitol; oligosaccharides such as cyclodextrin; polysaccharides such as dextran 40 and pullulan; polyhydric alcohols such as polyethylene glycol; and fatty acid sodium salts such as sodium caprate. One of these carriers may be used alone, or two or more may be used in combination.

Of the above carriers, specific examples of carriers that are preferable for delivering the active ingredient efficiently into the lungs include hydrophobic amino acids such as isoleucine, valine, leucine and phenylalanine, and salts and amides thereof; hydrophobic dipeptides such as leucyl-valine, leucyl-phenylalanine and phenylalanyl-isoleucine; and hydrophobic tripeptides such as leucyl-leucyl-leucine and leucyl-leucyl-valine. Again, one of these may be used alone, or two or more may be used in combination.

There are no particular limitations on the proportion of the active ingredient(s) (drug(s)) mixed into the freeze-dried composition; nevertheless, examples of the content are 20 mg or less, preferably 10 mg or less, more preferably 5 mg or less, yet more preferably 2 mg or less, particularly preferably 1 mg or less.

Moreover, there are no particular limitations on the mixing proportion of the carrier(s), provided the final freeze-dried composition satisfies the above-mentioned disintegration index; nevertheless, as a guideline, per 100 wt % of the freeze-dried composition, the range is generally from 0.1 to less than 100 wt %, preferably from 1 to less than 100 wt %, more preferably from 10 to less than 100 wt %, particularly preferably from 20 to less than 100 wt %.

Note that, in addition to the above-mentioned components, the freeze-dried composition that is the subject of the present invention may have mixed therein various additives, for example for stabilizing the active ingredient(s) in solution before drying, for stabilizing the active ingredient(s) after drying, or for preventing the active ingredient(s) from sticking to the vessel, provided that the above-mentioned disintegration index is satisfied and the effects of the present invention are not impaired. For example, the freeze-dried composition may contain human serum albumin, inorganic salts, surfactants, buffering agents and so on. A wide range of surfactants can be used, regardless of whether they are anionic surfactants, cationic surfactants or nonionic surfactants, provided that they are surfactants that are generally used in medicines. Preferable examples are nonionic surfactants such as sorbitan trioleate and polyoxyethylene sorbitan fatty acid esters (for example Tween type surfactants).

The freeze-dried composition for use in the invention encompasses the specific embodiments defined in the following items 201 to 220:

201. A freeze-dried composition for transpulmonary administration having the following properties:
 (i) has a non-powder cake-like form,
 (ii) has a disintegration index of 0.015 or more, and
 (iii) becomes fine particles having a mean particle diameter of 10 microns or less or a fine particle fraction of 10% or more upon receipt of an air impact having an air speed of at least 1 m/sec and an air flow rate of at least 17 ml/sec.

202. The freeze-dried composition according to item 201, wherein the disintegration index is 0.02 or more.

203. The freeze-dried composition according to item 201, wherein the disintegration index is 0.015 to 1.5.

204. The freeze-dried composition according to item 201, becoming fine particles having a mean particle diameter of 10 microns or less or a fine particle fraction of 10% or more upon receipt of an air impact having an air speed of at least 2 m/sec and an air flow rate of at least 17 ml/sec.

205. The freeze-dried composition according to item 201, becoming fine particles having a mean particle diameter of 10 microns or less or a fine particle fraction of 10% or more upon receiving an air impact having an air speed in a range of 1 to 300 m/sec and an air flow rate of at least 17 ml/sec.

206. The freeze-dried composition according to item 201, becoming fine particles having a mean particle diameter of 10 microns or less or a fine particle fraction of 10% or more upon receipt of an air impact having an air speed of at least 1 m/sec and an air flow rate of at least 20 ml/sec.

207. The freeze-dried composition according to item 201, becoming fine particles having a mean particle diameter of 10 microns or less or a fine particle fraction of 10% or more upon receiving an air impact having an air speed of at least 1 m/sec and an air flow rate in a range of 17 ml/sec to 15 L/sec.

208. The freeze-dried composition according to item 201, becoming fine particles having a mean particle diameter of 5 microns or less or a fine particle fraction of 20% or more upon receiving an air impact.

209. The freeze-dried composition according to item 201, containing a synthetic low-molecular-weight drug as an active ingredient.

210. The freeze-dried composition according to item 201, containing a high-molecular-weight drug such as a protein, a peptide or the like as an active ingredient.

211. The freeze-dried composition according to item 209, containing a synthetic low-molecular-weight drug as the active ingredient, and at least one selected from the group consisting of amino acids, dipeptides, tripeptides, and saccharides as a carrier.

212. The freeze-dried composition according to item 210, containing a high-molecular-weight drug such as a protein, a peptide or the like as the active ingredient, and at least one selected from the group consisting of amino acids, dipeptides, tripeptides, and saccharides as a carrier.

213. The freeze-dried composition according to item 211, containing a synthetic low-molecular-weight drug as the active ingredient, and at least one selected from the group consisting of hydrophobic amino acids, hydrophobic dipeptides, and hydrophobic tripeptides as the carrier.

214. The freeze-dried composition according to item 212, characterized by containing a high-molecular-weight drug such as a protein, a peptide or the like as the active ingredient, and at least one selected from the group consisting of hydrophobic amino acids, hydrophobic dipeptides, and hydrophobic tripeptides as the carrier.

215. The freeze-dried composition according to item 201, being a water-soluble composition.

216. The freeze-dried composition according to item 201, containing a single dose of an active ingredient.

217. The freeze-dried composition according to item 201, being a freeze-dried composition for transpulmonary administration having the following properties:
(i) has a non-powder cake-like form,
(ii) has a disintegration index in a range of 0.015 to 1.5, and
(iii) becomes fine particles having a mean particle diameter of 10 microns or less or a fine particle fraction of 10% or more upon receiving an air impact having an air speed in a range of 1 to 300 m/sec and an air flow rate in a range of 17 ml/sec to 15 L/sec.

218. The freeze-dried composition according to item 217, wherein the disintegration index is 0.02 to 1.0.

219. The freeze-dried composition according to item 217, wherein the air speed is 1 to 250 m/sec.

220. The freeze-dried composition according to item 217, wherein the air flowrate is 20 ml/sec to 10 L/sec.

(3) Dry Powder Inhalation System for Transpulmonary Administration

The dry powder inhalation system for transpulmonary administration of the present invention is a system that combines a freeze-dried composition having a composition such that, by applying an air impact to the freeze-dried composition which exists in a non-powder form having been freeze-dried in a vessel and not subjected to processing such as pulverization, the freeze-dried composition can be made into fine particles having a mean particle diameter of 10 microns or less or a fine particle fraction of 10% or more in the vessel, and a inhaling device comprising prescribed means. According to this dry powder inhalation system for transpulmonary administration, a user him/herself can prepare the freeze-dried composition which has been provided in a non-powder form into a powdered preparation comprising fine particles having a mean particle diameter of 10 microns or less or a fine particle fraction of 10% or more, which is a preparation suitable for transpulmonary administration, at the time of use (the time of inhalation), and administer (take) the powdered preparation.

To obtain the effects of the dry powder inhalation system for transpulmonary administration effectively, it is important to select the composition of the freeze-dried composition, the inhaling device, the vessel and so on appropriately. As the inhaling device, it is preferable to adopt a device comprising ① means for applying an air impact (or means for introducing air) and ② means for discharging fine particles (or means for administering by inhalation), in which, by means for introducing air (means ①) air is introduced into (inflow) a vessel which houses the non-powder-form freeze-dried composition and the freeze-dried composition is pulverized into fine particles using the impact (jet pressure) of the air that has been introduced into (flowed into) the vessel, and then, using the means ② for discharging fine particles, the dried powder composition made into fine particles by means ① is discharged from the vessel. Then, the fine particles are directly administered to a user.

An example of such device is the dry powder inhaler of the invention mentioned earlier. Moreover, the freeze-dried composition mentioned earlier is a suitable example of a freeze-dried composition that can easily be made into fine particles through an air impact (jet pressure) of external air introduced into (flowing into) the vessel by the means for applying an air impact (means for introducing air) of the above-mentioned device.

The dry powder inhalation system suitable for transpulmonary administration according to the invention includes a vessel housing the freeze-dried composition of the invention and a dry powder inhaler of the invention used in combination at the time of inhalation. In other words, the dry powder inhalation system of the invention, at least when used for inhalation, comprises the vessel housing the freeze-dried composition of the invention and the dry powder inhaler of the invention.

According to the system of the invention, by introducing air into the vessel using the dry powder inhaler for applying an air impact having an air speed of at least 1 m/sec and an air flow rate of at least 17 ml/sec to the freeze-dried composition in the vessel, a dry powdered preparation having a particle size suitable for transpulmonary administration can be obtained. Furthermore, the system allows transpulmonary administration of the obtained dry powdered preparation directly to a user by inhalation. Therefore, the dry powder inhalation system for transpulmonary administration of the invention is a system for producing a dry powdered preparation suitable for transpulmonary administration and, at the same time, a system for transpulmonarily administering the dry powder preparation to a user.

The dry powder inhalation system for transpulmonary administration of the invention encompasses the specific embodiments defined in the following items 301 to 322:

301. A dry powder inhalation system for transpulmonary administration, using a combination of:
(1) a vessel housing a freeze-dried composition that contains a single dose of an active ingredient, and has:
(i) a non-powder cake-like form,
(ii) a disintegration index of 0.015 or more, and
(iii) a property of becoming fine particles having a mean particle diameter of 10 microns or less or a fine particle fraction of 10% or more upon receiving an air impact having an air speed of at least 1 m/sec and an air flow rate of at least 17 ml/sec; and
(2) a device comprising means capable of applying said air impact to the freeze-dried composition in said vessel, and means for discharging the powder-form freeze-dried composition that has been made into fine particles.

302. The dry powder inhalation system for transpulmonary administration according to item 301, wherein the vessel and the device are used in combination at the time of inhalation.

303. The dry powder inhalation system for transpulmonary administration according to item 301, wherein the disintegration index of the freeze-dried composition is 0.02 or more.

304. The dry powder inhalation system for transpulmonary administration according to item 301, wherein the disintegration index of the freeze-dried composition is in a range of 0.015 to 1.5.

305. The dry powder inhalation system for transpulmonary administration according to item 301, wherein the air impact of (iii) is generated by air having an air speed of at least 2 m/sec and an air flow rate of at least 17 ml/sec.

306. The dry powder inhalation system for transpulmonary administration according to item 301, wherein the air impact of (iii) is generated by air having an air speed in a range of 1 to 300 m/sec and an air flow rate of at least 17 ml/sec.

307. The dry powder inhalation system for transpulmonary administration according to item 301, wherein the air impact of (iii) is generated by air having an air speed of at least 1 m/sec and an air flow rate of at least 20 ml/sec.

308. The dry powder inhalation system for transpulmonary administration according to item 301, wherein the air impact of (iii) is generated by air having an air speed of at least 1 m/sec and an air flow rate in a range of 17 ml/sec to 15 L/sec.

309. The dry powder inhalation system for transpulmonary administration according to item 301, wherein the freeze-dried composition has a property of becoming fine particles having a mean particle diameter of 5 microns or less or a fine particle fraction of 20% or more upon receipt of an air impact.

310. The dry powder inhalation system for transpulmonary administration according to item 301, wherein the freeze-dried composition contains a synthetic low-molecular-weight drug as the active ingredient.

311. The dry powder inhalation system for transpulmonary administration according to item 301, wherein the freeze-dried composition contains a high-molecular-weight drug such as a protein, a peptide or the like as the active ingredient.

312. The dry powder inhalation system for transpulmonary administration according to item 310, wherein the freeze-dried composition contains a synthetic low-molecular-weight drug as the active ingredient, and at least one selected from the group consisting of amino acids, dipeptides, tripeptides, and saccharides as a carrier.

313. The dry powder inhalation system for transpulmonary administration according to item 311, wherein the freeze-dried composition contains a high-molecular-weight drug such as a protein, a peptide or the like as the active ingredient, and at least one selected from the group consisting of amino acids, dipeptides, tripeptides, and saccharides as a carrier.

314. The dry powder inhalation system for transpulmonary administration according to item 312, wherein the freeze-dried composition contains a synthetic low-molecular-weight drug as the active ingredient, and at least one selected from the group consisting of hydrophobic amino acids, hydrophobic dipeptides, and hydrophobic tripeptides as the carrier.

315. The dry powder inhalation system for transpulmonary administration according to item 313, wherein the freeze-dried composition contains a high-molecular-weight drug such as a protein, a peptide or the like as the active ingredient, and at least one selected from the group consisting of hydrophobic amino acids, hydrophobic dipeptides, and hydrophobic tripeptides as the carrier.

316. The dry powder inhalation system for transpulmonary administration according to item 301, wherein the freeze-dried composition is a water-soluble composition.

317. The dry powder inhalation system for transpulmonaty administration according to item 301, wherein the device is:
i) a dry powder inhaler for transpulmonary administration, being a device used for making a freeze-dried composition that has been housed in non-powder form in a vessel into fine particles, and administering the resulting fine particles to a user by inhalation,
comprising a needle part having an air jet flow path, a needle part having a discharge flow path, air pressure-feeding means for feeding air into the air jet flow path of said needle part, and an inhalation port that communicates with the discharge flow path of said needle part,
and characterized by being constituted such that a stopper that seals up said vessel is pierced by said needle parts, thus communicating the air jet flow path and the discharge flow path with the inside of said vessel, and air is jetted into said vessel through said air jet flow path using said air pressure-feeding means, thus pulverizing said freeze-dried composition into fine particles by the impact of the jetted air, and discharging the fine particles obtained from the inhalation port via said discharge flow path, or
ii) a dry powder inhaler for transpulmonary administration, being a device used for making a freeze-dried composition that has been housed in non-powder form in a vessel into fine particles, and administering the resulting fine particles to a user by inhalation,
comprising a needle part having a suction flow path, a needle part having an air introduction flow path, and an inhalation port that communicates with said suction flow path,
and characterized by being constituted such that, in a state in which a stopper sealing up said vessel has been pierced by said needle parts, through the inhalation pressure of the user, air in said vessel is inhaled from said inhalation port, and at the same time outside air flows into said vessel, at a negative pressure, through said air introduction flow path, and as a result said freeze-dried composition is pulverized into fine particles by the impact of the air flowing in, and the fine particles obtained are discharged from the inhalation port through said suction flow path.

318. The dry powder inhalation system for transpulmonary administration according to item 317, as the device, using the dry powder inhaler comprising:

a holder part for holding a vessel that is sealed up with a stopper and houses a freeze-dried composition in a non-powder cake-like form that will be made into fine particles upon receiving an air impact, means for applying an air impact to said freeze-dried composition in said vessel, and sucking said freeze-dried composition in a powder-form that has been made into fine particles by the air impact out from said vessel, a needle part having a suction flow path for sucking said freeze-dried composition out from said vessel, and an air introduction flow path for introducing outside air into said vessel, a suction port that communicates with said suction flow path of said needle part, a guide part for guiding said holder part in the axial direction of said needle part, a holder operating part that has a mechanism part for, when said vessel is held by said holder part, advancing the vessel towards a needle tip of said needle part to pierce the stopper of the vessel with said needle tip, and retreating the vessel from said needle tip to separate the stopper of the vessel from said needle tip, and an operator that operates the mechanism part, and is constituted such that said operating member can be operated with a force smaller than the force necessary for the mechanism part to pierce the stopper of the vessel with said needle part, and a housing that supports said needle part and is for providing said suction port, said guide part and said holder operating part, and constituted such that, in a state in which said stopper has been pierced by said needle part to communicate the suction flow path and the air introduction flow path of said needle part with the inside of said vessel and position the tip of the air introduction flow path at said freeze-dried composition, through the inhalation pressure of a user, air in said vessel is inhaled from said suction port, and air is made to flow into said vessel through the air introduction flow path, thus applying an air impact to the freeze-dried composition in said vessel.

319. The dry powder inhalation system for transpulmonary administration according to item 301, using a combination of:

(1) a vessel housing a freeze-dried composition that contains a single dose of an active ingredient, and has:
 (i) a non-powder cake-like form,
 (ii) a disintegration index in a range of 0.015 to 1.5, and
 (iii) a property of becoming fine particles having a mean particle diameter of 10 microns or less or a fine particle fraction of 10% or more upon receipt of an air impact having an air speed in a range of 1 to 300 m/sec and an air flow rate in a range of 17 ml/sec to 15 L/sec; and (2) a device comprising means capable of applying said air impact to the freeze-dried composition in said vessel, and means for discharging the powder-form freeze-dried composition that has been made into fine particles.

320. The dry powder inhalation system for transpulmonary administration according to item 319, wherein the disintegration index is 0.02 to 1.0.

321. The dry powder inhalation system for transpulmonary administration according to item 319, wherein the air speed is 1 to 250 m/sec.

322. The dry powder inhalation system for transpulmonary administration according to item 319, wherein the air flow rate is 20 ml/sec to 10 L/sec.

(4) Method of Manufacturing a Dry Powdered Preparation

Moreover, the present invention relates to a method of manufacturing a dry powdered preparation comprising fine particles with a particle diameter suitable for transpulmonary administration (dry powdered preparation for transpulmonary administration) by inhalation, by making a freeze-dried composition that has been housed in a non-powder form in a vessel into fine particles. The manufacturing method can be implemented in the vessel housing the non-powder form freeze-dried composition by applying a predetermined air impact. Specifically, the method of manufacturing the dry powder preparation of the invention can be carried out by applying an air impact having an air speed of at least 1 m/sec and an air flow rate of at least 17 ml/sec to the above-mentioned non-powder form freeze-dried composition of the invention. Thereby, the non-powder form freeze-dried composition can be made into a dry powdered preparation having a mean particle diameter of 10 microns or less, preferably 5 microns or less or a fine particle fraction of 10% or more, preferably 20% or more, more preferably 25% or more, and still more preferably 30% or more. The method of applying the air impact to the freeze-dried composition is, not limited; however, the above-mentioned dry powder inhaler of the invention is preferably used.

It is preferable that the manufacturing method be implemented by introducing air capable of applying the above-described air impact to a freeze-dried composition into the vessel housing a non-powder freeze-dried composition. The method of manufacturing the dry powdered preparation of the invention is characterized in that a patient administering the dry powdered preparation can prepare by him/herself the powdered preparation at the time of use (inhalation) by making the freeze-dried composition housed in a vessel into fine particles having a particle diameter suitable for transpulmonary administration.

The method of manufacturing a dry powdered preparation of the invention encompasses the specific embodiments defined in the following items 401 to 424:

401. A method of manufacturing a dry powdered preparation for transpulmonary administration, comprising:

introducing air into a vessel to apply to a freeze-dried composition an air impact having an air speed of at least 1 m/sec and an air flow rate of at least 17 ml/sec using a device capable of applying said air impact to the freeze-dried composition in the vessel, thereby making said freeze-dried composition into fine particles having a mean particle diameter of 10 microns or less or a fine particle fraction of 10% or more;

the freeze-dried composition containing a single dose of an active ingredient and having the following properties:
 (i) has a non-powder cake-like form,
 (ii) has a disintegration index of 0.015 or more, and
 (iii) becomes fine particles having a mean particle diameter of 10 microns or less or a fine particle fraction of 10% or more upon receipt of the air impact.

402. The method of manufacturing a dry powdered preparation for transpulmonary administration according to item 401, wherein the fine particles prepared have a mean particle diameter of 5 microns or less or a fine particle fraction of 20% or more.

403. The method of manufacturing a dry powdered preparation for transpulmonary administration according to item 401, wherein the disintegration index of the freeze-dried composition is 0.02 or more.

404. The method of manufacturing a dry powdered preparation for transpulmonary administration according to item 401, wherein the disintegration index of the freeze-dried composition is in a range of 0.015 to 1.5.

405. The method of manufacturing a dry powdered preparation for transpulmonary administration according to item 401, wherein the freeze-dried composition contains a synthetic low-molecular-weight drug as the active ingredient.

406. The method of manufacturing a dry powdered preparation for transpulmonary administration according to item 401, wherein the freeze-dried composition contains a high-molecular-weight drug such as a protein, a peptide or the like as the active ingredient.

407. The method of manufacturing a dry powdered preparation for transpulmonary administration according to item 405, wherein the freeze-dried composition contains a synthetic low-molecular-weight drug as the active ingredient, and at least one selected from the group consisting of amino acids, dipeptides, tripeptides, and saccharides as a carrier.

408. The method of manufacturing a dry powdered preparation for transpulmonary administration according to item 406, wherein the freeze-dried composition contains a high-molecular-weight drug such as a protein, a peptide or the like as the active ingredient, and at least one selected from the group consisting of amino acids, dipeptides, tripeptides, and saccharides as a carrier.

409. The method of manufacturing a dry powdered preparation for transpulmonary administration according to item 407, wherein the freeze-dried composition contains a synthetic low-molecular-weight drug as the active ingredient, and at least one selected from the group consisting of hydrophobic amino acids, hydrophobic dipeptides, and hydrophobic tripeptides as the carrier.

410. The method of manufacturing a dry powdered preparation for transpulmonary administration according to item 408, wherein the freeze-dried composition contains a high-molecular-weight drug such as a protein, a peptide or the like as the active ingredient, and at least one selected from the group consisting of hydrophobic amino acids, hydrophobic dipeptides, and hydrophobic tripeptides as the carrier.

411. The method of manufacturing a dry powdered preparation for transpulmonary administration according to item 401, wherein the freeze-dried composition is a water-soluble composition.

412. The method of manufacturing a dry powdered preparation for transpulmonary administration according to item 401, being a method of making the freeze-dried composition into fine particles in a vessel having a volume of 0.2 to 50 ml.

413. The method of manufacturing a dry powdered preparation for transpulmonary administration according to item 401, carried out by using a device having means capable of applying an air impact having an air speed of at least 2 m/sec and an air flow rate of at least 17 ml/sec to the freeze-dried composition in the vessel, and introducing air having the air impact into the vessel housing the freeze-dried composition.

414. The method of manufacturing a dry powdered preparation for transpulmonary administration according to item 401, carried out by using a device having means capable of applying an air impact having an air speed in a range of 1 to 300 m/sec and an air flow rate of at least 17 ml/sec to the freeze-dried composition in the vessel, and introducing air having the air impact into the vessel housing the freeze-dried composition.

415. The method of manufacturing a dry powdered preparation for transpulmonary administration according to item 401, carried out by using a device having means capable of applying an air impact having an air speed of at least 1 m/sec and an air flow rate of at least 20 ml/sec to the freeze-dried composition in the vessel, and introducing air having the air impact into the vessel housing the freeze-dried composition.

416. The method of manufacturing a dry powdered preparation for transpulmonary administration according to item 401, carried out by using a device having means capable of applying an air impact having an air speed of at least 1 m/sec and an air flow rate in a range of 17 ml/sec to 15 L/sec to the freeze-dried composition in the vessel, and introducing air having the air impact into the vessel housing the freeze-dried composition.

417. The method of manufacturing a dry powdered preparation for transpulmonary administration according to item 401, characterized by making the freeze-dried composition into fine particles using the dry powder inhaler of item 101 or 102 shown in the section of (1) Dry powder inhaler as the device.

418. The method of manufacturing a powdered preparation for transpulmonary administration according to item 417, characterized by making the freeze-dried composition into fine particles using the dry powder inhaler according to item 109 shown in the section of (1) Dry powder inhaler as the device.

419. The method of manufacturing a powdered preparation for transpulmonary administration according to item 417, being a method of manufacturing a dry powdered preparation in which the freeze-dried composition is made into fine particles using the dry powder inhaler according to item 101 shown in the section of (1) Dry powder inhaler, wherein the amount of air jetted into said vessel each time using the dry powder inhaler is 5 to 100 ml.

420. The method of manufacturing a powdered preparation for transpulmonary administration according to item 417, being a method of manufacturing a dry powdered preparation in which the freeze-dried composition is made into fine particles using the dry powder inhaler of item 102 shown in the section of (1) Dry powder inhaler, wherein the flow rate of air inhalation from the inhalation port using the dry powder inhaler is 5 to 300 L/min.

421. The method of manufacturing a dry powdered preparation for transpulmonary administration according to item 401, comprising:

introducing air into a vessel to apply to a freeze-dried composition an air impact having an air speed in a range of 1 to 300 m/sec and an air flow rate in a range of 17 ml/sec to 15 L/sec using a device capable of applying said air impact to the freeze-dried composition in the vessel, thereby making said freeze-dried composition into fine particles having a mean particle diameter of 10 microns or less or a fine particle fraction of 10% or more;

the freeze-dried composition containing a single dose of an active ingredient and having the following properties:
  (i) has a non-powder cake-like form,
  (ii) has a disintegration index in a range of 0.015 to 1.5, and
  (iii) becomes fine particles having a mean particle diameter of 10 microns or less or a fine particle fraction of 10% or more upon receipt of the air impact.

422. The method of manufacturing a dry powdered preparation for transpulmonary administration according to item 421, wherein the disintegration index is 0.02 to 1.0.

423. The method of manufacturing a dry powdered preparation for transpulmonary administration according to item 421, wherein the air speed is 1 to 250 m/sec.

424. The method of manufacturing a dry powdered preparation for transpulmonary administration according to item 421, wherein the air flow rate is 20 ml/sec to 10 L/sec.

(5) Transpulmonary Administration Method

The present invention further provides a transpulmonary administration method comprising making a freeze-dried composition in a non-powder form into fine particles suitable for transpulmonary administration at the time of usage (administration), and administering the resulting preparation in a powder form with fine particles by inhalation. The transpulmonary administration method can be carried out using the above-described dry powder inhalation system for transpulmonary administration of the invention comprising the vessel housing the freeze-dried composition of the invention and the dry powder inhaler of the invention.

The transpulmonary administration method of the invention encompasses the specific embodiments defined in the following items 501 to 522:

501. A transpulmonary administration method comprising:
making a freeze-dried composition into fine particles having a mean particle diameter of 10 microns or less or a fine particle fraction of 10% or more by applying an air impact having an air speed of at least 1 m/sec and an air flow rate of at least 17 ml/sec to the freeze-dried composition at the time of use, and
administering the resulting fine particle powder to a user by inhalation;
the freeze-dried composition containing a single dose of an active ingredient and having the following properties:
(i) has a non-powder cake-like form,
(ii) has a disintegration index of 0.015 or more, and
(iii) becomes fine particles having a mean particle diameter of 10 microns or less or a fine particle fraction of 10% or more upon receipt of the air impact.

502. The transpulmonary administration method according to item 501, wherein the freeze-dried composition is housed in a vessel, and the fine particle powder are made using a device comprising means capable of applying the air impact to the freeze-dried composition in the vessel and means for discharging the resulting fine particle powder-form freeze-dried composition out of the vessel.

503. The transpulmonary administration method according to item 502, wherein the disintegration index of the freeze-dried composition is 0.02 or more.

504. The transpulmonary administration method according to item 502, wherein the disintegration index of the freeze-dried composition is in a range of 0.015 to 1.5.

505. The transpulmonary administration method according to item 502, wherein the air impact of (iii) is generated by air having an air speed of at least 2 m/sec and an air flow rate of at least 17 ml/sec.

506. The transpulmonary administration method according to item 502, wherein the air impact of (iii) is generated by air having an air speed in a range of 1 to 300 m/sec and an air flow rate of at least 17 ml/sec.

507. The transpulmonary administration method according to item 502, wherein the air impact of (iii) is generated by air having an air speed of at least 1 m/sec and an air flow rate of at least 20 ml/sec.

508. The transpulmonary administration method according to item 502, wherein the air impact of (iii) is generated by air having an air speed of at least 1 m/sec and an air flow rate in a range of 17 ml/sec to 15 L/sec.

509. The transpulmonary administration method according to item 502, wherein the freeze-dried composition contains a synthetic low-molecular-weight drug as the active ingredient.

510. The transpulmonary administration method according to item 502, wherein the freeze-dried composition contains a high-molecular-weight drug such as a protein, a peptide or the like as the active ingredient.

511. The transpulmonary administration method according to item 509, wherein the freeze-dried composition contains a synthetic low-molecular-weight drug as the active ingredient, and at least one selected from the group consisting of amino acids, dipeptides, tripeptides, and saccharides as a carrier.

512. The transpulmonary administration method according to item 510, wherein the freeze-dried composition contains a high-molecular-weight drug such as a protein, a peptide or the like as the active ingredient, and at least one selected from the group consisting of amino acids, dipeptides, tripeptides, and saccharides as a carrier.

513. The transpulmonary administration method according to item 511, wherein the freeze-dried composition contains a synthetic low-molecular-weight drug as the active ingredient, and at least one selected from the group consisting of hydrophobic amino acids, hydrophobic dipeptides, and hydrophobic tripeptides as the carrier.

514. The transpulmonary administration method according to item 512, wherein the freeze-dried composition contains a high-molecular-weight drug such as a protein, a peptide or the like as the active ingredient, and at least one selected from the group consisting of hydrophobic amino acids, hydrophobic dipeptides, and hydrophobic tripeptides as the carrier.

515. The transpulmonary administration method according to item 502, wherein the freeze-dried composition is a water-soluble composition.

516. The transpulmonary administration method according to item 502, being a method of making into fine particles and administering such that the fine particles have a mean particle diameter of 5 microns or less or a fine particle fraction of 20% or more.

517. The transpulmonary administration method according to item 502, using the dry powder inhaler of item 101 or 102 shown in the section of (1) Dry powder inhaler as the device.

518. The transpulmonary administration method according to item 517, using the dry powder inhaler of item 109 shown in the section of (1) Dry powder inhaler as the device.

519. The transpulmonary administration method according to item 502, wherein the freeze-dried composition has the following properties:
(i) has a non-powder cake-like form,
(ii) has a disintegration index in a range of 0.015 to 1.5, and
(iii) becomes fine particles having a mean particle diameter of 10 microns or less or a fine particle fraction of 10% or more upon receiving an air impact having an air speed in a range of 1 to 300 m/sec and an air flow rate in a range of 17 ml/sec to 15 L/sec,
and the fine particles are made using a dry powder inhaler comprising means capable of applying said air impact to the freeze-dried composition in the vessel and means for discharging the resulting fine particle powder-form freeze-dried composition out of the vessel.

520. The transpulmonary administration method according to item 519, wherein the disintegration index is 0.02 to 1.0.

521. The transpulmonary administration method according to item 519, wherein the air speed is 1 to 250 m/sec.

522. The transpulmonary administration method according to item 519, wherein the air flow rate is 20 ml/sec to 10 L/sec.

(6) Use of a Freeze-Dried Composition for Transpulmonary Administration by Inhalation The present invention also provides use of a freeze-dried composition in a non-powder form for the transpulmonary administration by inhalation. The use encompasses the specific embodiments defined in the following items 601 to 622:

601. Use of a freeze-dried composition for transpulmonary administration by inhalation,
the freeze-dried composition containing a single dose of an active ingredient and having the following properties:
  (i) has a non-powder cake-like form,
  (ii) has a disintegration index of 0.015 or more, and
  (iii) becomes fine particles having a mean particle diameter of 10 microns or less or a fine particle fraction of 10% or more upon receipt of an air impact having an air speed of at least 1 m/sec and an air flow rate of at least 17 ml/sec,
and being used by forming into fine particles having said mean particle diameter or said fine particle fraction.

602. The use of a freeze-dried composition for transpulmonary administration according to item 601, wherein the freeze-dried composition is housed in a vessel, and the fine particles are made using a device comprising means capable of applying the air impact to the freeze-dried composition in the vessel and means for discharging the resulting fine particle powder-form freeze-dried composition out of the vessel.

603. The use of a freeze-dried composition for transpulmonary administration according to item 602, wherein the disintegration index of the freeze-dried composition is 0.02 or more.

604. The use of a freeze-dried composition for transpulmonary administration according to item 602, wherein the disintegration index of the freeze-dried composition is in a range of 0.015 to 1.5.

605. The use of a freeze-dried composition for transpulmonary administration according to item 602, wherein the freeze-dried composition becomes fine particles having a mean particle diameter of 10 microns or less or a fine particle fraction of 10% or more upon receiving an air impact having an air speed of at least 2 m/sec and an air flow rate of at least 17 ml/sec.

606. The use of a freeze-dried composition for transpulmonary administration according to item 602, wherein the freeze-dried composition becomes fine particles having a mean particle diameter of 10 microns or less or a fine particle fraction of 10% or more upon receiving an air impact having an air speed in a range of 1 to 300 m/sec and an air flow rate of at least 17 ml/sec.

607. The use of a freeze-dried composition for transpulmonary administration according to item 602, wherein the freeze-dried composition becomes fine particles having a mean particle diameter of 10 microns or less or a fine particle fraction of 10% or more upon receiving an air impact having an air speed of at least 1 m/sec and an air flow rate of at least 20 ml/sec.

608. The use of a freeze-dried composition for transpulmonary administration according to item 602, wherein the freeze-dried composition becomes fine particles having a mean particle diameter of 10 microns or less or a fine particle fraction of 10% or more upon receiving an air impact having an air speed of at least 1 m/sec and an air flow rate in a range of 17 ml/sec to 15 L/sec.

609. The use of a freeze-dried composition for transpulmonary administration according to item 602, wherein the freeze-dried composition becomes fine particles having a mean particle diameter of 5 microns or less or a fine particle fraction of 20% or more upon receiving an air impact.

610. The use of a freeze-dried composition for transpulmonary administration according to item 602, wherein the freeze-dried composition contains a synthetic low-molecular-weight drug as the active ingredient.

611. The use of a freeze-dried composition for transpulmonary administration according to item 602, wherein the freeze-dried composition contains a high-molecular-weight drug such as a protein, a peptide or the like as the active ingredient.

612. The use of a freeze-dried composition for transpulmonary administration according to item 610, wherein the freeze-dried composition contains a synthetic low-molecular-weight drug as the active ingredient, and at least one selected from the group consisting of amino acids, dipeptides, tripeptides, and saccharides as a carrier.

613. The use of a freeze-dried composition for transpulmonary administration according to item 611, wherein the freeze-dried composition contains a high-molecular-weight drug such as a protein, a peptide or the like as the active ingredient, and at least one selected from the group consisting of amino acids, dipeptides, tripeptides, and saccharides as a carrier.

614. The use of a freeze-dried composition for transpulmonary administration according to item 612, wherein the freeze-dried composition contains a synthetic low-molecular-weight drug as the active ingredient, and at least one selected from the group consisting of hydrophobic amino acids, hydrophobic dipeptides, and hydrophobic tripeptides as the carrier.

615. The use of a freeze-dried composition for transpulmonary administration according to item 613, wherein the freeze-dried composition contains a high-molecular-weight drug such as a protein, a peptide or the like as the active ingredient, and at least one selected from the group consisting of hydrophobic amino acids, hydrophobic dipeptides, and hydrophobic tripeptides as the carrier.

616. The use of a freeze-dried composition for transpulmonary administration according to item 602, wherein the freeze-dried composition is a water-soluble composition.

617. The use of a freeze-dried composition for transpulmonary administration according to item 602, using the dry powder inhaler of item 101 or 102 shown in the section of (1) Dry powder inhaler as the device.

618. The use of a freeze-dried composition for transpulmonary administration according to item 617, using the dry powder inhaler of item 109 shown in the section of (1) Dry powder inhaler as the device.

619. The use of a freeze-dried composition for transpulmonary administration according to item 602, wherein the freeze-dried composition has the following properties:

(i) has a non-powder cake-like form, (ii) has a disintegration index in a range of 0.015 to 1.5, and (iii) becomes fine particles having a mean particle diameter of 10 microns or less or a fine particle fraction of 10% or more upon receipt of an air impact having an air speed in a range of 1 to 300 m/sec and an air flow rate in a range of 17 ml/sec to 15 L/sec, and the fine particles are made using a device comprising means capable of applying the air impact to the freeze-dried composition in the vessel and means for discharging the resulting fine particle powder-form freeze-dried composition out of the vessel.

620. The use of a freeze-dried composition in transpulmonary administration according to item 619, wherein the disintegration index is 0.02 to 1.0.

621. The use of a freeze-dried composition in transpulmonary administration according to item 619, wherein the air speed is 1 to 250 m/sec.

622. The use of a freeze-dried composition in transpulmonary administration according to item 619, wherein the air flow rate is 20 ml/sec to 10 L/sec.

(7) Use of a Freeze-Dried Composition for Manufacture of a Dry Powdered Preparation for Transpulmonary Administration by Inhalation Furthermore, the present invention provides use of a freeze-dried composition in a non-powder form for manufacture of a dry powdered preparation for transpulmonary administration by inhalation. The use encompasses the specific embodiments defined in the following items 701 to 723:

701. Use of a freeze-dried composition for manufacture of a dry powdered preparation for transpulmonary administration by inhalation, the freeze-dried composition having the following properties:
  (i) has a non-powder cake-like form,
  (ii) has a disintegration index of 0.015 or more, and
  (iii) becomes fine particles having a mean particle diameter of 10 microns or less or a fine particle fraction of 10% or more upon receipt of an air impact having an air speed of at least 1 m/sec and an air flow rate of at least 17 ml/sec,
and being used by forming into fine particles having said mean particle diameter or said fine particle fraction at the time of use.

702. The use of a freeze-dried composition for manufacture of a dry powdered preparation for transpulmonary administration according to item 701, wherein the disintegration index of the freeze-dried composition is 0.02 or more.

703. The use of a freeze-dried composition for manufacture of a dry powdered preparation for transpulmonary administration according to item 701, wherein the disintegration index of the freeze-dried composition is in a range of 0.015 to 1.5.

704. The use of a freeze-dried composition for manufacture of a dry powdered preparation for transpulmonary administration according to item 701, wherein the freeze-dried composition becomes fine particles having a mean particle diameter of 10 microns or less or a fine particle fraction of 10% or more upon receipt of an air impact having an air speed of at least 2 m/sec and an air flow rate of at least 17 ml/sec.

705. The use of a freeze-dried composition for manufacture of a dry powdered preparation for transpulmonary administration according to item 701, wherein the freeze-dried composition becomes fine particles having a mean particle diameter of 10 microns or less or a fine particle fraction of 10% or more upon receipt of an air impact having an air speed in a range of 1 to 300 m/sec and an air flow rate of at least 17 ml/sec.

706. The use of a freeze-dried composition for manufacture of a dry powdered preparation for transpulmonary administration according to item 701, wherein the freeze-dried composition becomes fine particles having a mean particle diameter of 10 microns or less or a fine particle fraction of 10% or more upon receipt of an air impact having an air speed of at least 1 m/sec and an air flow rate of at least 20 ml/sec.

707. The use of a freeze-dried composition for manufacture of a dry powdered preparation for transpulmonary administration according to item 701, wherein the freeze-dried composition becomes fine particles having a mean particle diameter of 10 microns or less or a fine particle fraction of 10% or more upon receipt of an air impact having an air speed of at least 1 m/sec and an air flow rate in a range of 17 ml/sec to 15 L/sec.

708. The use of a freeze-dried composition for manufacture of a dry powdered preparation for transpulmonary administration according to item 701, wherein the freeze-dried composition becomes fine particles having a mean particle diameter of 5 microns or less or a fine particle fraction of 20% or more upon receipt of an air impact.

709. The use of a freeze-dried composition for manufacture of a dry powdered preparation for transpulmonary administration according to item 701, wherein the freeze-dried composition contains a synthetic low-molecular-weight drug as an active ingredient.

710. The use of a freeze-dried composition for manufacture of a dry powdered preparation for transpulmonary administration according to item 701, wherein the freeze-dried composition contains a high-molecular-weight drug such as a protein, a peptide or the like as an active ingredient.

711. The use of a freeze-dried composition for manufacture of a dry powdered preparation for transpulmonary administration according to item 709, wherein the freeze-dried composition contains a synthetic low-molecular-weight drug as the active ingredient, and at least one selected from the group consisting of amino acids, dipeptides, tripeptides, and saccharides as a carrier.

712. The use of a freeze-dried composition for manufacture of a dry powdered preparation for transpulmonary administration according to item 710, wherein the freeze-dried composition contains a high-molecular-weight drug such as a protein, a peptide or the like as the active ingredient, and at least one selected from the group consisting of amino acids, dipeptides, tripeptides, and saccharides as a carrier.

713. The use of a freeze-dried composition for manufacture of a dry powdered preparation for transpulmonary administration according to item 711, wherein the freeze-dried composition contains a synthetic low-molecular-weight drug as the active ingredient, and at least one selected from the group consisting of hydrophobic amino acids, hydrophobic dipeptides, and hydrophobic tripeptides as the carrier.

714. The use of a freeze-dried composition for manufacture of a dry powdered preparation for transpulmonary administration according to item 712, wherein the freeze-dried composition contains a high-molecular-weight drug such as a protein, a peptide or the like as the active ingredient, and at least one selected from the group consisting of hydrophobic amino acids, hydrophobic dipeptides, and hydrophobic tripeptides as the carrier.

715. The use of a freeze-dried composition for manufacture of a dry powdered preparation for transpulmonary administration according to item 701, wherein the freeze-dried composition is a water-soluble composition.

716. The use of a freeze-dried composition for manufacture of a dry powdered preparation for transpulmonary administration according to item 701, wherein the mean particle diameter of the fine particles of the powdered preparation for transpulmonary administration is 5 microns or less or the fine particle fraction of the fine particles is 20% or more.

717. The use of a freeze-dried composition for manufacture of a dry powdered preparation for transpulmonary administration according to item 701, wherein the freeze-dried composition is housed in a vessel, and the fine particles are prepared by using a device comprising means for applying a prescribed air impact to the freeze-dried composition housed in the vessel and means for discharging the resulting fine particle powder form freeze-dried composition out of the vessel.

718. The use of a freeze-dried composition for manufacture of a dry powdered preparation for transpulmonary administration of item 717, using the dry powder inhaler according to item 101 or 102 shown in the section of (1) Dry powder inhaler as the device.

719. The use of a freeze-dried composition for manufacture of a dry powdered preparation for transpulmonary administration according to item 718, using the dry powder inhaler of item 109 shown in the section of (1) Dry powder inhaler as the device.

720. The use of a freeze-dried composition for manufacture of a dry powdered preparation for transpulmonary administration according to item 701, using the freeze-dried composition having the following properties:
(i) has a non-powder cake-like form,
(ii) has a disintegration index in a range of 0.015 to 1.5, and
(iii) becomes fine particles having a mean particle diameter of 10 microns or less or a fine particle fraction of 10% or more upon receiving an air impact having an air speed in a range of 1 to 300 m/sec and an air flow rate in a range of 17 ml/sec to 15 L/sec.

721. The use of a freeze-dried composition for manufacture of a powdered preparation for transpulmonary administration according to item 720, wherein the disintegration index is 0.02 to 1.0.

722. The use of a freeze-dried composition for manufacture of a powdered preparation for transpulmonary administration according to item 720, wherein the air speed is 1 to 250 m/sec.

723. The use of a freeze-dried composition for manufacture of a powdered preparation for transpulmonary administration according to item 720, wherein the air flow rate is 20 ml/sec to 10 L/sec.

EXAMPLES

Following is a detailed description of the present invention, citing examples; however, the present invention is not limited to these examples.

In the following examples, the disintegration index of the non-powder-form freeze-dried composition (freeze-dried cake) of the present invention, and the fine particle fraction (%), which is an indicator for evaluating the delivery into the lungs of the dry powdered preparation produced, were calculated in accordance with the following methods.

<Calculation of Disintegration Index>

1.0 ml of n-hexane is instilled gently down the wall of the vessel into the prepared non-powder-form freeze-dried composition (freeze-dried cake), and agitation is carried out for about 10 seconds at 3000 rpm using an Automatic Lab-Mixer NS-8 (made by Pasolina). The mixture obtained is put into a UV cell (made by Shimadzu GLC Center) of optical path length 1 mm and optical path width 10 mm, and then the turbidity of the mixture is measured immediately at a measurement wavelength of 500 nm using a spectrophotometer (UV-240, made by Shimadzu Corporation). The value obtained by dividing the turbidity obtained by the total formulation amount (the total amount (weight) of the active ingredient and the carrier) is taken as the disintegration index.

<Calculation of Fine Particle Fraction>

A vessel filled with the prepared non-powder-form freeze-dried composition is installed into the dry powder inhaler, and using the device a prescribed air impact is applied on the composition, and the fine powdered preparation thus produced is discharged directly into apparatus A (a twin impinger: made by Copley, UK) as mentioned in the European Pharmacopoeia (Third Edition Supplement 2001, p 113-115). After this, the solvents in stage 1 and stage 2 of the apparatus are respectively collected, and the active ingredient contained in each solvent in the stage 1 or stage 2 is assayed using an appropriate method in accordance with the type of active ingredient in the freeze-dried composition, for example a bioassay method or HPLC (see the report of Lucas et al. (Pharm. Res., 15 (4), 562-569 (1998)) and the report of Iida et al. (Yakugaku Zasshi, 119 (10), 752-762 (1999)). The fraction that can be expected to be delivered into the lungs is that in stage 2 (the aerodynamic diameter of particles recovered in this fraction is 6.4 μm or less); the proportion of the active ingredient that reaches stage 2 and is recovered here is generally called the fine particle fraction (the amount that can be expected to reach the lungs), and is taken as a yardstick for evaluating the suitability as an inhalation for transpulmonary administration.

In the Examples and Comparative Examples given below, the active ingredients contained in stage 1 and stage 2 were quantitated, and the weight amount of the active ingredient in stage 2 was divided by the total weight amount of the active ingredients jetted out (the total weight amount of the active ingredients contained in stage 1 and stage 2: hereinafter also referred to as "Stage 1+Stage 2") to calculate fine particles fraction. Moreover, as a rule in the European Pharmacopoeia, when using the twin impinger (made by Copley, UK), it is stipulated that suction is carried out at an air suction flow rate of 60 L/min, i.e. 1 L/sec, and hence in the examples and comparative examples below this was followed.

Embodiment 1

Dry Powder Inhaler (Jet Type 1)

A description of an embodiment of the jet type dry powder inhaler used in the present invention will now be given using FIG. 1. The dry powder inhaler is an air jet type apparatus for breaking down into fine particles and delivering into the lungs a unit or a plurality of doses of a non-powder-form freeze-dried composition 2 housed at the bottom of a vessel 1, and comprises a needle 5 that has an air jet flow path 3 and a discharge flow path 4, an air intake member 7 that has an inhalation port 6 and is attached to a base end of the needle part 5, a tubular safety cover 8 that surrounds the needle part 5 and also holds the vessel 1, and air pressure-feeding means 9.

The air pressure-feeding means 9 is manually operated and comprises a tubular bellows body 10. An intake port 12 equipped with an intake valve 11, and a discharge port 14 equipped with a discharge valve 13 are provided in the bellows body 10. The discharge port 14 is attached to a connecting port, 15 formed at the base end of the air jet flow path 3 of the needle part 5, and communicates with the air jet flow path 3. By applying a compressive force to the bellows body 10 and thus contracting the bellows body 10 in a state in which the intake valve 11 is closed, the discharge valve 13 is opened, and air in the bellows body 10 is discharged into the vessel 1 from the discharge port 14 via the air jet flow path 3. When the compressive force is released, on the other hand, the bellows body 10 expands due to the elastic restoring force of the bellows body 10, and in a state in which the discharge valve 13 is closed, the intake valve 11 opens, and air is introduced into the bellows body 10.

When using the dry powder inhaler, as shown in FIG. 1, the vessel 1 is inserted into the tubular safety cover 8, and a stopper 1a of the vessel 1 is pierced by the needle part 5, thus communicating the air jet flow path 3 and the discharge flow path 4 with the inside of the vessel 1. In this state, if the bellows body 10 of the air pressure-feeding means 9 is contracted to discharge air from the discharge port 14, then this air passes through the air jet flow path 3 and is jetted out from the tip of the needle part 5 towards the freeze-dried composition 2 in the vessel, and due to the resulting air impact the freeze-dried composition 2 becomes fine particles, which then pass through the discharge flow path 4 of the needle part 5 and are discharged from the inhalation port 6 of the air intake member 7. The user (patient) inhales these fine particles from the inhalation port 6 of the air intake member, whereupon the fine particles of the freeze-dried composition 2 are delivered into the lungs of the user (patient). The material of the stopper of the vessel for use in the invention is not limited, and can be selected from materials usually used for a stopper of a vessel for holding a drug or compound, such as rubber, plastic, aluminum or the like.

With this jet type dry powder inhaler, the air jet amount is set to be about 20 ml, the volume of the vessel about 5 ml, the bore (diameter) of the air jet flow path 3 about 1.2 mm, and the bore (diameter) of the discharge flow path 4 about 1.8 mm.

Note, however, that there is no limitation to this. The preferable range for the bores of the air jet flow path 3 and the discharge flow path 4 varies according to the size of the vessel and so on. These bores can be selected as appropriate from a range of 0.3 to 10 mm, preferably 0.3 to 7 mm, more preferably 0.5 to 5 mm.

Moreover, regarding the air pressure-feeding means 9, the discharge amount of fine particles required for administration by inhalation can be adjusted by adjusting the speed of compression of the bellows body 10. Adjustment can also be carried out by such air jet such that most of the freeze-dried composition 2 is broken down into fine particles.

Embodiment 2

Dry Powder Inhaler (Self-Inhaling Type 1)

A description of an embodiment (first embodiment) of the self-inhaling type dry powder inhaler used in the present invention will now be given using FIG. 2. The dry powder inhaler shown in FIG. 2 comprises a needle part 5 having a suction flow path 16 and an air introduction flow path 17, a tubular safety cover 8, and an air intake member 19 that has an inhalation port 18 and communicates with the suction flow path 16. The air intake member 19 is connected to the base end of the suction flow path 16 of the needle part 5.

When using the dry powder inhaler, as shown in FIG. 2, the vessel 1 is inserted into the tubular safety cover 8, and an stopper 1a of the vessel 1 is pierced by the needle part 5, thus communicating the suction flow path 16 and the air introduction flow path 17 with the inside of the vessel 1. In this state, through the inhalation pressure of the user (patient), air in the vessel 1 is sucked in from the inhalation port 18 via the suction flow path 16, and at the same time outside air flows into the vessel 1, which is now at a negative pressure, from the air introduction flow path 17. At this time, the freeze-dried composition 2 is made into fine particles through the air impact acting on the freeze-dried composition 2, and the fine particles produced are delivered into the user's (patient's) lungs from the inhalation port 18 via the suction flow path 16.

Moreover, with this dry powder inhaler, setting is carried out such that most of the freeze-dried composition 2 is made into fine particles and discharged from the inhalation port 18 through one inhalation of the user (patient). It is considered that the air flow rate of one inhalation of the user (patient) is 5 to 300 L/min, preferably 10 to 200 L/min, more preferably 10 to 100 L/min, but the design of the self-inhaling type dry powder inhaler of the present invention is modified as appropriate in accordance with the respiratory ability of the user (patient) using the device. With the dry powder inhaler shown in FIG. 2, in accordance with the respiratory ability of the user (patient) in question, the volume of the vessel has been set to about 10 ml, and the bores of the air introduction flow path 17 and the suction flow path 16 to about 1.5 mm. As a result, the settings are such that the freeze-dried composition 2 is made into fine particles and discharged from the inhalation port 18 with virtually none left behind through one inhalation of the user (patient).

Embodiment 3

Dry Powder Inhaler (Self-Inhaling Type 2)

A description of an embodiment (second embodiment) of the self-inhaling type dry powder inhaler used in the present invention will now be given using FIG. 3. The dry powder inhaler shown in FIG. 3 is the same as the jet type dry powder inhaler shown in FIG. 1 with the bellows body 10 used for pressure-feeding air removed from the connecting port 15. The discharge flow path 4 of the jet type dry powder inhaler of FIG. 1 corresponds to a suction flow path 16, the air jet flow path 3 to an air introduction flow path 17, and the air intake member 7 having the inhalation port 6 to an air intake member 19 having an inhalation port 18.

When using the self-inhaling type dry powder inhaler in question, the main points are the same as with the dry powder inhaler shown in FIG. 2. Through the inhalation pressure of the user (patient), air in the vessel 1 is sucked in from the inhalation port 18 via the suction flow path 16, and at the same time outside air flows into the vessel 1, which is now at a negative pressure, from the air introduction flow path 17. The freeze-dried composition 2 is made into fine particles through the air impact produced accompanying this inflow of air. The fine particles produced are then delivered into the user (patient's) lungs from the inhalation port 18. As mentioned before, the air flow rate for one inhalation of the user (patient) is generally in a range of 5 to 300 L/minute; however, with the dry powder inhaler shown in FIG. 3, in accordance with the respiratory ability of the user (patient) in question, the volume of the vessel was set to about 5 ml, the bore (diameter) of the air introduction flow path 17 to about 1.2 mm, and the bore (diameter) of the suction flow path 16 to about 1.8 mm. As a result, the settings are such that most of the freeze-dried composition 2 is made into fine particles and discharged from the inhalation port 18 through one inhalation of the user (patient).

If the self-inhaling type dry powder inhaler is constituted in this way, then by detachably installing air pressure-feeding means 9 such as a bellows body 10 into the connecting port 15, the self-inhaling type dry powder inhaler can be changed into a jet type. A single dry powder inhaler can thus be used as either a self-inhaling type or a jet type as desired.

Each of the above dry powder inhalers of the present invention, regardless of whether it is a self-inhaling type or a jet type, can be constituted such that it is possible to select and set the size of the air impact such that the freeze-dried composition becomes fine particles of mean particle diameter 10 microns or less, preferably 5 microns or less, and flies out with almost none left behind.

Embodiment 4

Dry Powder Inhaler (Self-Inhaling Type 3)

Figure 6:
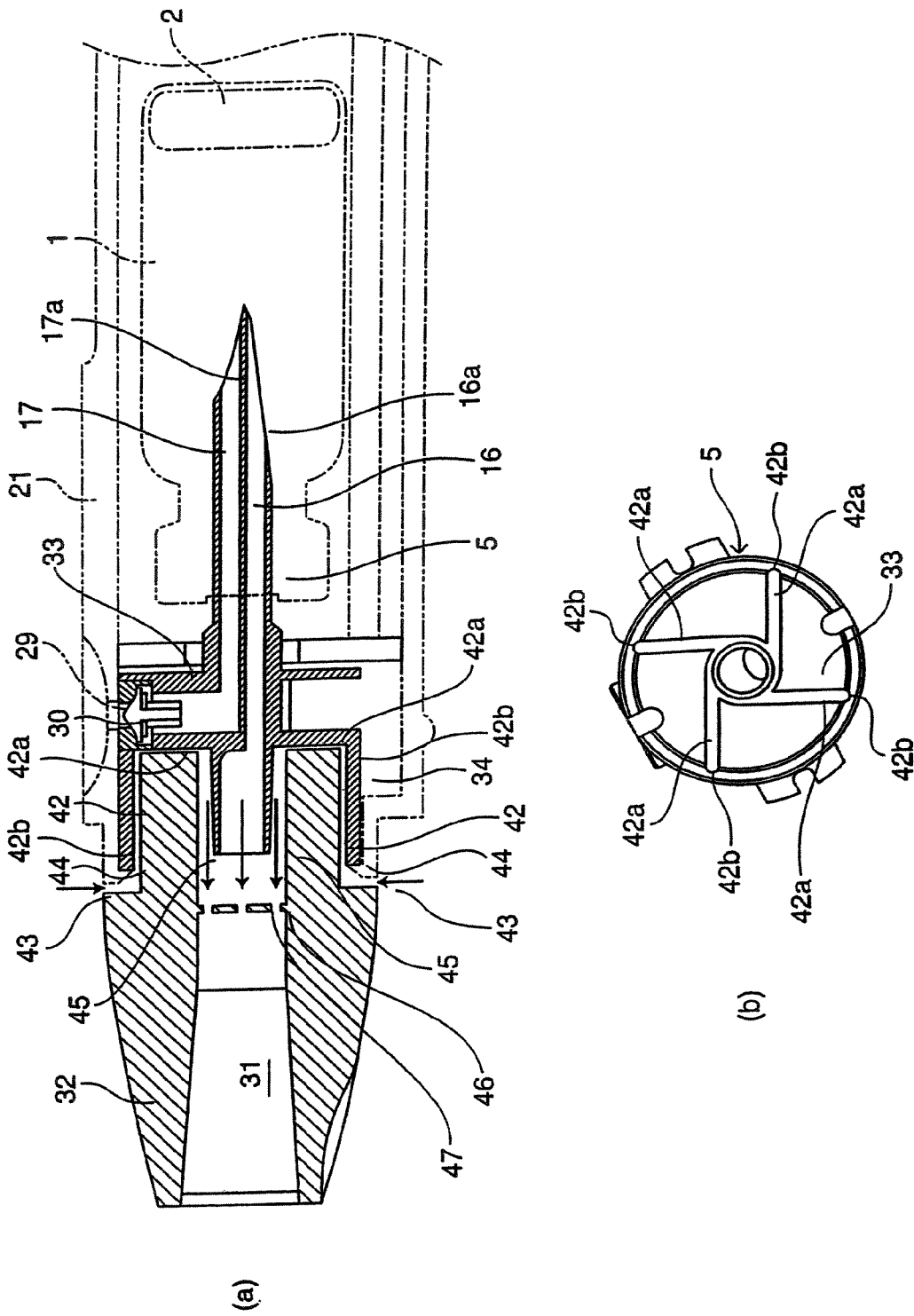

A description of an embodiment (third embodiment) of the self-inhaling type dry powder inhaler used in the present invention will now be given using FIGS. 4 to 10. FIG. 4 is a perspective view showing the dry powder inhaler, and FIG. 5 is a sectional view showing the dry powder inhaler. Moreover, FIG. 6(*a*) is a partial sectional view showing a needle part 5 and a suction port 31 of the dry powder inhaler, and (b) is a side view of the needle part 5. Furthermore, FIGS. 7 to 10 are sectional views for explaining the operation of the dry powder inhaler.

The dry powder inhaler comprises a needle part 5 in which are formed a suction flow path 16 and an air introduction flow path 17, a holder part 22 for holding a vessel 1, a housing chamber 20 for housing the vessel 1 via the holder part 22, a guide part 23 provided in the housing chamber 20 for guiding the holder part 22 in the axial direction of the needle part 5, and a holder operating part 24 for advancing and retreating the holder part 22 along the guide part 23; these are all housed in a tubular housing 21. Moreover, a mouthpiece 32 that has a suction port 31 and communicates with the suction flow path 16 of the needle part 5 is provided at a tip of the housing 21.

Figure 7:
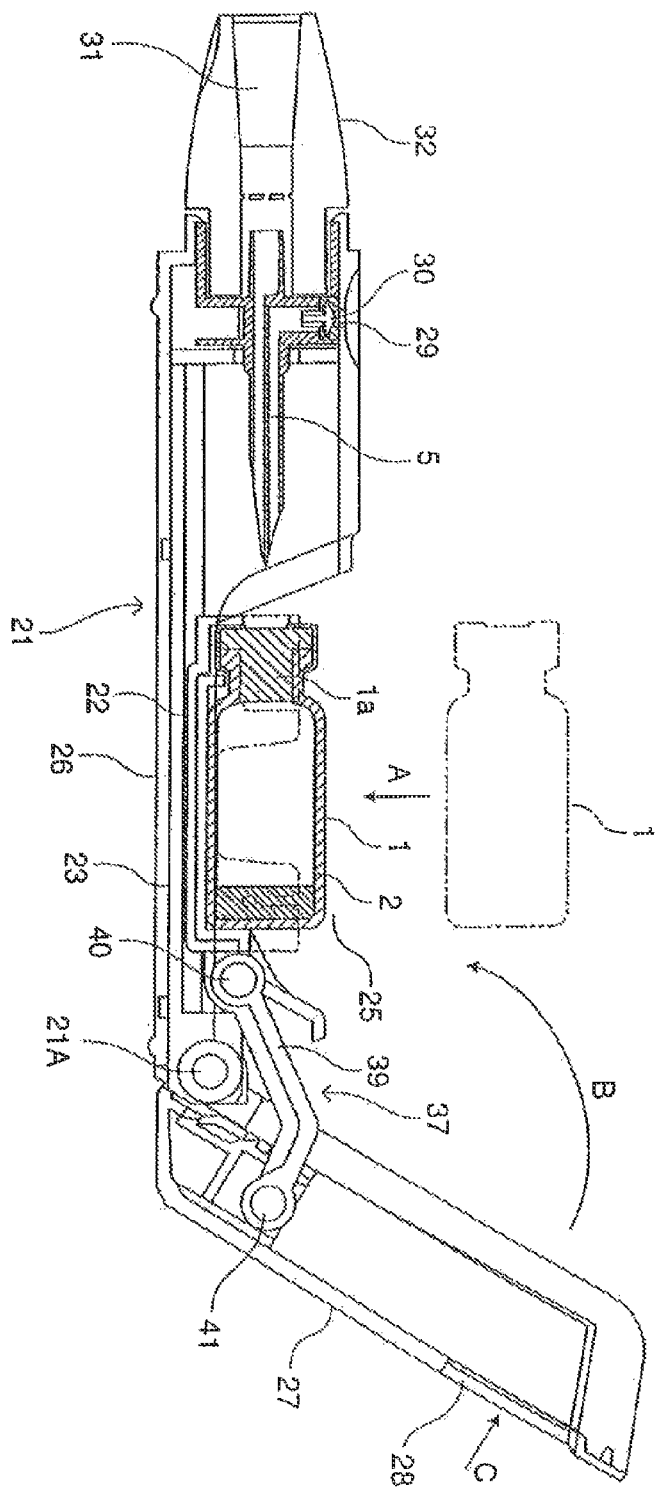
Figure 8:
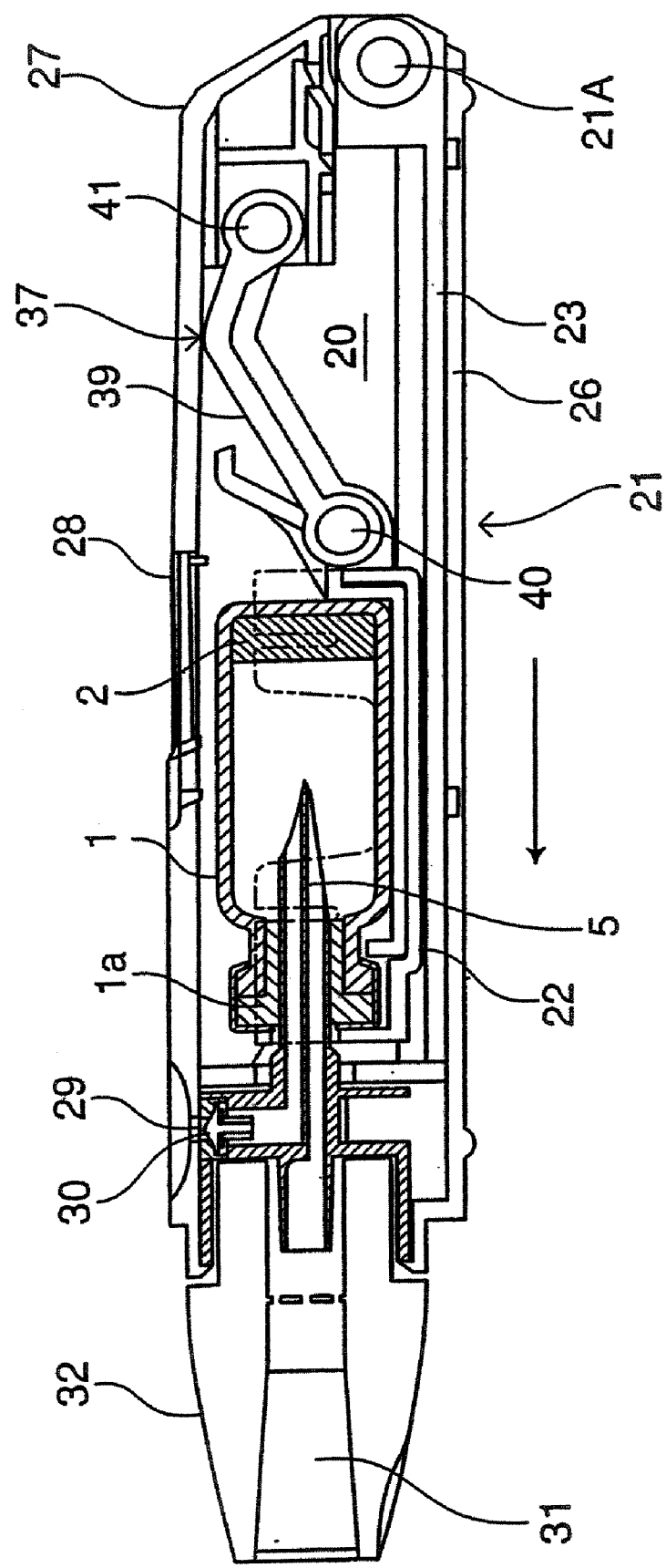
Figure 9:
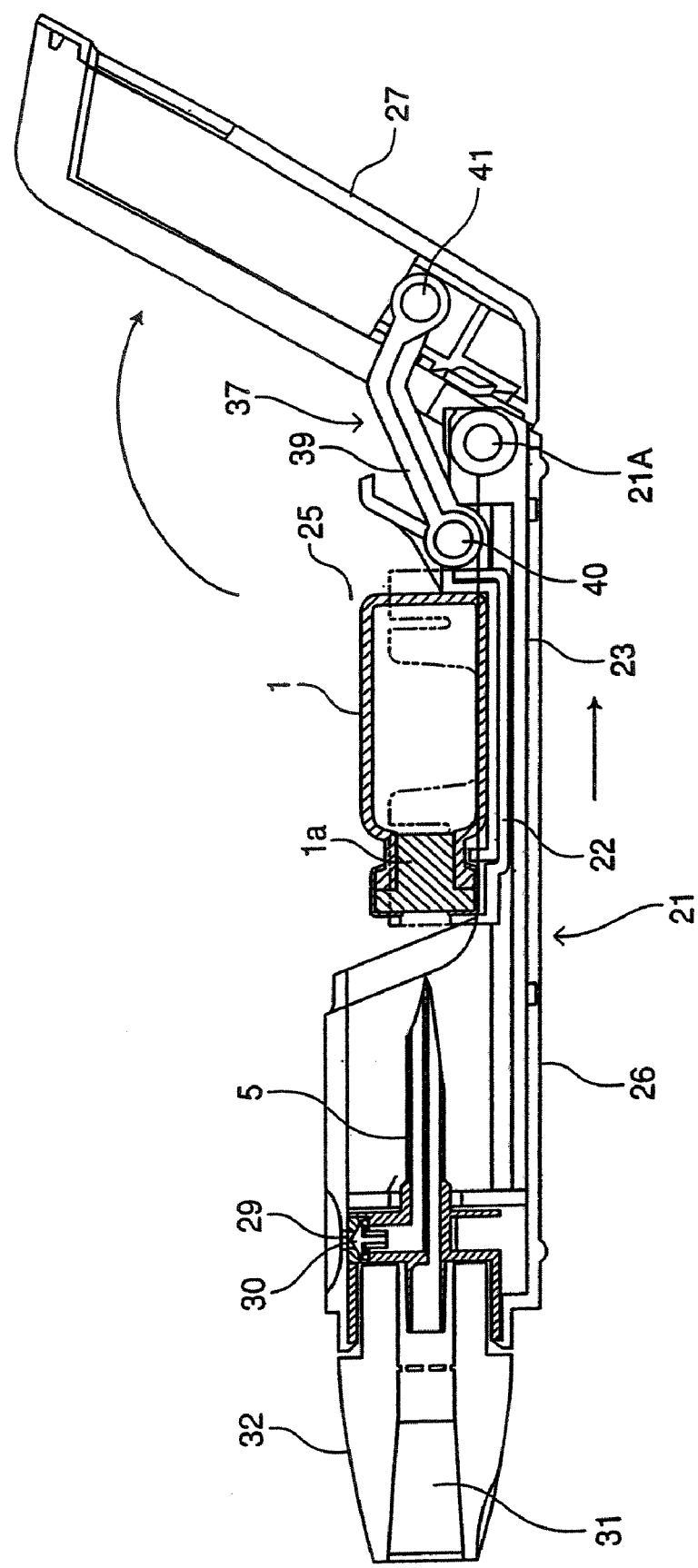
Figure 10:
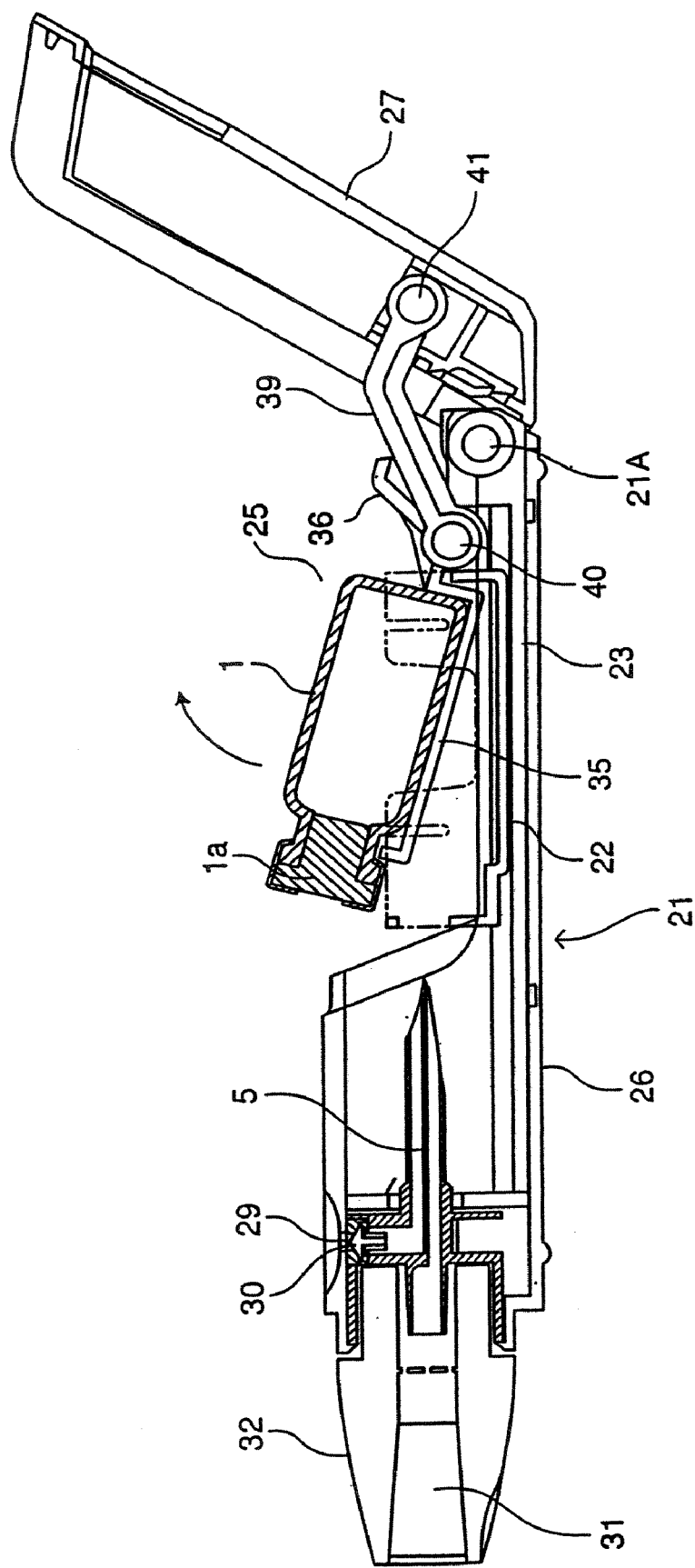

As shown in FIG. 7, in detail the housing 21 is formed from a housing main body 26 in which is formed a removal/insertion port 25 in a position in which the holder part 22 is retreated, and a lid 27 that opens and closes the removal/insertion port 25. The lid 27 is connected to the housing main body 26 by a hinge 21A, and a window 28 for verifying whether the vessel 1 has been loaded is provided in the lid 27.

An introduction port 29 for introducing outside air is provided in a wall of the housing 21, and a check valve 30 is installed at the introduction port 29. Moreover, the mouthpiece 32 is provided at the tip of the housing 21. The suction port 31 of the mouthpiece 32 is covered by a cap 32*a* when the dry powder inhaler is not being used.

A flange-shaped partition part 33 is formed at the base end of the needle part 5, and an end of the air introduction flow path 17 passes through the partition part 33 and opens out in an outer peripheral direction of the partition part 33. Moreover, a peripheral wall part 34 extends from an outer rim part of the partition part 33 towards the suction port 31 of the mouthpiece 32. The needle part 5 is installed into the housing 21 by fitting the partition part 33 into the tip part of the housing 21. Through this installation, the axial direction of the housing 21 and the axial direction of the needle part 5 are aligned with one another.

A remover 35 for lifting the vessel 1 up from the base of the holder part 22 and removing the vessel 1 is attached to the holder part 22, and a lever 36 for lifting the vessel 1 up is formed on the remover 35.

The holder operating part 24 comprises a mechanism part 37 for moving the holder part 22 back and forth along the axial direction of the housing 21, and an operating lever for operating the mechanism part 37. The mechanism part 37 comprises a connector 39. One end of the connector 39 is connected to the holder part 22 by a hinge 40, and the other end of the connector 39 is connected to the lid 27 by a hinge 41. The lid 27 is also used as the above-mentioned operating lever. By opening and closing the lid 27, the holder part 22 is advanced and retreated along the guide part 23.

The point of action of the force for pushing down the lid 27 is shown by the arrow C in FIG. 7. That is, the distance from the hinge 21A to the point of action is made to be longer than the distance from the hinge 21A to the hinge 41. As a result, through the lever principle, the lid (operating lever) 27 can be operated by a force smaller than the force necessary to pierce the stopper 1*a* of the vessel 1 with the needle part 5.

Moreover, as shown in FIG. 6, second introduction paths 42 for supplementary introduction of air are formed in the dry powder inhaler. When sucking the freeze-dried composition that has been made into a powder from the mouthpiece 32, outside air passes through these second introduction path 42 and flows to the suction port 31 of the mouthpiece 32. As a result, the dry powder inhaler can be used without imposing a burden even by a user (patient) having reduced pulmonary capacity or a child patient. Note that the second introduction paths 42 may be omitted.

Introduction grooves 42*a* are provided in the partition part 33 of the needle part 5 and introduction grooves 42*b* are provided in the peripheral wall part 34. By fitting the mouthpiece 32 into the peripheral wall part 34 of the needle part 5, the second introduction paths 42 are thus formed from the mouthpiece 32 and the introduction grooves 42*a* and 42*b*.

A slight gap 43 is formed between the mouthpiece 32 and the housing 21, and one end 44 of the second introduction paths 42 opens out to the outside via the gap 43, while the other end 45 of the second introduction paths 42 opens out into the suction port 31 of the mouthpiece 32.

Moreover, as shown in FIG. 6, a wall 47 having vent holes 46 is provided in the suction port 31. Consequently, even in the case that the air impact applied to the freeze-dried composition 2 is small due to a lack of suction force or the like, and part of the freeze-dried composition 2 is not made into a powder, the non-powder part can be made into a powder when passing through the vent holes 46 of the wall 47.

Moreover, as shown in FIG. 6(*a*), a tip opening 17*a* of the air introduction flow path 17 of the needle part is made to be closer to the freeze-dried composition 2 than a tip opening 16*a* of the suction flow path 16. As a result, dropping of the flow speed of the air that flows into the vessel 1 from the tip opening 17*a* of the air introduction flow path 17 can be suppressed as much as possible, and hence an effective air impact can be applied to the freeze-dried composition 2. Moreover, because the tip opening 16*a* of the suction flow path 16 of the needle part 5 is further from the freeze-dried composition 2 than the tip opening 17*a* of the air introduction flow path 17, making of the freeze-dried composition 2 can be made to into a fine powder in the vessel 1 as much as possible before being sucked into the air introduction flow path 16 of the needle part 5.

The dry powder inhaler is used as follows. Firstly, the lid 27 is lifted up to open the removal/insertion port 25 of the housing 21 as in FIG. 7, whereby the holder part 22 is pulled backwards to reach the removal/insertion port 25 of the housing 21. Next, the vessel 1 is installed in the holder part 22 with the stopper 1*a* facing forwards. Next, the lid 27 is pushed down to close the removal/insertion port 25 of the housing 21 as in FIG. 8, whereby the holder part 22 is pushed towards the needle part 5 by the connector 39, and the stopper 1*a* of the vessel 1 is pierced by the tip of the needle part 5, thus communicating the suction flow path 16 and the air introduction flow path 17 of the needle part 5 with the inside of the vessel 1. Next, air in the vessel 1 is sucked from the suction port 31 of the mouthpiece 32 through the suction flow path 16 of the needle part 5 by the inhalation pressure of the user (patient). At this time, the inside of the vessel 1 becomes a negative pressure and the check valve 30 opens, and outside air flows into the vessel 1 through the air introduction flow path 17 of the needle part 5. As a result, an air impact is generated in the vessel 1 and the freeze-dried composition 2 is broken down into fine particles, and the fine particles prepared are delivered into the user's (patient's) lungs from the suction port 31 via the suction flow path 16. After use, the lid 27 is lifted up to pull the holder part 22 back up to the removal/insertion port 25 of the housing 21, and then the remover 35 is lifted up by the lever 36 and the vessel 1 is removed from the holder part 22.

Even if air is conversely blown into the vessel 1 from the suction port 31 of the mouthpiece 32, discharge to the outside of the freeze-dried composition 2 made into fine particles is prevented by the check valve 30.

As mentioned before, the air flow rate of one inhalation of the user (patient) is generally in a range of 5 to 300 L/min, but with the dry powder inhaler shown in FIGS. 4 to 10, in accordance with the respiratory ability of the user (patient), the volume of the vessel 1 has been set to about 5 ml, the bore (diameter) of the air introduction flow path 17 to about 2.5 mm, and the bore (diameter) of the suction flow path 16 to about 2.5 mm. As a result, the settings are such that most of the freeze-dried composition 2 is made into fine particles and discharged from the suction port 31 through one inhalation of the user (patient).

Other embodiments of the dry powder inhaler (self-inhaling type) are shown in FIGS. 11 to 13.

With the dry powder inhaler (self-inhaling type 4) shown in FIG. 11, an operating member 48 is provided so as to be freely rotatable in the circumferential direction of the housing 21 as shown by the arrow. The mechanism part of the holder operating part, which is not shown in the drawing, comprises a spiral groove and a follower that engages into the same; when the operating member 48 is rotated, this rotation is converted to linear movement of the holder part 22 in the axial direction of the needle part 5. Note that the angle of rotation of the operator 48 is about 180°.

With the dry powder inhaler (self-inhaling type 5) shown in FIG. 12 and FIG. 13, an annular operating member 49 is installed so as to be freely rotatable in the housing 21. The mechanism part of the holder operating part, which is not shown in the drawing, comprises a feed screw; when the operating member 49 is rotated, this rotation is converted to linear movement of the holder part 22 in the axial direction of the needle part 5. The holder part 22 can be withdrawn from the back of the housing 21.

Examples 1 to 13, Comparative Examples 1 to 4

An interferon-α (IFN-α) stock liquid (potency: $2\times10^7$ IU/ml) was desalinated using an ultrafilter membrane (Ultrafree 15, made by Millipore). 0.25 ml of the desalinated IFN-α stock liquid obtained and 2 mg of any of various carriers as shown in Table 1 were filled into vessels (trunk diameter 18 mm), being made up with distilled water for a injection (injection distilled water) such that the volume was 0.5 ml per vessel, and freeze-drying was carried out using a shelf-type freeze-dryer (Lyovac GT-4, made by Leybold). The disintegration index of the non-powder-form (cake-like) freeze-dried composition (freeze-dried cake) obtained was calculated. Next, a vessel containing the non-powder-form freeze-dried composition (freeze-dried cake) obtained was installed in a jet type dry powder inhaler (having a bellows body 10 capable of supplying an amount of air of about 20 ml; FIG. 1) designed such that the bore of the air jet flow path 3 was 1.2 mm and the bore of the discharge flow path 4 was 1.8 mm.

It was verified that, by introducing an amount of air of about 20 ml from the dry powder inhaler into the vessel (giving an air impact arising through an air speed of about 35 m/sec and an air flow rate of about 40 ml/sec), the non-powder-form freeze-dried cake in the vessel was made into fine particles, and the fine particles were jetted out from the vessel via the discharge flow path 4 in an instant. The fine particles were collected using a particle size distribution meter (Aerosizer: made by Amherst Process Instrument, Inc., USA; R. W. Niven: Pharmaceutical Technology, 72-78 (1993)) fitted with an Aerobreather (made by Amherst Process Instrument, Inc., USA, R. W. Niven: Pharmaceutical Technology, 72-78 (1993)), which is an artificial lung model capable of directly measuring the particle size distribution of the particles jetted out from the vessel (measurement conditions: breath rate: 60 L/min, breath volume: 1 L, acceleration: 19); the particle size distribution of the fine particles that had been made was thus measured, and the mass median aerodynamic diameter (μm±SD) was calculated from the particle size distribution. The disintegration index, and the mass median aerodynamic diameter (μm±SD) of the fine particles jetted out from the inhaler are shown in Table 1 for each of the freeze-dried compositions.

TABLE 1

|   | Freeze-dried composition | Disintegration index | Mass median aerodynamic diameter (μm ± SD, MMAD) |
|---|---|---|---|
| Examples | | | |
| 1. | IFN-α + isoleucine | 0.225 | 1.614 ± 1.590 |
| 2. | IFN-α + valine | 0.173 | 1.091 ± 1.390 |
| 3. | IFN-α + leucine | 0.221 | 1.120 ± 1.416 |
| 4. | IFN-α + phenylalanine | 0.264 | 1.053 ± 1.405 |
| 5. | IFN-α + alanine | 0.168 | 1.456 ± 1.403 |
| 6. | IFN-α + glycine | 0.171 | 1.951 ± 1.419 |
| 7. | IFN-α + β-alanine | 0.109 | 2.420 ± 1.525 |
| 8. | IFN-α + γ-aminobutyric acid | 0.139 | 2.103 ± 1.546 |
| 9. | IFN-α + taurine | 0.136 | 2.132 ± 1.526 |
| 10. | IFN-α + D-mannitol | 0.180 | 2.128 ± 1.575 |
| 11. | IFN-α + lactose | 0.077 | 2.848 ± 1.837 |
| 12. | IFN-α + β-cyclodextrin | 0.176 | 3.700 ± 1.526 |
| 13. | IFN-α + PEG4000 | 0.161 | 2.759 ± 1.577 |
| Comparative Examples | | | |
| 1. | IFN-α + dextran 40 | 0.002 | Didn't scatter at all, measurement impossible |
| 2. | IFN-α + dextran 70 | 0.002 | Didn't scatter at all, measurement impossible |
| 3. | IFN-α + chondroitin sulfate | 0.001 | Didn't scatter at all, measurement impossible |

TABLE 1-continued

|  | Freeze-dried composition | Disintegration index | Mass median aerodynamic diameter ($\mu$m ± SD, MMAD) |
|---|---|---|---|
| 4. | IFN-$\alpha$ + pullulan | 0.001 | Didn't scatter at all, measurement impossible |

For all of the examples and comparative examples, the freeze-dried composition containing the IFN-$\alpha$ and the carrier shown in Table 1 was a non-powder-form cake-like mass (freeze-dried cake) at the time of freeze-drying. As can be seen from Table 1, the non-powder-form freeze-dried cakes having a disintegration index of 0.002 or less (Comparative Examples 1 to 4) were not disintegrated by the air impact arising through an air speed of about 35 m/sec and an air flow rate of about 40 ml/sec, and hence it was not possible to make fine particles. On the other hand, the non-powder-form freeze-dried cakes showing a disintegration index of 0.077 or more (Examples 1 to 13) were disintegrated by the air impact arising through an air speed of about 35 m/sec and an air flow rate of about 40 ml/sec, becoming fine particles of mass median aerodynamic diameter less than 5 microns, i.e. becoming a fine-particle-form powdered preparation suitable for transpulmonary administration.

For Examples 1, 2, 3, 4, 5 and 6, the particle size distributions of the fine particles jetted out from the dry powder inhaler are shown in FIGS. 14, 15, 16, 17, 18 and 19 respectively.

Examples 14 to 26, Comparative Examples 5 to 8

5 $\mu$l of an interleukin-1$\alpha$ (IL-1$\alpha$) stock liquid (potency: $1\times10^8$ U/ml) and 2 mg of any of various carriers as shown in Table 2 were filled into vessels (trunk diameter 18 mm), being made up with injection distilled water such that the volume was 0.5 ml per vessel, and freeze-drying was carried out using a shelf-type freeze-dryer (Lyovac GT-4, made by Leybold). The disintegration index of the non-powder-form (cake-like) freeze-dried composition (freeze-dried cake) obtained was calculated. Next, a vessel filled with the non-powder-form freeze-dried composition (freeze-dried cake) obtained was installed in a jet type dry powder inhaler (having a bellows body 10 capable of supplying an amount of air of about 20 ml; FIG. 1) designed such that the bore of the air jet flow path 3 was 1.2 mm and the bore of the discharge flow path 4 was 1.8 mm.

As in Examples 1 to 13, this inhaler was attached to an Aerosizer (made by Amherst Process Instrument, Inc., USA) fitted with an Aerobreather, which is an artificial lung model, and an amount of air of about 20 ml was introduced into the vessel from the inhaler, thus applying an air impact arising through an air speed of about 35 m/sec and an air flow rate of about 40 ml/sec to the freeze-dried cake. As a result, air was introduced from the air jet flow path 3 of the jet type dry powder inhaler into the vessel 1, and it was observed that the non-powder-form freeze-dried composition in the vessel was made into fine particles by the air impact. The particle size distribution of the fine particles was measured using the Aerosizer fitted with the Aerobreather (measurement conditions: breath rate: 60 L/min, breath volume: 1 L, acceleration: 19). The mass median aerodynamic diameter ($\mu$m±SD) was then calculated from the particle size distribution of the fine particles jetted out from the inhaler. The disintegration index and the mass median aerodynamic diameter ($\mu$m±SD) are shown in Table 2 for each of the freeze-dried compositions.

TABLE 2

|  | Freeze-dried composition | Disintegration index | Mass median aerodynamic diameter ($\mu$m ± SD, MMAD) |
|---|---|---|---|
| Examples | | | |
| 14. | IL-1$\alpha$ + isoleucine | 0.172 | 1.539 ± 1.527 |
| 15. | IL-1$\alpha$ + valine | 0.195 | 1.337 ± 1.440 |
| 16. | IL-1$\alpha$ + leucine | 0.220 | 1.115 ± 1.464 |
| 17. | IL-1$\alpha$ + phenylalanine | 0.314 | 1.391 ± 1.496 |
| 18. | IL-1$\alpha$ + alanine | 0.129 | 2.070 ± 1.647 |
| 19. | IL-1$\alpha$ + glycine | 0.110 | 1.978 ± 1.420 |
| 20. | IL-1$\alpha$ + $\beta$-alanine | 0.106 | 2.204 ± 1.509 |
| 21. | IL-1$\alpha$ + $\gamma$-aminobutyric acid | 0.166 | 2.149 ± 1.534 |
| 22. | IL-1$\alpha$ + taurine | 0.147 | 2.026 ± 1.520 |
| 23. | IL-1$\alpha$ + D-mannitol | 0.124 | 1.765 ± 1.460 |
| 24. | IL-1$\alpha$ + lactose | 0.097 | 3.681 ± 1.851 |
| 25. | IL-1$\alpha$ + $\beta$-cyclodextrin | 0.178 | 3.234 ± 1.515 |
| 26. | IL-1$\alpha$ + PEG4000 | 0.116 | 2.494 ± 1.547 |
| Comparative Examples | | | |
| 5. | IL-1$\alpha$ + dextran 40 | 0.001 | Didn't scatter at all, measurement impossible |
| 6. | IL-1$\alpha$ + dextran 70 | 0.002 | Didn't scatter at all, measurement impossible |
| 7. | IL-1$\alpha$ + chondroitin sulfate | 0.001 | Didn't scatter at all, measurement impossible |
| 8. | IL-1$\alpha$ + pullulan | 0.001 | Didn't scatter at all, measurement impossible |

Each of the freeze-dried compositions containing the IL-1α and the carrier shown in Table 2 was a non-powder-form cake-like mass (freeze-dried cake) at the time of freeze-drying. As can be seen from Table 2, the non-powder-form freeze-dried cakes having a disintegration index of 0.002 or less (Comparative Examples 5 to 8) were not disintegrated by the air impact arising through an air speed of about 35 m/sec and an air flow rate of about 40 ml/sec, and hence it was not possible to make fine particles. On the other hand, the non-powder-form freeze-dried cakes showing a disintegration index of 0.097 or more (Examples 14 to 26) were disintegrated by the air impact arising through an air speed of about 35 m/sec and an air flow rate of about 40 ml/sec, becoming fine particles of mass median aerodynamic diameter less than 5 microns, i.e. becoming a fine-particle-form powdered preparation suitable for transpulmonary administration.

Examples 27 to 37

An interferon-γ (IFN-γ) stock liquid (potency: $1×10^7$ IU/ml) was desalinated using an ultrafilter membrane (Ultrafree 15, made by Millipore). 0.01 ml of the desalinated IFN-γ stock liquid obtained and any of various carriers as shown in Table 3 were filled into vessels (trunk diameter 18 mm), the volume was made up with injection distilled water to 0.5 ml per vessel, and freeze-drying was carried out using a shelf-type freeze-dryer (Lyovac GT-4, made by Leybold). The disintegration index of the non-powder-form (cake-like) freeze-dried composition (freeze-dried cake) obtained was calculated. Next, a vessel filled with the non-powder-form freeze-dried composition (freeze-dried cake) obtained was installed in a jet type dry powder inhaler (having a bellows body 10 capable of supplying an amount of air of about 20 ml; FIG. 1) designed such that the bore of the air jet flow path 3 was 1.2 mm and the bore of the discharge flow path 4 was 1.8 mm.

As in Examples 1 to 13, this inhaler was attached to an Aerosizer (made by Amherst Process Instrument, Inc., USA) fitted with an Aerobreather, which is an artificial lung model, and an amount of air of about 20 ml was introduced into the vessel from the inhaler, thus applying an air impact arising through an air speed of about 35 m/sec and an air flow rate of about 40 ml/sec to the freeze-dried cake. As a result, air was introduced from the air jet flow path 3 of the jet type dry powder inhaler into the vessel 1, and it was observed that the non-powder-form freeze-dried composition in the vessel was made into fine particles by the air impact. The particle size distribution of the fine particles was measured using the Aerosizer fitted with the Aerobreather (measurement conditions: breath rate: 60 L/min, breath volume: 1 L, acceleration: 19). The mass median aerodynamic diameter (μm±SD) was then calculated from the particle size distribution of the fine particles jetted out from the inhaler.

Moreover, to calculate the fine particle fraction (%) of the fine particles for each freeze-dried composition and thus evaluate the efficiency of delivery into the lungs, an air impact arising through an air speed of about 35 m/sec and an air flow rate of about 40 ml/sec was applied to the freeze-dried cake filled into a vessel using the dry powder inhaler, and the resulting powdered fine-particle-form freeze-dried composition was discharged directly into a twin impinger (made by Copley, UK). After this, the solvents in stage 1 and stage 2 were collected, the IFN-γ in the stage 1 and stage 2 solvents were assayed using a bioassay method. The value obtained by dividing the amount (weight) of IFN-γ obtained in stage 2 by the total amount (weight) of IFN-γ jetted out (stage 1+stage 2) was then calculated as the fine particle fraction (%). The disintegration index, the mass median aerodynamic diameter (μm±SD) of the fine particles jetted out from the device, and the fine particle fraction (%) are shown in Table 3 for each of the freeze-dried compositions.

TABLE 3

| Freeze-dried Composition | Disintegration index | Mass median aerodynamic diameter (μm ± SD, MMAD) | Fine particle fraction (%) |
|---|---|---|---|
| 27. IFN-γ + Leu (2.5 mg) | 0.197 | 1.814 ± 1.538 | 72.0 |
| 28. IFN-γ + Val (2.5 mg) | 0.207 | 1.553 ± 1.451 | 50.2 |
| 29. IFN-γ + Ile (2.5 mg) | 0.185 | 1.652 ± 1.479 | 53.0 |
| 30. IFN-γ + Phe (2.5 mg) | 0.215 | 1.322 ± 1.443 | 74.0 |
| 31. IFN-γ + Leu (0.5 mg) + Val (2 mg) | 0.199 | 1.504 ± 1.461 | 51.4 |
| 32. IFN-γ + Leu (0.48 mg) + Val (1.92 mg) + Arg-HCl (0.2 mg) | 0.159 | 1.500 ± 1.464 | 52.0 |
| 33. IFN-γ + Phe (1.2 mg) + Leu (0.3 mg) + Arg-HCl (0.2 mg) | 0.191 | 1.264 ± 1.383 | 67.0 |
| 34. IFN-γ + Phe (1.2 mg) + Val (0.3 mg) + Arg-HCl (0.2 mg) | 0.190 | 1.350 ± 1.456 | 64.0 |
| 35. IFN-γ + Phe (1.2 mg) + Ile (0.3 mg) + Arg-HCl (0.2 mg) | 0.181 | 1.230 ± 1.386 | 67.0 |
| 36. IFN-γ + Phe (1.0 mg) + Arg-HCl (0.2 mg) | 0.269 | 1.280 ± 1.473 | 59.0 |
| 37. IFN-γ + Leu (1.5 mg) + Val (1.0 mg) + D-mannitol (1.0 mg) | 0.191 | 1.545 ± 1.405 | 45.4 |

Leu: leucine,
Val: valine,
Ile: isoleucine,
Phe: phenylalanine,
Arg-HCl: arginine hydrochloride Each of the freeze-dried compositions containing the IFN-γ and the carrier shown in Table 3 was a non-powder-form cake-like mass (freeze-dried cake) at the time of freeze-drying. As can be seen from Table 3, the non-powder-form freeze-dried cakes showing a disintegration index of 0.159 or more (Examples 27 to 37) were disintegrated by the air impact arising through an air speed of about 35 m/sec and an air flow rate of about 40 ml/sec, becoming fine particles of mass median aerodynamic diameter less than 5 microns, i.e. becoming a fine-particle-form powdered preparation suitable for transpulmonary administration. Moreover, a good fine particle fraction was obtained for all of the compositions (IFN-γ carrier).

Examples 38 to 48, Comparative Examples 9 to 10

5 μg of procaterol hydrochloride (made by Otsuka Pharmaceutical Co., Ltd.) and 1.5 mg of any of various carriers as shown in Table 4 were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form (cake-like) freeze-dried composition (freeze-dried cake) obtained was calculated. Next, a vessel (trunk diameter 18 mm) filled with the non-powder-form freeze-dried cake obtained was installed in a self-inhaling type dry powder inhaler designed such that the bore of the air introduction flow path 17 was 1.99 mm and the bore of the suction flow path 16 was 1.99 mm.

To evaluate the delivery into the lungs of the freeze-dried composition obtained, the above-mentioned self-inhaling type dry powder inhaler was attached to a twin impinger (made by Copley, UK) (applying an air impact arising through an air speed of about 95 m/sec and an air flow rate of about 295 ml/sec to the freeze-dried cake), the solvents in stage 1 and stage 2 were respectively collected, and each of the procaterol hydrochloride contained in the stage 1 or stage 2 solvent was assayed by an HPLC method. The value obtained by dividing the amount of procaterol hydrochloride obtained in stage 2 by the total amount of procaterol hydrochloride jetted out (stage 1+stage 2) was then calculated as the fine particle fraction (%, the proportion that can be expected to reach the lungs).

The disintegration index and the fine particle fraction (%) are shown in Table 4 for each of the freeze-dried compositions.

TABLE 4

| | Freeze-dried composition | Disintegration index | Fine particle fraction (%) |
|---|---|---|---|
| Examples | | | |
| 38. | Procaterol-HCl + isoleucine | 0.199 | 61.1 |
| 39. | Procaterol-HCl + valine | 0.270 | 71.9 |
| 40. | Procaterol-HCl + leucine | 0.260 | 74.0 |
| 41. | Procaterol-HCl + phenylalanine | 0.245 | 70.8 |
| 42. | Procaterol-HCl + alanine | 0.048 | 61.6 |

TABLE 4-continued

| | Freeze-dried composition | Disintegration index | Fine particle fraction (%) |
|---|---|---|---|
| 43. | Procaterol-HCl + glycine | 0.139 | 60.6 |
| 44. | Procaterol-HCl + taurine | 0.110 | 63.3 |
| 45. | Procaterol-HCl + D-mannitol | 0.144 | 60.7 |
| 46. | Procaterol-HCl + β-cyclodextrin | 0.138 | 69.1 |
| 47. | Procaterol-HCl + PEG4000 | 0.102 | 63.6 |
| 48. | Procaterol-HCl + sodium caprate | 0.222 | 73.4 |
| Comparative Examples | | | |
| 9. | Procaterol-HCl + pullulan | 0.001 | 0.0 |
| 10. | Procaterol-HCl + dextran 40 | 0.003 | 0.0 |

Procaterol-HCl: Procaterol hydrochloride

As shown in Table 4, the non-powder-form freeze-dried compositions (freeze-dried cakes) having a disintegration index of 0.003 or less (Comparative Examples 9 and 10) were not disintegrated by the air impact arising through an air speed of about 95 m/sec and an air flow rate of about 295 ml/sec, whereas the non-powder-form freeze-dried compositions (freeze-dried cakes) having a disintegration index of 0.048 or more were easily made into fine particles in the vessel by the above-mentioned air impact, with it being possible to produce a powdered preparation suitable for transpulmonary administration.

Examples 49 to 58, Comparative Examples 11 to 14

5 μg of procaterol hydrochloride (made by Otsuka Pharmaceutical Co., Ltd.) and any of various carriers as shown in Table 5 were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form cake-like freeze-dried composition (freeze-dried cake) obtained was calculated.

Next, as with Examples 38 to 48, a vessel (trunk diameter 18 mm) filled with the non-powder-form freeze-dried composition obtained was installed in a self-inhaling type dry powder inhaler designed such that the bore of the air introduction flow path 17 was 1.99 mm and the bore of the suction flow path 16 was 1.99 mm. Using this, the fine particle fraction (%) was calculated with a twin impinger (made by Copley, UK) (applying an air impact arising through an air speed of about 95 m/sec and an air flow rate of about 295 ml/sec to the freeze-dried cake). The disintegration index and the fine particle fraction (%) are shown in Table 5 for each of the freeze-dried compositions.

TABLE 5

| | Freeze-dried composition | Disintegration index | Fine particle fraction (%) |
|---|---|---|---|
| Examples | | | |
| 49. | Procaterol-HCl + 4.5 mg isoleucine | 0.170 | 57.2 |
| 50. | Procaterol-HCl + 7.5 mg isoleucine | 0.156 | 52.8 |
| 51. | Procaterol-HCl + 4.5 mg leucine | 0.214 | 74.0 |
| 52. | Procaterol-HCl + 7.5 mg leucine | 0.191 | 58.0 |
| 53. | Procaterol-HCl + 4.5 mg valine | 0.174 | 62.0 |
| 54. | Procaterol-HCl + 4.5 mg phenylalanine | 0.237 | 56.9 |
| 55. | Procaterol-HCl + 4.5 mg PEG4000 | 0.152 | 52.5 |
| 56. | Procaterol-HCl + 4.5 mg sodium caprate | 0.168 | 51.4 |
| 57. | Procaterol-HCl + 4.5 mg alanine | 0.023 | 58.5 |
| 58. | Procaterol-HCl + 7.5 mg alanine | 0.018 | 50.7 |

TABLE 5-continued

| | Freeze-dried composition | Disintegration index | Fine particle fraction (%) |
|---|---|---|---|
| Comparative Examples | | | |
| 11. | Procaterol-HCl + 4.5 mg pullulan | 0.0003 | 0.0 |
| 12. | Procaterol-HCl + 7.5 mg pullulan | 0.0002 | 0.0 |
| 13. | Procaterol-HCl + 4.5 mg dextran 40 | 0.0013 | 0.0 |
| 14. | Procaterol-HCl + 7.5 mg dextran 40 | 0.0010 | 0.0 |

Procaterol-HCl: Procaterol hydrochloride

As shown in Table 5, the non-powder-form freeze-dried compositions (freeze-dried cakes) having a disintegration index of 0.0013 or less (Comparative Examples 11 to 14) were not disintegrated by the air impact arising through an air speed of about 95 m/sec and an air flow rate of about 295 ml/sec, whereas the non-powder-form freeze-dried compositions (freeze-dried cakes) showing a disintegration index of 0.018 or more (Examples 49 to 58) were easily made into fine particles in the vessel by the above-mentioned air impact, with it being possible to produce a powdered preparation suitable for transpulmonary administration.

Examples 59 to 64

5 µg of procaterol hydrochloride (made by Otsuka Pharmaceutical Co., Ltd.) and any of various carriers as shown in Table 6 were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form cake-like freeze-dried composition (freeze-dried cake) obtained was calculated. Next, as with Examples 38 to 48, a vessel (trunk diameter 18 mm) filled with the non-powder-form freeze-dried composition obtained was installed in a self-inhaling type dry powder inhaler designed such that the bore of the air introduction flow path 17 was 1.99 mm and the bore of the suction flow path 16 was 1.99 mm. Using this, the fine particle fraction (%) was calculated with a twin impinger (made by Copley, UK) (applying an air impact arising through an air speed of about 95 m/sec and an air flow rate of about 295 ml/sec to the freeze-dried cake) The disintegration index and the fine particle fraction (%) are shown in Table 6 for each of the freeze-dried compositions.

TABLE 6

| Freeze-dried composition | Disintegration index | Fine particle fraction (%) |
|---|---|---|
| 59. Procaterol-HCl + 0.5 mg Leu-Val | 0.104 | 74.5 |
| 60. Procaterol-HCl + 1.5 mg Leu-Val | 0.073 | 63.0 |
| 61. Procaterol-HCl + 4.5 mg Leu-Val | 0.039 | 53.1 |
| 62. Procaterol-HCl + 0.375 mg Leu-Phe | 0.168 | 81.9 |
| 63. Procaterol-HCl + 0.5 mg Leu-Phe | 0.222 | 76.1 |
| 64. Procaterol-HCl + 0.75 mg Leu-Phe | 0.181 | 79.1 |

Procaterol-HCl: Procaterol hydrochloride,
Leu-Val: leucyl-valine,
Leu-Phe: leucyl-phenylalanine As shown in Table 6, the non-powder-form freeze-dried compositions (freeze-dried cakes), which showed a disintegration index of 0.039 or more, were easily made into fine particles in the vessel by the air impact arising through an air speed of about 95 m/sec and an air flow rate of about 295 ml/sec, with it being possible to produce a powdered preparation suitable for transpulmonary administration.

Example 65

5 µg of procaterol hydrochloride (made by Otsuka Pharmaceutical Co., Ltd.) and 1.0 mg of valine were made up to 0.5 ml by dissolving in injection distilled water, this was filled into vessels (trunk diameter 23 mm), and freeze-drying was carried out using a shelf-type freeze-dryer (Lyovac GT-4, made by Leybold). The disintegration index of the non-powder-form freeze-dried composition (freeze-dried cake) obtained was calculated. Next, a vessel (trunk diameter 23 mm) filled with the non-powder-form freeze-dried composition obtained was installed in a self-inhaling type dry powder inhaler designed such that the bore of the air introduction flow path 17 was 4.01 mm and the bore of the suction flow path 16 was 4.01 mm. This was directly jetted out into an Aerosizer (made by Amherst Process Instrument, Inc., USA) fitted with an Aerobreather (made by Amherst Process Instrument, Inc., USA; measurement conditions: breath rate: 1 L/min, breath volume: 0.1 L), which is an artificial lung model capable of directly measuring the particle size distribution of the particles jetted out (applying an air impact arising through an air speed of about 1 m/sec and an air flow rate of about 17 ml/sec to the freeze-dried cake), and the particle size distribution of the fine particles jetted out was measured. The mass median aerodynamic diameter (µm±SD) of the fine particles was calculated from the particle size distribution. The disintegration index, and the mass median aerodynamic diameter of the fine particles jetted out from the inhaler are shown in Table 7 for the freeze-dried composition.

TABLE 7

| Freeze-dried composition | Disintegration index | Mass median aerodynamic diameter (µm ± SD, MMAD) |
|---|---|---|
| 65. Procaterol-HCl + valine | 0.273 | 1.582 ± 1.552 |

Procaterol-HCl: Procaterol hydrochloride

As shown in Table 7, the non-powder-form freeze-dried composition (freeze-dried cake), which showed a disintegration index of 0.273, was easily made into fine particles in the vessel by the above-mentioned air impact, and moreover the mean particle diameter was less than 5 microns, and hence it was possible to produce a preparation suitable for transpulmonary administration.

Examples 66 to 70

Insulin (recombinant human insulin crystal, made by Biobras, Brazil; relative activity: 26.4 U/mg) (1 mg, 2 mg), or insulin and any of various carriers as shown in Table 8, was/ were made up to 0.2 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form freeze-dried composition (freeze-dried cake) obtained was calculated. Next, as in Examples 38 to 48, a vessel (trunk diameter 18 mm) filled with the non-powder-form freeze-dried composition obtained was installed in a self-inhaling type dry powder inhaler designed such that the bore of the air introduction flow path 17 was 1.99 mm and the bore of the suction flow path 16 was 1.99 mm. Using this, the fine particle fraction (%) was calculated with a twin impinger (made by Copley, UK) (applying an air impact arising through an air speed of about 95 m/sec and an air flow rate of about 295 ml/sec to the freeze-dried cake). The disintegration index and the fine particle fraction (%) are shown in Table 8 for each of the freeze-dried compositions.

TABLE 8

| Freeze-dried composition | Disintegration index | Fine particle fraction (%) |
| --- | --- | --- |
| 66. 1 mg insulin | 0.159 | 75.0 |
| 67. 1 mg insulin + 1.4 mg leucine | 0.145 | 80.7 |
| 68. 1 mg insulin + 1.0 mg valine | 0.110 | 79.4 |
| 69. 2 mg insulin | 0.177 | 42.4 |
| 70. 2 mg insulin + 1.4 mg leucine | 0.137 | 65.1 |

As can be seen from Table 8, regardless of whether or not a carrier was present, the non-powder-form freeze-dried compositions (freeze-dried cakes), which showed a disintegration index of 0.110 or more, were easily made into fine particles in the vessel by the above-mentioned air impact, with it being possible to produce a powdered preparation suitable for transpulmonary administration.

Examples 71 to 75

1 mg of insulin (recombinant human insulin crystal, made by Biobras, Brazil; relative activity: 26.4 U/mg) and any of various carriers (1.5 mg) as shown in Table 9 were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form freeze-dried composition (freeze-dried cake) obtained was calculated. Next, a vessel (trunk diameter 18 mm) filled with the non-powder-form freeze-dried composition obtained was installed in a jet type dry powder inhaler (having a bellows body capable of supplying an amount of air of about 20 ml) designed such that the bore of the air jet flow path was 1.2 mm and the bore of the discharge flow path was 1.8 mm), and as in Examples 1 to 37 this was directly jetted out into an Aerosizer (made by Amherst Process Instrument, Inc., USA) fitted with an Aerobreather (made by Amherst Process Instrument, Inc., USA; measurement conditions: breath rate: 60 L/min, breath volume: 1 L) (applying an air impact arising through an air speed of about 35 m/sec and an air flow rate of about 40 ml/sec to the freeze-dried cake), the particle size distribution of the fine particles jetted out was measured, and the mass median aerodynamic diameter (μm±SD) was calculated.

Furthermore, as in Examples 38 to 48, a vessel (trunk diameter 18 mm) filled with the non-powder-form freeze-dried composition obtained was installed in a self-inhaling type dry powder inhaler designed such that the bore of the air introduction flow path was 1.99 mm and the bore of the suction flow path was 1.99 mm. Using this, the fine particle fraction (%) was calculated with a twin impinger (made by Copley, UK) (applying an air impact arising through an air speed of about 95 m/sec and an air flow rate of 295 ml/sec to the freeze-dried cake).

The disintegration index, the mass median aerodynamic diameter (μm±SD) of the fine particles jetted out from the jet type dry powder inhaler, and the fine particle fraction (%) of the fine particles obtained by the self-inhaling type dry powder inhaler are shown in Table 9 for each of the freeze-dried compositions.

TABLE 9

| Freeze-dried composition | Disintegration index | Mass median aerodynamic diameter (μm ± SD, MMAD) | Fine particle fraction (%) |
| --- | --- | --- | --- |
| 71. Insulin + isoleucine | 0.124 | 1.759 ± 1.425 | 71.1 |
| 72. Insulin + leucine | 0.250 | 1.954 ± 1.454 | 74.1 |
| 73. Insulin +valine | 0.124 | 2.007 ± 1.438 | 72.1 |
| 74. Insulin + phenylalanine | 0.204 | 1.872 ± 1.477 | 62.0 |
| 75. Insulin + D-mannitol | 0.160 | 2.239 ± 1.435 | 61.2 |

As shown in Table 9, the non-powder-form freeze-dried compositions (freeze-dried cakes), which showed a disintegration index of 0.124 or more, were easily made into fine particles in the vessel by the air impact arising through an air speed of about 35 m/sec and an air flow rate of about 40 ml/sec or the air impact arising through an air speed of about 95 m/sec and an air flow rate of 295 ml/sec. Moreover, the mean particle diameter of the fine particles made by the air impact arising through an air speed of about 95 m/sec and an air flow rate of 295 ml/sec was less than 5 microns, and hence it was possible to produce a powdered preparation suitable for transpulmonary administration.

Example 76

500,000 IU of interferon-γ (IFN-γ) (made by Hayashibara Biochemical Laboratories, Inc., Japan, relative activity: 10,000,000 IU/mg) and the carrier shown in Table 10 were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form freeze-dried composition (freeze-dried cake) obtained was calculated.

Next, as in Examples 1 to 37, a vessel (trunk diameter 18 mm) filled with the non-powder-form freeze-dried composition obtained was installed in a jet type dry powder inhaler (having a bellows body capable of supplying an amount of air of about 20 ml) designed such that the bore of the air jet flow path was 1.2 mm and the bore of the discharge flow path was 1.8 mm), jetting was carried out directly into an Aerosizer (made by Amherst Process Instrument, Inc., USA) fitted with an Aerobreather (made by Amherst Process Instrument, Inc., USA; measurement conditions: breath rate: 60 L/min, breath volume: 1 L) (applying an air impact arising through an air speed of about 35 m/sec and an air flow rate of about 40 ml/sec to the freeze-dried cake), the particle size distribution of the fine particles jetted out was measured, and the mass median aerodynamic diameter (μm±SD) was calculated. The disintegration index and the mass median aerodynamic diameter (μm±SD) of the fine particles jetted out from the inhaler are shown in Table 10 for the freeze-dried composition.

TABLE 10

| Freeze-dried composition | Disintegration index | Mass median aerodynamic diameter (μm ± SD, MMAD) |
| --- | --- | --- |
| 76. IFN-γ + 1 mg Phe + 0.3 mg Leu + 0.2 mg Arg-HCl | 0.336 | 1.212 ± 1.384 |

Phe: Phenylalanine,
Leu: leucine,
Arg-HCl: arginine hydrochloride

As can be seen from Table 10, the non-powder-form freeze-dried composition (freeze-dried cake), which showed a disintegration index of 0.336, was easily made into fine particles in the vessel by the air impact arising through an air speed of about 35 m/sec and an air flow rate of about 40 ml/sec, and moreover the mean particle diameter was less than 5 microns, and hence it was possible to produce a powdered preparation suitable for transpulmonary administration.

Examples 77 and 78

10,000,000 IU or 2,500,000 IU of interferon-γ (IFN-γ) (made by Hayashibara Biochemical Laboratories, Inc., Japan, relative activity: 10,000,000 IU/mg) was made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form freeze-dried composition (freeze-dried cake) obtained was calculated. Next, as in Examples 1 to 37, a vessel (trunk diameter 18 mm) filled with the non-powder-form freeze-dried composition obtained was installed in a jet type dry powder inhaler (having a bellows body capable of supplying an amount of air of about 20 ml) designed such that the bore of the air jet flow path was 1.2 mm and the bore of the discharge flow path was 1.8 mm, and jetting was carried out directly into an Aerosizer (made by Amherst Process Instrument, Inc., USA) fitted with an Aerobreather (made by Amherst Process Instrument, Inc., USA; measurement conditions: breath rate: 60 L/min, breath volume: 1 L) (applying an air impact arising through an air speed of about 35 m/sec and an air flow rate of about 40 ml/sec to the freeze-dried cake), the particle size distribution of the fine particles jetted out was measured, and the mass median aerodynamic diameter (μm±SD) was calculated. The disintegration index and the mass median aerodynamic diameter (μm±SD) of the fine particles jetted out from the inhaler are shown in Table 11 for each of the freeze-dried compositions.

TABLE 11

| Freeze-dried composition | Disintegration index | Mass median aerodynamic diameter (μm ± SD, MMAD) |
| --- | --- | --- |
| 77. 10,000,000 IU of IFN-γ | 0.206 | 2.355 ± 1.439 |
| 78. 2,500,000 IU of IFN-γ | 0.160 | 2.244 ± 1.514 |

As shown in Table 11, despite not containing a carrier, the non-powder-form freeze-dried compositions (freeze-dried cakes), which showed a disintegration index of 0.160 or more, were easily made into fine particles in the vessel by the above-mentioned air impact, and moreover the mean particle diameter was less than 5 microns, and hence it was possible to produce a preparation suitable for transpulmonary administration.

Examples 79 to 83

28 μg of pUC19 DNA (2686 bp, made by Otsuka Pharmaceutical Co., Ltd., hereinafter referred to as 'pUC19 DNA'), which is a plasmid DNA, and 2.0 mg of any of various carriers as shown in Table 12 were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form freeze-dried composition (freeze-dried cake) obtained was calculated. Next, as in Examples 71 to 78, a vessel (trunk diameter 18 mm) filled with the non-powder-form freeze-dried composition obtained was installed in a jet type dry powder inhaler (having a bellows body capable of supplying an amount of air of about 50 ml) designed such that the bore of the air jet flow path was 1.2 mm and the bore of the discharge flow path was 1.8 mm, and jetting was carried out directly into an Aerosizer (made by Amherst Process Instrument, Inc., USA) fitted with an Aerobreather (made by Amherst Process Instrument, Inc., USA; measurement conditions: breath rate: 60 L/min, breath volume: 1 L) (applying an air impact arising through an air speed of about 89 m/sec and an air flow rate of about 100 ml/sec to the freeze-dried cake), the particle size distribution of the fine particles jetted out was measured, and the mass median aerodynamic diameter (μm±SD) was calculated. The disintegration index, and the mass median aerodynamic diameter of the fine particles jetted out from the inhaler are shown in Table 12 for each of the freeze-dried compositions.

TABLE 12

| Freeze-dried composition | Disintegration index | Mass median aerodynamic diameter (μm ± SD, MMAD) |
| --- | --- | --- |
| 79. pUC19 DNA + isoleucine | 0.103 | 2.168 ± 1.586 |
| 80. pUC19 DNA + leucine | 0.096 | 1.603 ± 1.580 |
| 81. pUC19 DNA + valine | 0.110 | 1.789 ± 1.486 |
| 82. pUC19 DNA + phenylalanine | 0.149 | 1.375 ± 1.545 |
| 83. pUC19 DNA + D-mannitol | 0.126 | 1.969 ± 1.503 |

As shown in Table 12, the non-powder-form freeze-dried compositions (freeze-dried cakes), which showed a disintegration index of 0.096 or more, were easily made into fine particles in the vessel by the air impact arising through an air speed of about 89 m/sec and an air flow rate of about 100 ml/sec, and moreover the mean particle diameter was less than 5 microns, and hence it was possible to produce a powdered preparation suitable for transpulmonary administration.

Examples 84 to 87

100 μg of an anti-interleukin-1β antibody (anti-IL-1β antibody) (made by Otsuka Pharmaceutical Co., Ltd., Japan) and 2.0 mg of any of various carriers as shown in Table 13 were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form cake-like freeze-dried composition (freeze-dried cake) obtained was calculated. Next, a vessel (trunk diameter 18 mm) filled with the non-powder-form freeze-dried composition obtained was installed in a jet type dry powder inhaler (having a bellows body capable of supplying an amount of air of about 20 ml) designed such that the bore of the air jet flow path was 1.2 mm and the bore of the discharge flow path was 1.8 mm, and jetting was carried out directly into an Aerosizer (made by Amherst Process Instrument, Inc., USA) fitted with an Aerobreather (made by Amherst Process Instrument, Inc., USA; measurement conditions: breath rate: 60 L/min, breath volume: 1 L) (applying an air impact arising through an air speed of about 35 m/sec and an air flow rate of about 40 ml/sec to the freeze-dried cake), the particle size distribution of the fine particles jetted out was measured, and the mass median aerodynamic diameter (μm±SD) was calculated. The disintegration index, and the mass median aerodynamic diameter (μm±SD) of the fine particles jetted out from the inhaler are shown in Table 13 for each of the freeze-dried compositions.

TABLE 13

| Freeze-dried composition | Disintegration index | Mass median aerodynamic diameter (μm ± SD, MMAD) |
|---|---|---|
| 84. Anti-IL-1β antibody + Ile | 0.272 | 1.668 ± 1.434 |
| 85. Anti-IL-1β antibody + Leu | 0.195 | 1.681 ± 1.404 |
| 86. Anti-IL-1β antibody + Val | 0.277 | 1.890 ± 1.392 |
| 87. Anti-IL-1β antibody + Phe | 0.358 | 1.462 ± 1.396 |

Ile: isoleucine,
Leu: leucine,
Val: valine,
Phe: phenylalanine

Each of the freeze-dried compositions obtained was a non-powder-form cake-like mass (freeze-dried cake) at the time of freeze-drying. As can be seen from Table 13, the non-powder-form freeze-dried cakes, which showed a disintegration index of 0.195 or more, were disintegrated by the air impact arising through an air speed of about 35 m/sec and an air flow rate of about 40 ml/sec, becoming fine particles of mass median aerodynamic diameter less than 5 microns, i.e. becoming a powdered preparation suitable for transpulmonary administration.

Examples 88 to 91

100 μg of an anti-interleukin-1α antibody (anti-IL-1α antibody) (made by Otsuka Pharmaceutical Co., Ltd., Japan) and 2.0 mg of any of various carriers as shown in Table 14 were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form cake-like freeze-dried composition (freeze-dried cake) obtained was calculated. Next, a vessel (trunk diameter 18 mm) filled with the non-powder-form freeze-dried composition obtained was installed in a jet type dry powder inhaler (having a bellows body capable of supplying an amount of air of about 20 ml) designed such that the bore of the air jet flow path was 1.2 mm and the bore of the discharge flow path was 1.8 mm, and as in Examples 84 to 87, an air impact arising through an air speed of about 35 m/sec and an air flow rate of about 40 ml/sec was applied to the freeze-dried cake in the vessel, the particle size distribution of the fine particles produced was measured, and the mass median aerodynamic diameter (μm±SD) was calculated. The disintegration index, and the mass median aerodynamic diameter (μm±SD) of the fine particles jetted out from the inhaler are shown in Table 14 for each of the freeze-dried compositions.

TABLE 14

| Freeze-dried composition | Disintegration index | Mass median aerodynamic diameter (μm ± SD, MMAD) |
|---|---|---|
| 88. Anti-IL-1α antibody + Ile | 0.253 | 1.515 ± 1.433 |
| 89. Anti-IL-1α antibody + Leu | 0.204 | 1.787 ± 1.435 |
| 90. Anti-IL-1α antibody + Val | 0.257 | 1.957 ± 1.393 |
| 91. Anti-IL-1α antibody + Phe | 0.258 | 1.707 ± 1.426 |

Ile: isoleucine,
Leu: leucine,
Val: valine,
Phe: phenylalanine

Each of the freeze-dried compositions obtained was a non-powder-form cake-like mass (freeze-dried cake) at the time of freeze-drying. As can be seen from Table 14, the non-powder-form freeze-dried cakes, which showed a disintegration index of 0.204 or more, were disintegrated by the air impact arising through an air speed of about 35 m/sec and an air flow rate of about 40 ml/sec, becoming fine particles of mass median aerodynamic diameter less than 5 microns, i.e. becoming a powdered preparation suitable for transpulmonary administration.

Examples 92 to 95

10 μg of calcitonin (made by Sigma, USA) and 2.0 mg of any of various carriers as shown in Table 15 were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form cake-like freeze-dried composition (freeze-dried cake) obtained was calculated. Next, a vessel (trunk diameter 18 mm) filled with the non-powder-form freeze-dried composition obtained was installed in a jet type dry powder inhaler (having a bellows body capable of supplying an amount of air of about 20 ml) designed such that the bore of the air jet flow path was 1.2 mm and the bore of the discharge flow path was 1.8 mm, and as in Examples 84 to 87, an air impact arising through an air speed of about 35 m/sec and an air flow rate of about 40 ml/sec was applied to the freeze-dried cake in the vessel, the particle size distribution of the fine particles produced was measured, and the mass median aerodynamic diameter (μm±SD) was calculated. The disintegration index, and the mass median aerodynamic diameter (μm±SD) of the fine particles jetted out from the inhaler are shown in Table 15 for each of the freeze-dried compositions.

TABLE 15

| Freeze-dried composition | Disintegration index | Mass median aerodynamic diameter (μm ± SD, MMAD) |
|---|---|---|
| 92. Calcitonin + isoleucine | 0.209 | 1.531 ± 1.457 |
| 93. Calcitonin + leucine | 0.273 | 1.699 ± 1.434 |
| 94. Calcitonin + valine | 0.248 | 1.421 ± 1.466 |
| 95. Calcitonin + phenylalanine | 0.150 | 1.653 ± 1.408 |

Each of the freeze-dried compositions obtained was a non-powder-form cake-like mass (freeze-dried cake) at the time of freeze-drying. As can be seen from Table 15, the non-powder-form freeze-dried cakes, which showed a disintegration index of 0.150 or more, were disintegrated by the air impact arising through an air speed of about 35 m/sec and an air flow rate of about 40 ml/sec, becoming fine particles of mass median aerodynamic diameter less than 5 microns, i.e. becoming a powdered preparation suitable for transpulmonary administration.

Examples 96 to 100

12 μg of erythropoietin (made by Wako Pure Chemical Industries, Ltd., Japan) and 2.0 mg of any of various carriers as shown in Table 16 were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form cake-like freeze-dried composition (freeze-dried cake) obtained was calculated. Next, a vessel (trunk diameter 18 mm) filled with the non-powder-form freeze-dried composition obtained was installed in a jet type dry powder inhaler (having a bellows body capable of supplying an amount of air of about 20 ml) designed such that the bore of the air jet flow path was 1.2 mm and the bore of the discharge flow path was 1.8 mm, and as in Examples 84 to 87, an air impact arising through an air speed of about 35 m/sec and an air flow rate of about 40 ml/sec was applied to the freeze-dried cake in the vessel, the particle size distribution of the fine particles produced was measured, and the mass median aerodynamic diameter (μm±SD) was calculated. The disintegration index, and the mass median aerodynamic diameter (μm±SD) of the fine particles jetted out from the inhaler are shown in Table 16 for each of the freeze-dried compositions.

TABLE 16

| Freeze-dried composition | Disintegration index | Mass median aerodynamic diameter (μm ± SD, MMAD) |
|---|---|---|
| 96. Erythropoietin + isoleucine | 0.287 | 1.214 ± 1.396 |
| 97. Erythropoietin + leucine | 0.213 | 1.833 ± 1.429 |
| 98. Erythropoietin + valine | 0.254 | 1.670 ± 1.444 |
| 99. Erythropoietin + phenylalanine | 0.309 | 1.923 ± 1.447 |
| 100. Erythropoietin + D-mannitol | 0.155 | 1.795 ± 1.412 |

Each of the freeze-dried compositions obtained was a non-powder-form cake-like mass (freeze-dried cake) at the time of freeze-drying. As can be seen from Table 16, the non-powder-form freeze-dried cakes, which showed a disintegration index of 0.155 or more, were disintegrated by the air impact arising through an air speed of about 35 m/sec and an air flow rate of about 40 ml/sec, becoming fine particles of mass median aerodynamic diameter less than 5 microns, i.e. becoming a powdered preparation suitable for transpulmonary administration.

Example 101

20 μg of granulocyte colony stimulating factor (G-CSF) (made by Evermore Bio, China) and 2.5 mg of D-mannitol were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form cake-like freeze-dried composition (freeze-dried cake) obtained was calculated. Next, a vessel (trunk diameter 18 mm) filled with the non-powder-form freeze-dried composition obtained was installed in a jet type dry powder inhaler (having a bellows body capable of supplying an amount of air of about 20 ml) designed such that the bore of the air jet flow path was 1.2 mm and the bore of the discharge flow path was 1.8 mm, and as in Examples 84 to 87, an air impact arising through an air speed of about 35 m/sec and an air flow rate of about 40 ml/sec was applied to the freeze-dried cake in the vessel, the particle size distribution of the fine particles produced was measured, and the mass median aerodynamic diameter (μm±SD) was calculated. The disintegration index, and the mass median aerodynamic diameter (μm±SD) of the fine particles jetted out from the inhaler are shown in Table 17 for the freeze-dried composition.

TABLE 17

| Freeze-dried composition | Disintegration index | Mass median aerodynamic diameter (μm ± SD, MMAD) |
|---|---|---|
| 101. G-CSF + D-mannitol | 0.049 | 1.795 ± 1.412 |

The freeze-dried composition obtained was a non-powder-form cake-like mass (freeze-dried cake) at the time of freeze-drying. As can be seen from Table 17, the non-powder-form freeze-dried cake, which showed a disintegration index of 0.049, was disintegrated by the air impact arising through an air speed of about 35 m/sec and an air flow rate of about 40 ml/sec, becoming fine particles of mass median aerodynamic diameter less than 5 microns, i.e. becoming a powdered preparation suitable for transpulmonary administration.

Examples 102 to 104

100 μg of growth hormone (made by Wako Pure Chemical Industries, Ltd., Japan) and any of various carriers as shown in Table 18 were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form cake-like freeze-dried composition (freeze-dried cake) obtained was calculated. Next, a vessel (trunk diameter 18 mm) filled with the non-powder-form freeze-dried composition obtained was installed in a jet type dry powder inhaler (having a bellows body capable of supplying an amount of air of about 20 ml) designed such that the bore of the air jet flow path was 1.2 mm and the bore of the discharge flow path was 1.8 mm, and as in Examples 84 to 87, an air impact arising through an air speed of about 35 m/sec and an air flow rate of about 40 ml/sec was applied to the freeze-dried cake in the vessel, the particle size distribution of the fine particles produced was measured, and the mass median aerodynamic diameter (μm±SD) was calculated. The disintegration index, and the mass median aerodynamic diameter (μm±SD) of the particles jetted out from the inhaler are shown in Table 18 for each of the freeze-dried compositions.

TABLE 18

| Freeze-dried composition | Disintegration index | Mass median aerodynamic diameter (μm ± SD, MMAD) |
|---|---|---|
| 102. GH + 1.5 mg Ile + 0.1 mg mannitol + 0.02 mg Gly | 0.250 | 1.626 ± 1.473 |
| 103. GH + 1.5 mg Val + 0.1 mg mannitol + 0.02 mg Gly | 0.270 | 1.675 ± 1.461 |

TABLE 18-continued

| Freeze-dried composition | Disintegration index | Mass median aerodynamic diameter (μm ± SD, MMAD) |
|---|---|---|
| 104. GH + 1.5 mg Phe + 0.1 mg mannitol + 0.02 mg Gly | 0.362 | 1.286 ± 1.375 |

GH: Growth hormone,
Ile: isoleucine,
Val: valine,
Gly: glycine,
mannitol: D-mannitol,
Phe: phenylalanine Each of the freeze-dried compositions obtained was a non-powder-form cake-like mass (freeze-dried cake) at the time of freeze-drying. As can be seen from Table 18, the non-powder-form freeze-dried cakes, which showed a disintegration index of 0.250 or more, were disintegrated by the air impact arising through an air speed of about 35 m/sec and an air flow rate of about 40 ml/sec, becoming fine particles of mass median aerodynamic diameter less than 5 microns, i.e. becoming a powdered preparation suitable for transpulmonary administration.

Examples 105 to 107

1 mg of deoxyribonuclease (Dnase) (made by Sigma, USA) and 2 mg of any of various carriers as shown in Table 19 were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form cake-like freeze-dried composition (freeze-dried cake) obtained was calculated. Next, a vessel (trunk diameter 18 mm) filled with the non-powder-form freeze-dried composition obtained was installed in a jet type dry powder inhaler (having a bellows body capable of supplying an amount of air of about 20 ml) designed such that the bore of the air jet flow path was 1.2 mm and the bore of the discharge flow path was 1.8 mm, and as in Examples 84 to 87, an air impact arising through an air speed of about 35 m/sec and an air flow rate of about 40 ml/sec was applied to the freeze-dried cake in the vessel, the particle size distribution of the fine particles produced was measured, and the mass median aerodynamic diameter (μm±SD) was calculated. The disintegration index, and the mass median aerodynamic diameter (μm±SD) of the fine particles jetted out from the inhaler are shown in Table 19 for each of the freeze-dried compositions.

TABLE 19

| Freeze-dried composition | Disintegration index | Mass median aerodynamic diameter (μm ± SD, MMAD) |
|---|---|---|
| 105. Dnase + isoleucine | 0.142 | 1.737 ± 1.452 |
| 106. Dnase + valine | 0.209 | 2.014 ± 1.449 |
| 107. Dnase + phenylalanine | 0.078 | 2.425 ± 1.462 |

Each of the freeze-dried compositions obtained was a non-powder-form cake-like mass (freeze-dried cake) at the time of freeze-drying. As can be seen from Table 19, the non-powder-form freeze-dried cakes, which showed a disintegration index of 0.078 or more, were disintegrated by the air impact arising through an air speed of about 35 m/sec and an air flow rate of about 40 ml/sec, becoming fine particles of mass median aerodynamic diameter less than 5 microns, i.e. becoming a powdered preparation suitable for transpulmonary administration.

Examples 108 and 109

10 μg of parathyroid hormone (PTH) (made by Sigma, USA) and 2 mg of any of various carriers as shown in Table 20 were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form cake-like freeze-dried composition (freeze-dried cake) obtained was calculated. Next, a vessel (trunk diameter 18 mm) filled with the non-powder-form freeze-dried composition obtained was installed in a jet type dry powder inhaler (having a bellows body capable of supplying an amount of air of about 20 ml) designed such that the bore of the air jet flow path was 1.2 mm and the bore of the discharge flow path was 1.8 mm), and as in Examples 84 to 87, an air impact arising through an air speed of about 35 m/sec and an air flow rate of about 40 ml/sec was applied to the freeze-dried cake in the vessel, the particle size distribution of the fine particles produced was measured, and the mass median aerodynamic diameter (μm±SD) was calculated. The disintegration index, and the mass median aerodynamic diameter (μm±SD) of the fine particles jetted out from the inhaler are shown in Table 20 for each of the freeze-dried compositions.

TABLE 20

| Freeze-dried composition | Disintegration index | Mass median aerodynamic diameter (μm ± SD, MMAD) |
|---|---|---|
| 108. PTH + phenylalanine | 0.273 | 1.090 ± 1.346 |
| 109. PTH + D-mannitol | 0.234 | 1.603 ± 1.504 |

Each of the freeze-dried compositions obtained was a non-powder-form cake-like mass (freeze-dried cake) at the time of freeze-drying. As can be seen from Table 20, the non-powder-form freeze-dried cakes, which showed a disintegration index of 0.234 or more, were disintegrated by the air impact arising through an air speed of about 35 m/sec and an air flow rate of about 40 ml/sec, becoming fine particles of mass median aerodynamic diameter less than 5 microns, i.e. becoming a powdered preparation suitable for transpulmonary administration.

Example 110

100 μg of leuprolide (made by Sigma, USA) and 2 mg of phenylalanine were made up to 0.5 ml by dissolving in injection distilled water, this was filled into vessels (trunk diameter 18 mm), and freeze-drying was carried out using a shelf-type freeze-dryer (Lyovac GT-4, made by Leybold). The disintegration index of the non-powder-form cake-like freeze-dried composition (freeze-dried cake) obtained was calculated. Next, a vessel (trunk diameter 18 mm) filled with the non-powder-form freeze-dried composition obtained was installed in a jet type dry powder inhaler (having a bellows body capable of supplying an amount of air of about 20 ml) designed such that the bore of the air jet flow path was 1.2 mm and the bore of the discharge flow path was 1.8 mm, and as in Examples 84 to 87, an air impact arising through an air speed of about 35 m/sec and an air flow rate of about 40 ml/sec was applied to the freeze-dried cake in the vessel, the particle size distribution of the fine particles produced was measured, and the mass median aerodynamic diameter (μm±SD) was calculated. The disintegration index, and the mass median aerodynamic diameter (μm±SD) of the fine particles jetted out from the inhaler are shown in Table 21 for the freeze-dried composition.

TABLE 21

| Freeze-dried composition | Disintegration index | Mass median aerodynamic diameter (μm ± SD, MMAD) |
|---|---|---|
| 110. Leuprolide + Phe | 0.358 | 1.115 ± 1.350 |

Phe: phenylalanine

The freeze-dried composition obtained was a non-powder-form cake-like mass (freeze-dried cake) at the time of freeze-drying. As can be seen from Table 21, the non-powder-form freeze-dried cake, which showed a disintegration index of 0.358, was disintegrated by the air impact arising through an air speed of about 35 m/sec and an air flow rate of about 40 ml/sec, becoming fine particles of mass median aerodynamic diameter less than 5 microns, i.e. becoming a powdered preparation suitable for transpulmonary administration.

INDUSTRIAL APPLICABILITY

According to the dry powder inhalation system for transpulmonary administration of the present invention, a freeze-dried composition can be made into fine particles down to a size necessary for delivery into the lungs, and moreover administration of the fine particles into the lungs through inhalation is possible. That is, according to the dry powder inhalation system for transpulmonary administration of the present invention, a freeze-dried composition that has been prepared in a non-powder form can be made into fine particles at the time of use (the time of administration), and administered through inhalation at the same time, and hence a special operation for making the preparation into fine particles becomes unnecessary. Consequently, according to the dry powder inhalation system for transpulmonary administration (preparation system) of the present invention, there is no risk of loss during the manufacturing process (deactivation of the drug or collection loss through a filling operation) or loss during storage (for example deactivation of the drug due to being stored in a fine particle form), or contamination with impurities during the manufacturing process; a desired fixed amount can thus be administered stably. This is useful in particular with preparations having as an active ingredient a generally expensive pharmacologically active substance such as a protein or a peptide.

The proportion of effective particles (fine particle fraction) attained by the dry powder inhalation system for transpulmonary administration of the invention is at least 10%, and can be increased to at least 20%, at least 25%, at least 30% or at least 35%. U.S. Pat. No. 6,153,224 indicates that, with many of prior art dry powder inhalers, the proportion of the active ingredient (particles) to adhere to the lower portions of the lungs is only about 10% of the amount of the active ingredient inhaled. Further, Japanese Unexamined Patent Publication No. 2001-151673 states that the amount of an inhalation powder preparation reaching the lungs (lung reaching proportion) is generally about 10% of the drug discharged from the preparation. Therefore, the dry powder inhalation system of the invention is valuable in that it is capable of achieving a higher proportion of effective particles (fine particle fraction) than prior art powder inhalation preparations.

According to the freeze-dried composition and jet type dry powder inhaler of the present invention, the freeze-dried composition can be made into fine particles merely by jetting air into the vessel from the air jet flow path using the air pressure-feeding means and thus applying a slight air impact to the freeze-dried composition. The making into fine particles can thus be carried out at the time of use with an dry powder inhaler having a simple structure and moreover with simple handling. Moreover, because the dry powder inhaler has a simple structure, it can be produced with a low manufacturing cost, and hence mass distribution is possible.

Moreover, according to the jet type dry powder inhaler, by adjusting the speed of compression of the air pressure-feeding means such as a bellows body, the amount sucked in of the aerosol (powdered preparation) can be adjusted in accordance with the respiratory ability of the user. Moreover, by using a single integrated needle part, the operation of piercing the stopper of the vessel with the needle part becomes simple.

Furthermore, according to the self-inhaling type dry powder inhaler, the freeze-dried composition can be made into an aerosol (made into fine particles) through an air impact being generated by the inhalation pressure of the user, and hence the making into fine particles and administration into the lungs of the freeze-dried composition can be carried out at the same time as the user inhaling, and thus it can be expected that the drug will be administered in a stable amount with no loss. Moreover, a separate special operation for making into an aerosol (making into fine particles) is unnecessary, and hence handling is easy. Moreover, as with the jet type, by using a single integrated needle part, the operation of piercing the elastic port stopper of the vessel with the needle part becomes simple.

According to the dry powder inhaler of the present invention, by piercing the stopper of the vessel with the tip of the needle part having the suction flow path and the air introduction flow path, and air in the vessel then being sucked in from the suction port by the inhalation pressure of the user (patient), air can be made to flow into the vessel from the air introduction flow path of the needle part, thus applying an air impact to the freeze-dried composition, and the freeze-dried composition that has been made into a powder can be sucked in from the vessel.

Moreover, in the case of the dry powder inhaler of the present invention disclosed as Embodiment 4 in particular, the following effects are exhibited.

When trying to apply an effective air impact to the freeze-dried composition and suck the powder-form freeze-dried composition that has been made into fine particles from the vessel, the cross-sectional areas of the suction flow path and the air introduction flow path must be made large, and hence the diameter of the needle part must be made large.

However, in the case of piercing a needle part having a large diameter through the stopper, it becomes necessary to hold the vessel securely, and in this state move the vessel towards the needle tip without deviating away from the axis of the needle part, and push the stopper against the needle tip with a large force.

As described above, the dry powder inhaler of the present invention thus has a holder part that holds the vessel, a guide part of the holder part, and a holder operating part having a mechanism part and an operating member that operates the mechanism part. Therefore, by holding the vessel with the holder part, moving the vessel along the axis of the needle part following the guide part towards the needle tip, and operating the operating member, it is thus possible to pierce the needle part through the stopper of the vessel using a relatively low force.

In this way, according to the dry powder inhaler of the present invention, the stopper of the vessel can be pierced by the needle part easily and reliably.

Moreover, if a constitution is adopted in which the housing is formed in a tubular shape, the suction port is formed at a tip part of the housing, a housing chamber for the vessel is formed in the housing, the needle part is disposed in the housing so that the needle tip points towards the housing chamber, an introduction port for introducing outside air that communicates with the air introduction flow path of the needle part is provided in a wall of the housing, and the holder part is advanced and retreated in the axial direction of the housing in the housing chamber using the holder operating part, then a pencil-shaped dry powder inhaler can be formed, which is easy to use and conveniently portable.

Moreover, if the constitution is made to be such that the housing is formed from a housing main body having a removal/insertion port for the vessel in a position in which the holder part is retreated, and a lid for the removal/insertion port that is connected to the housing main body by a hinge, the holder operating part has a mechanism part which moves the holder part forwards when the lid is pushed down and the removal/insertion port closed, and moves the holder part backwards when the lid is lifted up and the removal/insertion port opened, and the lid is used as the operating member of the mechanism part, then the mechanism part of the holder operating part can be simplified and in the manufacturing cost. Moreover, the removal/insertion port of the vessel can be closed at the same time as piercing the stopper of the vessel with the needle tip, and hence use becomes easier.

What is claimed is:

1. A method of making a non-powder-form freeze-dried composition comprising:
   at least partially filing a vessel with a solution; and
   freeze drying the solution in the vessel to form the non-powder-form freeze-dried composition;
   wherein the non-powder-form freeze-dried composition has at least the following properties:
      a disintegration index greater than or equal to 0.015; and
      the non-powder-form freeze-dried composition becomes fine particles upon receiving air impact at an air speed greater than or equal to 1 meter/second and an air flow rate greater than or equal to 17 milliliters/second; and
   wherein the fine particles have:
      a mean particle diameter less than or equal to $1 \times 10^{-5}$ meters; or
      a fine particle fraction greater than or equal to 10%; or
      a mean particle diameter less than or equal to $1 \times 10^{-5}$ meters and a fine particle fraction greater than or equal to 10%.

2. The method of claim 1, wherein after making the composition, the vessel is sealed.

3. The method of claim 1, wherein the disintegration index is greater than or equal to 0.02.

4. The method of claim 1, wherein the disintegration index is less than or equal to 1.5.

5. The method of claim 1, wherein the air speed is greater than or equal to 2 meters/second.

6. The method of claim 1, wherein the air speed is less than or equal to 300 meters/second.

7. The method of claim 1, wherein the air flow rate is greater than or equal to 20 milliliters/second.

8. The method of claim 1, wherein the air flow rate is less than or equal to 15 liters/second.

9. The method of claim 1, wherein the fine particles have:
   a mean particle diameter less than or equal to $5 \times 10^{-6}$ meters; or
   a fine particle fraction greater than or equal to 20%; or
   a mean particle diameter less than or equal to $5 \times 10^{-6}$ meters and a fine particle fraction greater than or equal to 20%.

10. The method of claim 1, wherein the fine particle fraction is greater than or equal to 35%.

11. The method of claim 1, wherein the composition is water soluble.

12. The method of claim 1, wherein the composition comprises at least one carrier.

13. The method of claim 12, wherein the at least one carrier is selected from:
   amino acids,
   dipeptides,
   tripeptides, and/or
   saccharides.

14. The method of claim 1, wherein the composition comprises at least one additive.

15. The method of claim 1, wherein the composition comprises:
   at least one active ingredient;
   one or more carriers; and
   at least one additive.

16. The method of claim 14 or 15, wherein the at least one additive comprises one or more:
   surfactants; and/or
   buffering agents.

17. The method of claim 1, wherein the composition contains only a single dose of at least one active ingredient.

18. The method of claim 1, wherein the composition contains two doses of at least one active ingredient.

19. The method of claim 1, wherein the composition contains a plurality of doses of at least one active ingredient.

20. The method of claim 1, wherein the composition contains only a single dose of a plurality of active ingredients.

21. The method of claim 1, wherein the composition contains a plurality of active ingredients, and
   wherein the composition contains two doses of the plurality of active ingredients.

22. The method of claim 1, wherein the composition contains a plurality of active ingredients, and
   wherein the composition contains more than one dose of the plurality of active ingredients.

23. A non-powder-form freeze-dried composition made by the method of claim 1.

24. A non-powder-form freeze-dried composition made by the method of claim 17.

25. A method of making a dry powder for transpulmonary administration, comprising:
   directing air at an air speed greater than or equal to 1 meter/second and an air flow rate greater than or equal to 17 milliliters/second onto a non-powder-form freeze-dried composition to produce fine particles of dry powder;
   wherein the non-powder-form freeze-dried composition has a disintegration index greater than or equal to 0.015,
   wherein the non-powder-form freeze-dried composition is made into fine particles when it receives air impact at an air speed greater than or equal to 1 meter/second and an air flow rate greater than or equal to 17 milliliters/second, and wherein the fine particles have:
a mean particle diameter less than or equal to $1\times10^{-5}$ meters; or
a fine particle fraction greater than or equal to 10%; or
a mean particle diameter less than or equal to $1\times10^{-5}$ meters and a fine particle fraction greater than or equal to 10%.

26. The method of claim 25, wherein the composition is contained in a vessel.

27. The method of claim 25, wherein the disintegration index is greater than or equal to 0.02.

28. The method of claim 25, wherein the air speed is greater than or equal to 2 meters/second.

29. The method of claim 25, wherein the air flow rate is greater than or equal to 20 milliliters/second.

30. The method of claim 25, wherein the fine particles have:
a mean particle diameter less than or equal to $5\times10^{-6}$ meters; or
a fine particle fraction greater than or equal to 20%; or
a mean particle diameter less than or equal to $5\times10^{-6}$ meters and a fine particle fraction greater than or equal to 20%.

31. A method of transpulmonary administration comprising:
directing air at an air speed greater than or equal to 1 meter/second and an air flow rate greater than or equal to 17 milliliters/second onto a non-powder-form freeze-dried composition to produce fine particles; and
inhaling the fine particles;
wherein the non-powder-form freeze-dried composition has a disintegration index greater than or equal to 0.015,
wherein the non-powder-form freeze-dried composition is made into the fine particles by receiving air impact at an air speed greater than or equal to 1 meter/second and an air flow rate greater than or equal to 17 milliliters/second, and
wherein the fine particles have:
a mean particle diameter less than or equal to $1\times10^{-5}$ meters; or
a fine particle fraction greater than or equal to 10%; or
a mean particle diameter less than or equal to $1\times10^{-5}$ meters and a fine particle fraction greater than or equal to 10%.

32. The method of claim 31, wherein the composition is contained in a vessel.

33. The method of claim 32, wherein the vessel is associated with a dry powder inhaler comprising:
an inlet flow path; and
an outlet flow path;
wherein the air flows through the inlet flow path to impact the non-powder-form freeze-dried composition in the vessel.

34. The method of claim 33, wherein the air flows from a source of pressurized air associated with the inlet flow path to impact the non-powder-form freeze-dried composition in the vessel.

35. The method of claim 33, wherein the outlet flow path is associated with an inhalation port,
wherein the inhaling is conducted through the inhalation port and causes a negative pressure in the outlet flow path,
wherein the negative pressure causes air from the inlet flow path to impact the non-powder-form freeze-dried composition in the vessel, and
wherein at least some air from the inlet flow path and substantially all of the fine particles move from the vessel to the inhalation port via the outlet flow path.

36. A method of transpulmonary administration comprising:
making fine particles from a non-powder-form freeze-dried composition; and
administering the fine particles to an individual by inhalation;
wherein the non-powder-form freeze-dried composition has a disintegration index greater than or equal to 0.015,
wherein the non-powder-form freeze-dried composition is made into the fine particles by receiving air impact at an air speed greater than or equal to 1 meter/second and an air flow rate greater than or equal to 17 milliliters/second, and
wherein the fine particles comprise:
a mean particle diameter less than or equal to $1\times10^{-5}$ meters; or
a fine particle fraction greater than or equal to 10%; or
a mean particle diameter less than or equal to $1\times10^{-5}$ meters and a fine particle fraction greater than or equal to 10%.

37. The method of claim 36, wherein the non-powder-form freeze-dried composition comprises:
one or more active ingredients;
one or more carriers; and
at least one additive.

38. The method of claim 36, wherein the non-powder-form freeze-dried composition comprises a single dose of one or more active ingredients.

39. The method of claim 36, wherein the non-powder-form freeze-dried composition comprises a plurality of doses of one or more active ingredients.

* * * * *